US010648043B2

(12) United States Patent
Zhu et al.

(10) Patent No.: US 10,648,043 B2
(45) Date of Patent: May 12, 2020

(54) METHOD OF PRODUCING FATTY ACIDS

(71) Applicant: TOTAL RAFFINAGE CHIMIE, Courbevoie (FR)

(72) Inventors: Zhiwei Zhu, Mölndal (SE); Anastasia Krivoruchko, Gothenburg (SE); Jens Nielsen, Gothenburg (SE)

(73) Assignee: TOTAL RAFFINAGE CHIMIE, Courbevoie (FR)

( * ) Notice: Subject to any disclaimer, the term of this patent is extended or adjusted under 35 U.S.C. 154(b) by 2 days.

(21) Appl. No.: 16/072,101

(22) PCT Filed: Feb. 20, 2017

(86) PCT No.: PCT/EP2017/053811
§ 371 (c)(1),
(2) Date: Jul. 23, 2018

(87) PCT Pub. No.: WO2017/148727
PCT Pub. Date: Sep. 8, 2017

(65) Prior Publication Data
US 2019/0040477 A1   Feb. 7, 2019

(30) Foreign Application Priority Data

Mar. 4, 2016   (EP) .................................. 16158805

(51) Int. Cl.
| | | |
|---|---|---|
| *C12N 9/00* | (2006.01) | |
| *C12N 9/16* | (2006.01) | |
| *C12P 7/64* | (2006.01) | |
| *C12R 1/865* | (2006.01) | |
| *C12N 9/10* | (2006.01) | |
| *C12N 15/52* | (2006.01) | |
| *C07K 14/195* | (2006.01) | |
| *C07K 14/395* | (2006.01) | |

(52) U.S. Cl.
CPC ............ *C12R 1/865* (2013.01); *C07K 14/195* (2013.01); *C07K 14/395* (2013.01); *C12N 9/1029* (2013.01); *C12N 9/16* (2013.01); *C12N 15/52* (2013.01); *C12P 7/6409* (2013.01); *C12P 7/6454* (2013.01); *C12Y 203/01085* (2013.01); *C12Y 301/02007* (2013.01)

(58) Field of Classification Search
CPC ....... C12P 7/6409; C12N 9/16; C12N 9/0006; C12Y 101/0133; C12Y 101/011; C12Y 101/02014
See application file for complete search history.

(56) References Cited

FOREIGN PATENT DOCUMENTS

| WO | 2015054138 | 4/2015 |
| WO | 2017148727 | 9/2017 |

OTHER PUBLICATIONS

Fernandez-Moya et al., Biotechnol. Bioeng., 112(12), 2015.*
Tehlivets et al., BBA, 1771, 255-270, 2007.*
Fernandez-Moya et al., "Functional Replacement of the *Saccharomyces cerevisiae* Fatty Acid Synthase With a Bacterial Type II System Allows Flexible Produce Profiles", Biotechnol, Bioeng. Dec. 2015; 112(12) ; 2618-2623.
Leber et al.,"Engineering of *Saccharomyces cerevisiae* for the Synthesis of Short Chain Fatty Acides", Biotechnol, Bioeng. Feb. 2014; 111(2) ; 347-358.
Leibundgut et al.,"The multienzyme architecture of eukaryotic fatty acid synthases", Current Opinion in Structural Biology 2008; 18: 714-725.
Zhu et al."Expanding the product portfolio of fungal type I fatty acid synthases", Nature Chemical Biology; Apr. 2017;13:360-364.

* cited by examiner

*Primary Examiner* — Maryam Monshipouri
(74) *Attorney, Agent, or Firm* — James S. Keddie; Bozicevic, Field & Francis LLP

(57) ABSTRACT

The present invention relates to a method for producing fatty acids, in particular shot/medium-chain fatty acids (S/MCFA), by expression in a host cell of a recombinant fatty acid synthase (FAS) naturally devoid of a thioesterase (TE) domain comprising a heterologous thioesterase (TE). The invention further relates to polynucleotides comprising such recombinant FAS, polypeptides encoded thereby, and vectors comprising such polynucleotides, as well as recombinant host cells comprising the polynucleotides, polypeptides, or vectors.

17 Claims, 43 Drawing Sheets
Specification includes a Sequence Listing.

*R. toruloides* FAS
*R. toruloides* FAS ACPI2TE
*R. toruloides* FAS ACPII2TE
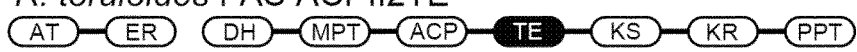
*A. kerguelense* FAS
*A. kerguelense* FAS ACPI2TE
*A. kerguelense* FAS ACPII2TE
*S. cerevisiae* FAS
*S. cerevisiae* FAS TE-ACP
*S. cerevisiae* FAS ACP-TE
FIG. 1

| | C6 | C8 | C10 | C12 | C14 | C16 | C16:1 | C18 | C18:1 | Sum |
|---|---|---|---|---|---|---|---|---|---|---|
| ACPI2TE | 0.012 ± 0.0002 | 0.092 ± 0.009 | 0.140 ± 0.006 | 0.304 ± 0.006 | 0.192 ± 0.0003 | 4.15 ±0.03 | 22.83 ± 0.06 | 1.47 ±0.01 | 29.95 ± 0.47 | 59.142 |
| ACPII2TE | 0.012 ± 0.0007 | 0.145 ± 0.008 | 0.196 ± 0.007 | 0.507 ± 0.017 | 0.271 ± 0.003 | 4.52 ±0.10 | 26.35 ± 0.04 | 0.84 ±0.02 | 22.71 ± 0.59 | 55.554 |
| WT | 0.009 ± 0.0008 | 0.003 ± 0.0002 | 0.036 ± 0.005 | 0.051 ± 0.005 | 0.094 ± 0.008 | 5.02 ±0.27 | 25.19 ± 1.77 | 1.35 ±0.18 | 37.81 ± 1.15 | 69.556 |
| ScFAS | 0.015 ± 0.0014 | 0.050 ± 0.005 | 0.281 ± 0.036 | 0.478 ± 0.063 | 0.204 ± 0.032 | 8.93 ±1.00 | 26.50 ± 2.49 | 0.57 ±0.07 | 13.96 ± 1.31 | 50.985 | mg/g Dry Cell Weight

SEQ ID NO1:
\>RtFAS1
atgaacggccgagcgacgcggagcgtgactgggacgtcgacgccggtccacacggcgacgacccgacccctcgtcctctt
gcaccctcgacccaaacccgcatctcgctgcacgtccctccacgtcgcaggaatggatcgccgccgaagtcgcgcgcga
caccttccaggactggcttcacgctgccgagaagagcggaaacctcgtcggattcgaggcggccgagcttgacgacgagca
ggctggcgagggcgacgacgagaaggagctcgtcctcaccgcctacttcttgaagcacgttgccggccttctcccctcccgt
cgacagctacctcccccgccaccgccgccgtcctcctcgccgccttcaaccactttgcgtccgtctacctcagcggaaccgat
gttcacaccctcactgcctcgctcgctgctcccgtccgcgctctcgtcatctcgtccttcttcctcgccaagaccaagctcgaggt
cgagggactcggcaaggtcttgcccaagcagtccgagtcggcgctcctgcagaaggctgcgaccggccaggcagaggtct
tcgctctcttcggtggtcagggaatgaacgaggtctactttgacgagctccagaccctccacgacctttacaccccgctgcttac
gcccttcctcgcccgcgcctccgaacacctcgtctctcgctgccgccgagcagcacaccctcctttacgaccactcgctcg
acgcccttgcctggctgcaagatccctctacccgccccgaagtcccctacctcgcgacttgcgccgtctcgctccctctcatcg
gtctcactcagctctgccagtacgtcgtgtacggcaaggctcgtcgctcggtcccgccgagctcggcgccaagttcaaggg
cgcgaccggccactcgcagggtgtcgtctcggctcttgtcatcgcgcacgagtaccctcccgcgtccaaggacggcagcga
cgcgtgggagcctttctacgagcaggcccttcgcggtttgaccgtcctcttccagatcggtctccagggcacgctcgccttccc
ctccatcgccatttcgcccgctctcgagtcgagctcggtcgagaatggcgagggtgtcccgactgccatgcttgccgtcaccg
gcctcgacctcaagtcgctcgagaagaagatcgccgaggtcaatgggcacgtcaagtctgagggccgcgacgagaccgtct
cgatcagtctctacaacggtgcgagggcgttcgtcgtcactggtgcgccgaaggacctcgtcggtctcgccgacggccttcg
caagaaccgcgcgccggccggcaaggaccagtcgaagatcccgcactcgaagcgtctccccgtcttctcgatgcgcttcctc
cccatcaacgttccctaccactcgcatctcctccaaggcgcgaccgagaaggcgctcgcgacgttctcggctgaggaggcc
gcccactgggcgccttcatcgttcacctgcgccgtctacaacaccgaggacggctccgacatgcgccagctctcggcttcgtc
ggttctcgagtcggtcttccagcagatcttcacctcgcccattcactgggtctcgcacgccaccaacttcccctcgtccgcgacg
cacgccatcgatttcggcacgggcggcgcgagcggcatcggttcgctctgcgcgcgcaactggagggccgcggtatccg
cacgattatgctcggcaaccgcggcgagggcgttggtgccggcaaggaggcttggggcaagaaggtcccgaccgaggag
aagtggaacgagcgcttccaccctcgcctcgtccgcaccagcgacggcaagatccacctcgacacgcccttctcgcgcctcc
tctcgaagccgcccctcatggtcggtggtatgaccccgacgaccgtcaaggccggcttcgtctcggccgttctccgcgcggg
ctaccacatcgagctcgctggcggcggtcactacaacgagaaggctgtccgtgccaaggtcgccgagatccagaagctcgt
gaacaagcccggcatgggcatcaccctcaactcgctctacatcaaccagcgccagtggacgttccagttcccgctctgggcc
aagatgaagcaggagggcgagcccgtcgagggtctctgtgttgctgccggtattccctcaaccgagaaggccaaggagatc
atcgacacgctccgcgaggccggcatcaagcacgtctcgttcaagcccggttcggtcgacggcatccgccaggtcgtcaac
atcgcctccgccaaccccgacttccccatcatcctccagtggactggtggtcgcgccggcggtcaccactcgtgcgaggactt
ccacgccccgatcctcgcgacgtacgcttcgatccgtcagcacccccaacatcaagctcgtcgccggctctggcttcggctcg
gctgagggatgctacccttaccttcgggcgagtggtcggagaagcagtacggcgtcgcgcgcatgccgttcgacggcttca
tgtttgcttcgtgggtcatggtcgccaaggaggcgcacacgagcgagtcggtcaagcagctcatcgtcgacgcgcctggtgt
cgaggatggccagtgggagcagacgtacgacaagccgaccggcggcatcctcaccgtcaactcggagcttggcgagccg
atccacaaggtcgcgactcgtggtgtcaagctgtgggccgagttcgacaagaaggtcttctcgctgtcgaaggagaagcagc
tcgcatggctcgccgacaacaagaagtacgttatcgaccgcctcaacgccgatttccagaagccctggttccccgccaaggc
cgacggctctccttgcgaccttgccgacatgacctacgccgaggtcaacgcccgcctcgtccgcctcatgtacgtcgcgcac
gagaagcgctggatcgacccgtcgctccgcaacctcgtcggcgactggatccgccgtgttgaggagcgtctctcgaacgtca
acgactcgggcatcaagatctcggcactccagtcgtactcggagctgaacgagcctgaggcgttcctcaagcagttcctcgcc
cagtacccgcaggccgaggaccagatcctcgcctccgccgacgtttcctacttcctcgccatctctcaacgccccggacaga
agcccgtcccccttcatccccgtcctcgacgccaacttcagcatctggttcaagaaggactcgctgtggcaggccgaggacatc
gaggccgtcttttgaccaggacccgcagcgtgtctgcatcctccagggaccggtcgccgccaagcactgcacctcgacgcag
acgcccatcgccgagatgctcggcaacatcgagcaccagctcgtcaagaacgtcctggacgactactacggcggcgacga
gtcccagatcccgactatcgactacctcgcgccccctcccaagccggtcgacgccggcgctatcctcgccgagaacaacatc
gcgcactcggtcgaggagctcgccgacggcggcaagaagcatgtctactcgatcaacggtgtcctcccgccgacgggcga

FIG. 10 ctggcatgccgcactcgccggccccaagctcgactggctccaggcgttcctctccaacgtctcgattcaggcgggcgagcag
tcgattcctaaccccgtcaagaaggtgctggcgccgaggcacgggcagcgggtcgagctcaccctgaacaaggacggcca
gccccctcaagctcgacgtcttcggcgggctctga

SEQ ID NO2:
>RtFAS2
atggtcgcggcgcaggacttgccgctcgcgctgagcatcagcttcgcgcccgagtcgtcgaccatctcgatgacgctgttcaa
ccagcccgaggcgtcgaaacccgccctccccctcgagctcaagtacaagtacgacccctcgacgccgtacgccccgatcca
cgagatcaccgaggaccgtaatcagaggatcaagcagcactactgggacctctggggcctcggcaacaaggcagaccagg
gcatctcgcagctcaagatcaccgacgagttccagggcgacctcgtcaccatctcggccgacgagatcgaggcgttctgccg
tgttgtcggcatcgagggcgaggcgtacaagcgcaaccacaaggccggcatgcaggtcccgctcgacttcgccatcaagct
cggctggaaggccatcatgaagccgatcttcccctcgacgattgacggcgacctgctcaagctcgtccacctctcgaacggct
tccgcgtcctccccgacacgcccacactccaggttggcgacgtcgtgacgaccacgtcgcgcatcgaatcaatcacgaactc
ggacacgggcaaaaccgtctcggttcgcggcgtcatctcgctcgtctcgtccgccgactcgaagggcaaggacgcctcgac
cgaggaccgcatcccgctcatcgaggtcacctcgtccttcttctaccgcggcaagttcagcgactacgcccagacattctccc
gcgtcgcccacccgacctactctgtcccgatcaccacgcccgaggccgtcgccgtcctccagtccaaggagtggttccagtg
ggacgacgactcgaagcccctcgaggtcggcaccaagctccagttcaaggtcgagtcgaactatgtctacgccgacaagtc
gtcctacgcgatggctaccgtcaccggcggcgcgtacgtcatcacccccgagctcaagctcgctgtcaaggttgccacggtc
gactacacgtccgagggcgagggcgtcatccagggcgacccggtcatcgagtacctcaagcgccacggctcggccctcga
ccagcccatcatgctcgagaacggcggctattcgctcaccaaggccggccagtgcaccttcacgacgcccgcgtccaacct
cgactactcgctcacctcgggcgacacgaacccgattcacacgaacccgtactttgcctcgctcgcctacctccccggcacca
tcacgcacggcatgcactcgtcggcccgcacgcgcaagtttgtcgagcaggtcgccgcagacaacgtcggcgcgcgcgtc
cgcaagtacgaggtcggcttcacggccatgtgcctcccctcgcgcaagatggaggtccgccttaagcacgtcggcatgacc
gcggacggaaaccgcctcatcaaggtcgagaccgtcgacgtcgagggcggcaacgtcgttctcagcggaaccgccgaggt
cgcccaggctcccaccgcgtacgtcttcaccggtcaaggttcgcaagagcccggcatgggcatggagctctacgccaactc
gcccgtcgcccgcgccgtctgggacgaggctgaccgccacctcggcgaggtctacgcttctccatcctcgagattgtccgt
acgaaccccaaggaaaagactgtgcacttcggcggggttgaaaggccaagcaacccgtcagaagtacatggacatgtcgtac
acaacgactgaccatgagggcaacgttaagactctcccgctcttcggcgacatcgacctccgtacctcacgctacacgttctcg
tcgccgaccggtctcctctacgccacccagttcgcccagatcgccctcgtcgtaacggagaaggccgccttcgaggacatgc
gcgccaagggtctcgttcagaaggactgcgtctttgccggtcactcgctcggagagtactcggctctcgcctcgatcgccgac
atcctccccatctcggccctcgtcgacgtcgtcttctaccgcgggtatcaccatgcagcgcgccgtcgaacgcgaccacctcaa
ccgctcgtcgtacggaatggtcgccgtcaacccgagccgcatcggcaagagctttggcgacgccgccctccgcgaggtcgt
cgacaccatcgcccgccgcggaaacatcctcatcgaggtcgtcaactacaacgtcgagggacagcaatacgtcgtcgccgg
tcacctcgtcgccctccaatccctcacaaacgtcctcaacttcctcaagatccagaagatcgacctcgccaagctcaccgagac
gatgtcgatcgagcaggtcaaggagcacctgtgcgagatcgtcgacgagtgcgtccagaaggcgcgcgacctccaggcca
agacgggcttcatcaccctcgagcgcggctttgcgacgatcccgctccccggtatcgacgtgccgttccactcgcgctacctc
tgggcgggagtcatgccgttccgcacttacctctcgaagaaggtcaacccggcgcacttcaacgccgacctcctcgtcggcc
gctacatccccaacttgaccgccgtccactacgaggtctcgaaggagtacgccgaacgcatccacacccagacgtcgtcgcc
gcgcctcaacaagattctcaaggcctgggacgaggagcgctggggcgcacccgagaaccgcaacaagctcggctacgcc
atcctcatcgagctcctcgcgtaccagttcgcctcgcccgtccgctggatcgagacgcaggacatcctcttccgcgacttcaag
tttgagcgcctcgtcgagcttggcccgtcgccactctcaccggcatggctacgcgcacgcagaagctcaagtacgacgcgc
acgactcgtcggtcggcatcaagcgctcgatctactgcatcgccaagcaccagaaggagatctactaccagttcgatgacgtt
gccggcgaagaggcgcccgctcctgccgcagttgcgccttccgctcccgctcccaaggccgccccagtcgccgccgcccc
tccccctcccgctcctgtcgctgccgcgcctgccgccgccgtcgccgacgagccgctcaaggctgtcgacacgctccgcatc
atcatcgcgcagaagctcaagaagcccgttggcgaagtccccctcaccaagtcgatcaaggagctcgtcggcggcaagtcg
acccctccagaacgagattctcggcgaccttcaaggcgagttcagcagcgcgcctgaaaagggcgaggagatgcctctccag gagctcggcgcggccctccagcagggctactctggcaagctcggcaagtacaccaccggcgtcatctcgcgcatgattggc
gccaagatgcccggcggttttggtctctccgccgtccagggtcacctcggcaagacctacggcctcggcgccggtcgcatcg
atggcgtcctcctcttcgccgtcacgcaggagccggctaagcgtctcgccaacgagggtgaggcgaaggcttgggtcgact
cggtcgcgcaaggctacgcctcgatggctggcatctcgctcgccgccggcggtggagctgctgctgctgccccgcgatgg
cgttcgccgctccggccgcagctggcggtggagcgcccgctgccgtccccgacgagccgctcaaggcgaccgacacgctt
cgcgccatcatcgctcagaagctcaagaagcagatccccgacgtcccctcaccaagtccatcaaggaccttgtcggcggca
agtcgaccctgcagaacgagatcctcggcgacctccagggcgagttcagcagtgcgcccgagaagggcgaggagatgcc
gctccaggagcttggcgccgcactcaaccaaggctactcgggcacgctcggcaagcacacgagcggtctcgtcgcccgca
tgatgggcgccaagatgcccggtggcttcggtctctcggcggcgaaggcgcacctctcgaaggctcacggtctcgggcccg
gccgcaccgacggcgctctcctcgtcgcgctcaccaaggagcccgagaaacgtctcggtagcgaggccgacgccaaggc
ctggctcgacggcgtcgctcaggcgtacgcctcgcaggctggcatcaccctcggcgctggtggaggcggaggcggcgcg
gctgtcggcggcgccggctttatgatcaacaccgagcagctcgacaagatgcaggagaagcaggacaacttcgtctcgcag
caggtcgagctcttcctccgctacctcggcaaggactcgcgcgagggccaccgcctcgccgacatgcagaaggcagaggt
cgccaacctccaggagaagctcgactcgatcgctcgcgagcacggcgacgcctatgtccagggcatccagcccgtcttcga
cccgctcaaggcccgccacttcaactcgtcgtggaactgggtccgtcaggacgcgctcatgatgtggatggacatcctcttcg
gccgcctcaccaccgtcgaccgcgacatcaccgctcgctgccttgtcatcatgaaccgcgccgacccttctctcatcgactac
atgcagtacaccatcgacaacaccccgtcgagcgcggcgagcattacgtcctcgccaagcaattcggccagcagctcctc
gacaactgccgcgagatgatcggccaggctccgctctacaaggacgtcaccttcccgaccgcgcccaagacgaccgtcaac
gccaagggcgacatcatcaccgaggaggtcaaccgccccggcgtctctcgcctcgagaagtatgtcgccgagatggctgcc
ggctcaaaggtcaccgtcgccagcgtcaacctcgacaaggtccaggagcaggtcgagaagctgtacaagctcgtcaagtcg
cagccgcagatttcgaagcagcacatgacgtcgatcaagtcgctgtacgctgaggtcgttcgcggtctcggcaaggacgccg
gccctcctccggtccacaaggccggcactcgcgcccgccgccctcgagccagttcctccgtcccgcagccgtctccgagg
cgactttcctccccgaggacaaggtgcctctcctgcacctcaagcgcaagatcggcaacgactggcaatactcgagcaagct
cacgtcgctctacctcgacatcctcaaggagattgccacgtcgggtgtcaccttcgagcacaagaacgcgctcatgaccggtg
tcggcaagggctccatcggtatcgagatcgtcaagggtctcctcgctggtggcgctcgcgtcgtcatcacgacctcgcgctac
tcgcgctcgactgtcgagtactaccaggcgatctaccaggaggtcggctcgaagggctcgtcgctcaccgtcgtccccttcaa
ccagggctcgaagcaggatgtcgaggcgctcgtcgacttcatttattcgaaggataagggtctcggcatggacctcgactaca
tcctcccccttcgccgcccttcccgagaacggccgcgagatcgacggcatcgacgaccgctccgagctcgccccaccgcatca
tgctcaccaacctcctccgcctcctcggtgccgtcaagtcgaagaaggccgccctcaagctcacgacccgcccaaccgaggt
cgtcctcccgctttcgccgaaccacggcctcttcggcaacgacggtctctactcggagtcgaagatctcgctcgagacgctctt
caaccgctggagctcggagagctggggcgagtacctctgcctcgctggcgctgtcatcggatggacgcgcggtaccggtct
catgtcggcgacgaactcggtcgccgaaggtatcgaggcgcagggttgcaggacgttctccgccaaggagatggccttcaa
cattctcggcctcatgcacccgctcgtcttcgacgtcgcgcagatcgagcctgtctgggccgacctcaacggtggcatggaca
agctcccccgaccttgccaacctcacgaccgagatccgcaagaagctcaacctcaccgcgtcgacccgccgcgccatcgcca
aggacaactcgttcgactacaaggtcgcgcacggcccggcgatggagcagatacaccagcggatcaacgtcgcccgcgc
gccaacttctccttcccttccccgagctcaagccgatcgatgccaagtcggagctcgcgaagctccgtggcctcatcgacct
cgagaaggtcgtagtcatgaccggttacgccgaggtcggaccgttcggctcgtcgcgcacgcgctgggagatggaggcga
acggcaccttctccatccagggcacactcgagcttgcgtacgtcatgggcctcatcaagcactttgagggtcgcctcaaggac
ggcacgctctacgtcggatgggtcgacgccaagacgaacgaaccgctggacgacaaggacgtcaaggctgcgtacgaga
agcacattctcgcgcacaccggcatccgcctcatcgagccggagatcttcaacggctacgacccgaagcgcaagggcttca
cgcaggagatcgagatccagcacgacctcgagcccatcgaggcgtccgaggaggacgcggctcgcttcaagcgcgagca
cggcgcgctcgtcgacgtctacaccgaggacggcagcaagttcttcgtcaagttcaagaagggcgccaagctgcacattccc
aaggctgttgccttcgaccgccttgtcgccggacagatcccgactggctggtcgcacaaggccttcggtatccccgacgacat
tgcctcgcaggttgaccgcaccctcgctgtgggcgctcgtctcggtcgccgaggcgctcatgatggccggcatcaccgacccg
tatgagctctacaagtggattcacccgagcgaggtcggttcgtcgctcggatccggcatgggaggcatcacgagtatctcgaa
gatgttccgcgaccgccgcgaggagaaggacgtccagaaggacatcctccaggagaccttcatcaatacggtcgccggatg ggtcaacctcctccttctctcgtcatccggaccgatcaagatccccgtcggcgcctgcgcgactgccctccagtcggtcgagat
cgcctgcgacaccatcctcagcggcaaggccaagatcatggtctcgggaggctacgacgacttctccgaggagggctcgta
cgagttcgcaaacatgaaggcgacctcgaacagcgagaccgagttcgctgccggccgcgagccgaacgagatgtcgcgtc
cgacgaccagcacccgtgccggcttcatggagtcgatgggttgcggtgctcaggtcctgatgtcggcgaagacggccatcg
agatgggcgccaccatctacggcatcgtcgcctacaccgcgaccgccaccgacaaggctggtcgctcgattccgcccccg
gacgcggtgtcatgggtaccgcgcgcgagatcacctccaagtaccctcgcccatcctcgatgtcacctaccgccgccgcca
gctcgagttccgtcgcaagcagatctcgcagtggctcgagaacgagaccgagctcctcaagttcgaggtctcctcgcacgga
caggccacaaagctccccgacgactacgtctccgagcgcctcgcatccatcgaacgcgaagccaagcgccaggaggccg
aggctctcgcgacgtacggcatgctcgccggccaggacccgaccatcgccccgctccgtcgcgctctcgccgtttggggtct
caccatcgacgacgttggagtcgcctcgttccacggcacctcgaccgttgccaacgacaagaacgagtcgaacgcgtacaa
cgagcagttccgtcaccttggccgcgccaagggtaacgcctgccccgtcatcgctcagaagtggctcaccggacacccgaa
gggaggtgccgccgcctggatgctcaacggcttggcccaggtcattcagagcggtctcgttcccggcaaccgcaacgccga
caacatcggcgaagagcttcgcgcgttcgagtacctgctctaccgtccaagtcgatccagaccgacggcatcaaggctggt
ctcctcacctcgttcggcttcggtcaagtcggtggccaggctctcatcgttcacccgagtctgctcatcggcgcgctcgagccc
gcccagttcgaggcgtacaagaagctcaacgaccagcgcaagaagtggtcataccgtcgcttcaacgatttcttcacgaacg
gcaagctcgtcattatcaaggacggcacgcccttcacgcccgagcaggagaacacgaccctcctcaacccgctcgtccgcg
ccgtgcccgacaagactggctcgtactcgatgccgaaggagttccctgccaccgtccctcgcagcaacaacgccgaagtcg
ccaacaagctcgtcagcgcggctgtcggcggtgctttcggcgtcggcacggacgtcgagctgatcagcgccgtcccgacct
cggagtcgttcctcgagaggaacttcacccaggacgagatcgcctactgcaaggccgcacccgacttccgcgctagcctcg
ccgcgcgctggtccgccaaggaggccactttcaaggctctcaagaccgagtcgaagggcgccgccgccagcatgcagga
catcgaggtcgtctccacgtcgcagggcccgactataagctccacggcgaggtcgagaagatcgcccaggccgccggca
tcacggccttcgaggtctcgctctcgcactcggaggacgtcgcttgcgccgtcgtcatcgcccagaagtag

SEQ ID NO 3:
>AkFAS
atggaacaacataaaactgagaaactttcagcagccgatgaaaagttgagtgagagtacaattcattggcttgctgcaacagat
gtcccttcaaactttgtactcttttccggacaagggtatcaatactttgatgagctccgggaactgtatgaaactggcacagatga
ggttaaaaggcttccttttacttgcttcgaaaacactgcaggaagagatctgtagtgaaaaagcgaaaactgtcgctttcaaatttgt
caatgagcttgactttacgaaatggatagaagaggatatcgatgtggatcaaacctacatctttctgctccagtttctttcccctta
atatttgtcgctcaagttgcaaggtacttgcaaactttaaacttgctaagaacagaccacaaacaatttatccagacaattaaagg
gtctagtggtcatagtcaagggattgttgctgctgtattgatatctacatcgcctgacaacgacagaattgttgagaatgcagtca
actttgcagatatatgttatggcaagggctgagatgccatgaaagcagtgtaaacagattcagtggcaaaaaccacaaatcga
aaaagtctaaagtttattcctttgatgaatcgacccgcatggtaaagtattctcccatgcttgctgtcaatggtctcacggaatccct
cctcaacgatttatgaagaaaactgaatccattattgaagcaagaagaacgatacaacaaaagtataaccgaagagaatcattt
tttgaaacaccaacagaaaaggatgagaaaagtaaaagacttaatatgtttcaaattgcacttgcgaatggccccaagtcatttgt
tgtctctggagcgccaaaaacacttattgagctagaacaaagaataaaggagtcaactacatcgtctccaaactctcaaacacg
tataccatttagcaagcgcaagccagttgttaaaatgtatttcctcaaggttggggctgcttttcatactgaaatttgtaatgacgcc
tctagtaaactaaaagccgatgtggtccaaatgaaattgagtatctcgccaaaggaaatattaattcctgtctaccatacaaaaga
tggttcgaatttatcggagatctcagcagatgtgaatgttgtcgatttgctaattgatatgcaaactagtcaagtcaatgatttcaga
aaaaccttgaagagtatttcaagtcagaatgggtgtcaaacgttattgattttggtccaggtgacggaactgctaaattgtgcct
gaaacgaaagtctggaactggtatactagttgtcgcggctactggaccactacgaaacagaagatgtgcatatggtagaaatct
tgtcggtctaaactctgttttgctggaaaaaaatcctatactagggatgaattgggggggaagaatttaagcccagactgtcgagt
cgcaagaatgacaaccaaatcattgtcggaactagatttagtgacttgactggaaagccgcctgtaattctacctggaatgacg
cctactacatccttcacggcatcgatttggttgccgcctgtagtaatggtgggtatcatggcgaacttgctggtggtggattgcc
actgccagaatacttcaaagcgaaaattgatgagctagtgagcaagcaaaactctggagtaggcataaacataaacatgcttta
cctaaactcctacttatggggttttcaattttccactgccattcagatggcgaaagatggatatcccatagaatctatcacttgcgcc gccggagttccaactactgaaaaagcgaaagaaataatgcatcagttgaaagaagctggaattaaatacattgccttcaaacct
ggatcaagagccgcaattatggatgtattatctattgctagagaaaaccccaatagttcaatcgtactgcaatggacaggagga
cgtggaggtggacatcactccttcgaagactttcatgctcctttgctcgacacttatcaagaaattagagaacacccaaacgttgt
tctcgtcgtaggctccggatttggagatgcagagaagtcatacccatatttagatggttcgtggtctacattgcctccacataact
gtgaatcgagaatgccatgtgatgcagtttatttggatctaggtgcatggttgcaaaagaagctgctacctctccagaagttaag
caattgattgttaacgctaagggcgtccgagaaaacgaatcttgggaaatgtcttacgaaaacgatgctggtggaattctcactg
taacttccgaactcggcgagcctatccataagataaacaaccgcgggatgaagctatggagagagtttgacagaaagtacttct
cattaccttcgggccaagaaagggaaaaggctatagtgaaagataaaaaggagataattagaaggattaatgcagattttcaaa
aagtttactttggaaggaaggccgatggaactgttgtggacattgcatatatgacatatggtgaaattttacggagaatggtgga
cctaatgtacgtaaccggaggaggagatggaaaacaacatagatttgcgccaaacagatggatagacgttacgtaccaaact
agaacgttcaagttttagttcgcacagaaagacggttttttgagagacaaaaaaatggcctttgcaactgatatgagaaaactcg
aatcttttccgataaagtgcattgatgagttcgtcaagtgctaccctcaagtagataaagtgctggtatcggacgaagatgctgga
tattttatcgaactttgtcgaaaccttagaaacggaaaaccggtaaattttattcctcaaattgatggctctttagcttactggttcaaa
aaagactctctctggtgttctgaacagattgacgcggttcccgacaatgaccctggcagagtttgcatactacatggcccagtag
cagcgcaatattcagtagtgtcagatgagcccatatgcgaaatcctcggtaacattcacaagggatacgtggacaagttgaaa
gaggagaagtatgaggtggccaaagttgaaacaatcggaaagctacctgaatacaaaggttccaacaagtctttccgcaaattt
cttcgttatggttggttcaatgccctgtttcaaagtaccgtaatggtcaaggagaaaaagtgggtcagaaacattattccaggaat
catacaaacggaaaacgaaaacattgtattctcagagcgaacagcaatgaatgatatgtgtctcatcgaagttctttaaatgatt
cacagagaactctagctttcatagagtttgaaggaaagcacatttctgtgtctttgcaggattctgaacctgtaaacagcacactg
accctgtattttgagtaccatcctgaaactcctcactctccgttatttcaagtcacaaatggaagcaaaagtattgctagatcaatca
aacagtattacaggaatatatgggattgtcaggatgttgtttctatccatgatacattttccgaaagcttcaccgtcacgagagaag
acatcgaaaggttcaatggcgcaattcaatatgcggtaaatacttcggagggaactttagactttgcaattgttgcaggatggaa
atcactgataaaagctctgttttcaaaagagatagacggcagtctgttagatcttgttcacatctcccactcatacaaactacttgta
gaggagaaggagagaacgcttgttcaagctggagagaaaatttgttcggaatctcgcgttatttcagtacagatattaccaggt
gttggaaaaagtataacagttaaaggggtactctctagaaacacagtcaaatgggttgaagtccaatccgagttttttaatccgag
gcaatttcttcgattttcaaaagactttcaaggaatatagctacaaagctgaggttttatgtaaagacgatacagttccgcaaatcct
aaactcacaggaatggcttttctggactctggagtcagacctctatctaaacacgataaagttgtatttcaaatcgatcgcgttgt
ggaaaagagaaagtctgtgacaaatatttctgatattttagttgctggtaatgttgttcgaatcaatacacctgaagagatcgatgg
ttttattgaattgaaagaccaaggaagcccaaagggaatcatcattgggaaagttgatttaagccttgaaaatgccaatctgagt
gaaaatccaattattacatatttggattccattaaagaatcaaaattgcacggtagtgttttttgaatcgggaggatatactgtgatgc
cgaggcccgaactagtaacagcgccaagtattgtcgaaagcattgtgtatgcatctgcttctagagatatgaatccaattcatcg
gaatcgcacattcgctaagttagctggactccccggtggtagtaccattgtgcacggaatgtggacagctgcaatgagcagaa
gaattctagaattacatacagttctcggagaccatcgccgtatttccacatactcggttaaatttaccggcatggtgttcccagaag
acaaactagccgttatggtcaaacacgttggtgttacggaaggtagacttattcttgatgtagatgttagcaaagtagaaacgca
agagcgggttctccacggacgagctgaagtagaagggccgtcgacatcattcctattcactggtcaaggatccgcaaagttg
ggatgggaatggacagctacgaagaaaagcagtcggcacgggcagtttggcaaactgcagataaattttttgaggaaaaattt
ggattttcaattgttgatattgtcaaaaataatccaaaagagttgactgttcgtttcggtggatcacaagggaaagtgattcgagaa
aactacagagccattaaaagggaagatggatctcaattgatccgagaaatccatagtaataccacgtcatttacatttcgttcacc
aaatgggctttatttgccacgcaattttctcagccggcgctggtactagtgcaaaaagcagcgtttgaagaaatgcttcaagga
ggtttgttccgtcaaacagtatgtttgctggtcattctcttggtgaatacgcagctcttgcctcgtatgcaaacgttctgagtatcg
aagacttagttgaaactgtattttaagaggaatggtaatgcaaaatgcagttgcaagggacgacgaaggaacatctgattacg
gtatggtggctgccaatccttcaagagtcagtaaaacgttctcggcacaattgttgatggaaatcgtccagaaaattgacgacga
atcagatgacagtcatcttctccaagtagtaaatttcaatattagagatgctcagtacgtaatagctggaaatctggaattgttagat
agtctatcgaatgttctcaatgtaatttcaaacagccacgacaaaaccttttgacagaagcattatccaagctgcaatgataaagg
ctgaaaataggagaagaagctgcaaggaaaacaatcaaccttccgtcttaagcgtggaatcgcaaccattcctcttcacggca
ttgatgtaccttttcattctcgacagcttttgaatgggtacctgcttttcggtctctactagaaccaagatttacggaagaaatgatt FIG. 10 (Continued)

caaaagtacttgcctaggttgatcggaaagtacattcctaatgtgcacgcagaaccgttttccattagcaaagagtacattgaaa
aggttgcaagtgtaacaaaatcgccagcgttgtacaagcttctatctacatactcaacaatgtgtgactcatcaaaagcaagaat
cttgctcatagagcttttagctcatcaatttgcaatgccagttcaatggatagatacccaggactatatactctccaggcacacaca
gcgaataattgagatgggcccagccccaactcttgttggtatggcgaaaaagacattgcaatctagaatatatggtgacgaaga
agactacaaacctagtattctgtggtggaatcaaaaccaggaggaaatcttctataacttggacaatcaaggaatatctattcaac
agtttttgcaagaattaaaaggaactgaagatgacgagtcacagtctgatgatatgtcatcatatacccagtcagacgagactat
acaaagaactgcaaagaacagggttatgccagaagcaaatgcaaacgacaaggagaaagtggggaatgaacttcaaaaga
aggaagttacaaacaggcctcttcatgtcctaagagtcctcatctcaaccaaacttaagaagaaaatgttggaggtaaaggcaa
cagacaccatcaagggtgtttctggtggaaaaagtgcgattcaaaatgagctaattggagaaataaacgctgaatacagcagtt
ttagagatattgaagatatttcggaagtttctttagctgagctagctagaagggccccatcccggcaggaaacagttcttggtaaa
gttacaacgaaaatggtgaacaaaatgttttctagcaaactgcccggaaatttggtcctaatgatactaaggagtacttacaaa
gcaaactctcggatgcgtccacagtcgattcagtgtctcttcatgccctgactctgcagccggtttctagactagctacccctgga
gaggcacaggcatggcttgattctgtttgtagagactttgaaaacgatcagagaatcagtattctaaagaacaaaagtccaaatt
cgaacgaaagtgtgatgatttctgaacaaaggactgttcaaaacaactttgtacaaatttctgaagaaccagtaaacagcaaaca
tgtattgttgtccctgatatctatgaagctacagaaggaaatctcctcaatcaatgaaacatcaacaataaagagcttggtgaatg
ggaagagtgcagttcaaaacgaaattcttggagaaattgcttccgagtttcggacagacgaatctgaaggagctgcagatattt
cgctctccgagcttggagaaaagcttggaattgggtatgcaggacctggcagtgttgtttccaggcacataaataaaatgttaaa
ctccaagcttccagggtcatttaattcttcatcagccaagaagtatcttcgatgcaaggctttggaaaaggacgaagtgactccg
tactggttcatgctttgacaatgcaaccaaaatcgcgcctgcagggagtcgaagatgcaaagtcttggttggattcggtttgttcg
agttatgggaaatgggcaaatattgatctcacagtttctcgtactctctcttcaggtgatagtagtcctgctcattcgacaaaagata
tcctttcgtccactgcaatgaagaaattgaaaaaattgtacttggaccaggtggatgtcttcaacactttttgggagaggatcgac
gggccaaacttcaaaaggttctaacagaggaaaccagtgcaaaagatagaatagaggctcagctccttgaattaaaggaaga
acttggagaccctttttgtgacgggatacaaccccagtttaatgaagctcggatacgaatctatgattcatactggaactgggtgg
tgcaggatgcattagaactccattatcatacattctcttgtgtgttgaactcaaaaggcaagaacgtaaatattcccaattcatctaa
cagctattttcgcgcaatgagcgactggataacttcttcaaacgaaaagttggaagaaaataaacctccgcaggcttggtttcgc
aattacctttgtaatcgtgccactccagaacttctaaccgttgtacaatactttgcagcaagaatgaacgaacaaggacattcaga
atatgctcaagcagtatctcttttagcagaacaagtatcacagtggatatctagaccacctgtacacatagcattgtttgcatctcta
gaacctaggggtgacagttgatagtgctaacaattttggattgaaatatgaagaaaaaccaagaaagtttgtggctgtcggtgaaa
acaaagctttctcgtgtgataatgcgtccctgtatgttaaagaaatgagcaaggggctattttatgaccaccgtgtggcttcgaaa
gttgaacatcccagccaaagtgtatacctttctcccgataattctttcttccaaacgaggaagagagtgaccagatttcaagcgg
aatgagactaccaaaaacacaaggagaaatccagcgtgattttttcaagactccctgctggtcagaagctagaagtcatgagaa
agagtgttaatcggtcgtccgacacagatgaggaaattgccaacatcgttcgacaaaactataacagtatccatgtggcaaaaa
acgtacctttggtgcatttgaaatcgccttctaaatttgacaagacggtaagagtactcgatgagcctttgacatcaatgtacttga
gttgtttgcatgatattgcaacaagtggagttagctttgcaggacaaaacgctttggtgacaggagccggctttggttctattggg
attgaattaatcaaaccgttgcttgaggggggggcaacggttttagtaacagttagacttaatcggactgacgagcaaatgcaa
attgttaatgaaaggtttcaaagattgtacgaagagtttgggtccagaggaagcaagctcgttctggttccttgcaattgcgcttca
aatcaagatgtacattccctcattagacacatctatgagaaattgaaacttgacctagattttatatttccatttgctgctatcgggga
gcaagggaaagatgtgtctgaaattggctccaaatctgaagtcgctcatagactaatgctgactaatactataagattactaggt
gcagtgaaaaaggccaaagaggatagatgcattgaaacaaggcctgcactggttctgttgccatgctctccaaaccatgggg
attttggactagatgggttatatgcagaatcaaagcttggattggaatccctagtaaacaagtggaaaagtgaagaatggggaa
attacctaagtatttgcgctgcagtcataggttggacaaggtccaaactcatgtggcagaacaatgtcgttgccgagggaatag
aaaagttgggagtgagaaccttttctactacagagactgcttttaacctgattggtctactacatcctgatatcgtgtctcatgcagc
agaagaacctctatgggcagaccttactggaaactggggcgctgctcctgacttgaaggaacattcaaaaaggattcgaacgt
cacttctggcacaaagtaaagcagcaaaagcccatatcgctgtcgtcaaaatcgctcgttatagaaccttctgaatccaagacga
aagcgcagacagaaattgttaacacatacctagctggtgtgaatgataagttgaggcttccgctagcaaatcccgaaaagttct
gcaatccattccctaaaattccatcccaggaacgaatggattcattagcataccttaaacactcagtagatctcaaaaaagtcgta gtagtagtaggatatggagaaattgggccttggggaaattcgcgcactagatggggagatggagtcattcggtgaattctcgctt
gaaggtgcaatcgaacttgcttggctcgttggcttaatcaaaccagttactggaccgttaaaaaatgatcctagaacgcaatactt
tggttgggtagatgcagaatcagaagagccagttgcagatcatgaaataaagactcgatatgagaaagtactgcttcagcactc
tgggattcgtcttattgaaccggagctctttgaaggatataatccaaagaaaaagtcaattctgagacaagtagccatcgctgaa
gacatgaaaccaatagaagtagcttctttggaagaagcccagcagtacgtgaatgagttagggaaagagttcatagacgttttt
aatgaaaacgttgaatctaatgatggacaatggtatattcgcctaaaagcaggagcagtggtctccattcctggagcgttaagct
tcaacagatttattgctggtcagctacctacaggatgggatgcaaaacgactaggaataccagatgatattgccgactctgtaga
tcctgttacgctatatgctctggtttcaacagttgaagccttggtgtgtgctggattgacagatccatatgaactgtatcaatatgtg
catgtaagtcaagttggaaacacgtcaggtggcggcatgggagggatgcgatcattgaagcgaatgttcctagaaagaaaac
ttgatgcagaaatcccttctgatactttagcagagtcatttattaacacaatgccagcctgggtgaacatgctgcttctgtcaagct
cgggaccaataaagactccagtcggtgcttgcgccacagcggcagagtcggtagacataggaattgaaaccatcttagcagg
aaaagccagagtcgttatagcgggcgggtatgatgacttttgtgaaacgggaagtaatgagtttgccatgatgggagcaacttc
caacagtcaaacagaagctgaaaaaggcagatttccacgtgaggcatcaagaccaatgacagatacacgtgccggattcatg
gaatcacaaggcgctggtatgcaagtgttaatggatgctgaattagccattcagatggggcttccagtatatggtattcttgctct
gtcaaacactgctaccgatagacaaggaagatccgtgcccgccccaggtcgtggaatactaaccactgcgagagaagtgcg
ctcaaaaaactctaaaagtagccacaacggcaaaccagtagaaaatcctctattgtctgtaaagttccgcaaaaaacatttgaga
caagagctcgatgctatagatctgtgggccagccaagagatatcgaacatgtctgaggaattctcacagaattcaagaaaatg
gaaaacaggaaaggttttgtagaaacaatgcgaaaaaagaagcgttcggcagcttttgaaacctggggacaaggattctatag
gaatgatgactccatagcccctttacgcggagctttgtccgtatggggattaacagttgatgatcttcttgtgggaagttttcacgg
aactggaaccaatcttaacgatacgaatgagtcctccttagtgaataagcagcttaagcatttggatcgaaaagaaggaaacatt
ctgttagtagtaactcaaaaatatctgactggtcatccaaagggtgcagctgctgcctggatgctcaatggattgctgcaatgcat
gaattctggaagagtaccgggaaaccgaaacttggacaatgtagatggaaagctcagaacaacggttacttgttctatccaa
atcggacaattgaggttccaagagtggaagcagcttttcttaaaagctttggatttggtcaagccggagctgaagttgtcattattc
atcctgatcgtctcctggctgtttaagtgaagaaaatctgaaatcgtatatacttcgaagaaatgaaagagagaaaagagcatat
cgatatcatcaaggcgtaatgagtggacatcatactatggtgcaagtgaaggaatttgctccatatgaagacgatatcctagaag
aaatatatttgaatccaagagctagggcttcctttgactcatcgaaaagtacttggacgtttcacaaatataggaacgacaaagat
actgtagacgataaagatgaaatggagcaagattcattgaatgaatcagtagatcttccgaaagatattacaaaagttggatcac
cctctgaaatacgtattccagtaaaaacaagattggaagttactgttcgtgaaggagtcgaaggtttgacgaaaaaggacaagtt
ttcaagtcaaggggttggcgttgatgttgaaccagtttcaacttttgcacaacatgaagagaaaacgatctttattcagaacaactt
cactgagaatgaacagctgtattgtaatcatgctgcaagtccagcagcaagctatgcgggtagatgggcagcgaaggaagca
gtgattaaagccatcagcaattcttcacttgaaacaagatcactttggcaaggagctgagggtaaactgatcgacattgaaatca
ttcaaagtaattctggtgctcctgaggtagtcttgcatggtcatgcaaaagaagtattccaaactttaggtcttacaaatgttaaggt
ttctatcagtcatactccagaagttgcagtagcccaagcaataacaaattaa

SEQ ID NO. 4:
>ScFAS2
atgaagccggaagttgagcaagaattagctcatattttgctaactgaattgttagcttatcaatttgcctctcctgtgagatggattg
aaactcaagatgttttttgaaggattttaacactgaaagggttgttgaaatcggtccttctccaactttggctgggatggctcaaag
aaccttgaagaataaatacgaatcttacgatgctgctctgtctttacatagagaaatcttatgctattcgaaggatgccaaagagat
ttattataccccagatccatccgaactagctgcaaaggaagagcccgctaaggaagaagctcctgctccaactccagctgcta
gtgctcctgctcctgcagcagcagcccccagctcccgtcgcggcagcagcccagctgcagcagctgctgagattgccgatg
aacctgtcaaggcttccctattgttgcacgttttggttgctcacaagttgaagaagtcgttagattccattccaatgtccaagacaat
caaagacttggtcggtggtaaatctacagtccaaaatgaaattttgggtgatttaggtaaagaatttggtactactcctgaaaaac
cagaagaaactccattagaagaattggcagaaactttccaagataccttctctggagcattgggtaagcaatcttcctcgttattat
caagattaatctcatctaagatgcctggtggtttactattactgtcgctagaaaatacttacaaactcgctggggactaccatctg FIG. 10 (Continued)

gtagacaagatggtgtccttttggtagctttatctaacgagcctgctgctcgtctaggttctgaagctgatgccaaggctttcttgg
actccatggctcaaaaatacgcttccattgttggtgttgacttatcatcagctgctagcgctagtggtgctgccggtgcaggtgct
gctgccggtgcagctatgatcgatgctggcgctctggaagaaataaccaaagaccacaaggttttggcgcgtcaacaactgc
aagtattggctcgttatctaaaaatggacttggataacggtgaaagaaagttcttgaaagaaaaggacactgttgctgaacttca
agctcagttggattacttgaatgccgaattaggtgaattctttgttaacggtgttgctacttctttctctagaaaaaaggccagaacc
ttcgattcttcctggaactgggctaaacaatctttattatcattatactttgagataattcatggtgtcttgaaaaacgttgatagagag
gttgttagtgaagctatcaatatcatgaacagatctaacgatgctttgattaaattcatggaataccatatctctaacactgatgaaa
caaaaggtgaaaactatcaattggttaaaactcttggtgagcagttgattgaaaactgtaaacaagttttggatgttgatccagttt
acaaagatgttgctaagcctaccggtccaaaaactgctattgacaagaacggtaacattacatactcagaagagccaagagaa
aaggttaggaaattatctcaatacgtacaagaaatggcccttggtggtccaatcaccaaagaatctcaacctactattgaagagg
atttgactcgtgtttacaaggcaatcagtgctcaagctgataaacaagatatttccagctccaccagggttgaatttgaaaaactat
atagtgatttgatgaagttcttggaaagctccaaagaaatcgatccttctcaaacaacccaattggccggtatggatgttgaggat
gctttggacaaagattccaccaaagaagttgcttctttgccaaacaaatctaccatttctaagacggtatcttcaactattccaaga
gaaactattccgttcttacatttgagaaagaagactcctgccggagattggaaatatgaccgccaattgtcttctctttcttagatg
gtttagaaaaggctgccttcaacggtgtcaccttcaaggacaaatacgtcttgatcactggtgctggtaagggttctattggtgct
gaagtcttgcaaggtttgttacaaggtggtgctaaggttgttgttaccacctctcgtttctctaagcaagttacagactactaccaat
ccatttacgccaaatatggtgctaaggttctactttgattgttgttccattcaaccaaggttctaagcaagacgttgaagctttgatt
gaatttatctacgacactgaaaagaatggtggtttaggttgggatctagatgctattattccattcgcggccattccagaacaagg
tattgaattagaacatattgattctaagtctgaatttgctcatagaatcatgttgaccaatatcttaagaatgatgggttgtgtcaaga
agcaaaaatctgcaagaggtattgaaacaagaccagctcaagtcattctaccaatgtctccaaaccatggtactttcggtggtga
tggtatgtattcagaatccaagttgtctttggaaactttgttcaacagatggcactctgaatcctgggccaatcaattaaccgtttgc
ggtgctattattggttggactagaggtactggtttaatgagcgctaataacatcattgctgaaggcattgaaaagatgggtgttcgt
actttctctcaaaaggaaatggctttcaacttattgggtctattgactccagaagtcgtagaattgtgccaaaaatcacctgttatgg
ctgacttgaatggtggtttgcaatttgttcctgaattgaaggaattcactgctaaattgcgtaaagagttggttgaaacttctgaagtt
agaaaggcagtttccatcgaaactgctttggagcataaggttgtcaatggcaatagcgctgatgctgcatatgctcaagtcgaa
attcaaccaagagctaacattcaactggacttcccagaattgaaaccatacaaacaggttaaacaaattgctcccgctgagcttg
aaggtttgttggatttggaaagagttattgtagttaccggttttgctgaagtcggcccatgggggttcggccagaacaagatggga
aatggaagcttttggtgaattttcgttggaaggttgcgttgaaatggcctggattatgggcttcatttcataccataacggtaatttg
aagggtcgtccatacactggttgggttgattccaaaacaaaagaaccagttgatgacaaggacgttaaggccaagtatgaaac
atcaatcctagaacacagtggtatcagattgatcgaaccagagttattcaatggttacaacccagaaaagaaggaaatgattca
agaagtcattgtcgaagaagacttggaaccatttgaggcttcgaaggaaactgccgaacaatttaaacaccaacatggtgaca
aagtggatatcttcgaaatcccagaaacaggagagtactctgttaagttactaaaggggtgccactttatacattccaaaggctttg
agatttgaccgtttggttgcaggtcaaattccaactggttggaatgctaagacttatggtatctctgatgatatcatttctcaggttga
cccaatcacattattcgttttggtctctgttgtggaagcattattgcatctggtatcaccgacccatacgaaatgtacaaatacgta
catgtttctgaggttggtaactgttctggttctggtatgggtggtgtttctgccttacgtggtatgttaaggaccgtttcaaggatga
gcctgtccaaaatgatatttacaagaatcatttatcaacaccatgtccgcttgggttaatatgttgttgatttcctcatctggtccaat
caagacacctgttggtgcctgtgccacatccgtggaatctgttgacattggtgtagaaaccatcttgtctggtaaggctagaatct
gtattgtcggtggttacgatgatttccaagaagaaggctcctttgagttcggtaacatgaaggccacttccaacactttggaagaa
tttgaacatggtcgtaccccagcggaaatgtccagacctgccaccactacccgtaacggttttatggaagctcaaggtgctggt
attcaaatcatcatgcaagctgatttagctttgaagatgggtgtgccaatttacggtattgttgccatggctgctaccgccaccgat
aagattggtagatctgtgccagctccaggtaagggtatttaaccactgctcgtgaacaccactccagtgttaagtatgcttcacc
aaacttgaacatgaagtacagaaagcgccaattggttactcgtgaagctcagattaaagattgggtagaaaacgaattggaag
ctttgaagttggaggccgaagaaattccaagcgaagaccaaaacgagttcttacttgaacgtaccagagaaatccacaacgaa
gctgaaagtcaattgagagctgcacaacaacaatggggtaacgacttctacaagagggacccacgtattgctccattgagagg
agcactggctacttacggtttaactattgatgacttgggtgtcgcttcattccacggtacatccacaaaggctaatgacaagaacg
aatctgccacaattaatgaaatgatgaagcatttgggtagatctgaaggtaatcccgtcattggtgttttccaaaagttcttgactg gtcatccaaagggtgctgctggtgcatggatgatgaatggtgctttgcaaattctaaacagtggtattattccaggtaaccgtaac
gctgataacgtggataagatcttggagcaatttgaatacgtcttgtacccatccaagactttaaagaccgacggtgtcagagccg
tgtccatcacttctttcggttttggtcaaaagggtggtcaagctattgtggttcatccagactacttatacggtgctatcactgaaga
cagatacaacgagtatgtcgccaaggttagtgccagagagaaaagtgcctacaaattcttccataatggtatgatctacaacaa
gttgttcgtaagtaaagagcatgctccatacactgatgaattggaagaggatgtttacttggacccattagcccgtgtatctaagg
ataagaaatcaggctccttgactttcaactctaaaaacatccaaagcaaggacagttacatcaatgctaacaccattgaaactgc
caagatgattgaaaacatgaccaaggagaaagtctctaacggtggcgtcggtgtagatgttgaattaatcactagcatcaacgtt
gaaaatgatactttatcgagcgcaatttcaccccgcaagaaatagagtactgcagcgcgcagcctagtgtgcaaagctcttc
gctgggacatggtccgccaaagaggctgttttcaagtccttaggcgtcaagtccttaggcggtggtgctgcattgaaagacatc
gaaatcgtacgcgttaacaaaaacgctccagccgttgaactgcacggtaacgccaaaaaggctgccgaagaagctggtgtta
ccgatgtgaaggtatctatttctcacgatgacctccaagctgtcgcggtcgccgtttctactaagaaatag

SEQ ID NO. 5:
>RtFAS_ACPII2TE
atggtcgcggcgcaggacttgccgctcgcgctgagcatcagcttcgcgccccgagtcgtcgaccatctcgatgacgctgttcaa
ccagcccgaggcgtcgaaacccgccctccccctcgagctcaagtacaagtacgaccccctcgacgccgtacgccccgatcca
cgagatcaccgaggaccgtaatcagaggatcaagcagcactactgggacctctggggcctcggcaacaaggcagaccagg
gcatctcgcagctcaagatcaccgacgagttccagggcgacctcgtcaccatctcggccgacgagatcgaggcgttctgccg
tgttgtcggcatcgagggcgaggcgtacaagcgcaaccacaaggccggcatgcaggtcccgctcgacttcgccatcaagct
cggctggaaggccatcatgaagccgatcttccctcgacgattgacggcgacctgctcaagctcgtccactctcgaacggct
tccgcgtcctccccgacacgcccacactccaggttggcgacgtcgtgacgaccacgtcgcgcatcgaatcaatcacgaactc
ggacacgggcaaaaccgtctcggttcgcggcgtcatctcgctcgtctcgtccgccgactcgaagggcaaggacgcctcgac
cgaggaccgcatcccgctcatcgaggtcacctcgtccttcttctaccgcggcaagttcagcgactacgcccagacattctccc
gcgtcgcccacccgaccactctgtcccgatcaccacgcccgaggccgtcgccgtcctccagtccaaggagtggttccagtg
ggacgacgactcgaagcccctcgaggtcggcaccaagctccagttcaaggtcgagtcgaactatgtctacgccgacaagtc
gtcctacgcgatggctaccgtcaccggcggcgcgtacgtcatcaccccgagctcaagctcgctgtcaaggttgccacggtc
gactacacgtccgagggcgagggcgtcatccagggcgacccggtcatcgagtacctcaagcgccacggctcggccctcga
ccagcccatcatgctcgagaacggcggctattcgctcaccaaggccggccagtgcaccttcacgacgcccgcgtccaacct
cgactactcgctcacctcgggcgacacgaacccgattcacacgaacccgtactttgcctcgctcgcctacctccccggcacca
tcacgcacggcatgcactcgtcggcccgcacgcgcaagtttgtcgagcaggtcgccgcagacaacgtcggcgcgcgtc
cgcaagtacgaggtcggcttcacggccatgtgcctcccctcgcgcaagatggaggtccgccttaagcacgtcggcatgacc
gcggacggaaaccgcctcatcaaggtcgagaccgtcgacgtcgagggcggcaacgtcgttctcagcggaaccgccgaggt
cgcccaggctccaccgcgtacgtcttcaccggtcaaggttcgcaagagcccggcatgggcatggagctctacgccaactc
gcccgtcgcccgcgccgtctgggacgaggctgaccgccacctcggcgaggtctacggcttctccatcctcgagattgtccgt
acgaaccccaaggaaaagactgtgcacttcggcggggttgaaaggccaagcaacccgtcagaagtacatggacatgtcgtac
acaacgactgaccatgagggcaacgttaagactctcccgctcttcggcgacatcgacctccgtacctcacgctacacgttctcg
tcgccgaccggtctcctctacgccacccagttcgcccagatcgccctcgtcgtaacggagaaggccgccttcgaggacatgc
gcgccaagggtctcgttcagaaggactgcgtctttgccggtcactcgctcggagagtactcggctctcgcctcgatcgccgac
atcctccccatctcggccctcgtcgacgtcgtcttctaccgcggtatcaccatgcagcgcgccgtcaacgcgaccacctcaa
ccgctcgtcgtacggaatggtcgccgtcaacccgagccgcatcggcaagagctttggcgacgccgccctccgcgaggtcgt
cgacaccatcgcccgccgcgggaaacatcctcatcgaggtcgtcaactacaacgtcgagggacagcaatacgtcgtcgccgg
tcacctcgtcgcccctccaatccctcacaaacgtcctcaacttcctcaagatccagaagatcgacctcgccaagctcaccgagac
gatgtcgatcgagcaggtcaaggagcacctgtgcgagatcgtcgacgagtgcgtccagaaggcgcgcgacctccaggcca
agacgggcttcatcacccctcgagcgcggctttgcgacgatcccgctccccggtatcgacgtgccgttccactcgcgctacctc
tgggcgggagtcatgccgttccgcacttacctctcgaagaaggtcaacccggcgcacttcaacgccgacctcctcgtcggcc
gctacatccccaacttgaccgccgtccactacgaggtctcgaaggagtacgccgaacgcatccacacccagacgtcgtcgcc gcgcctcaacaagattctcaaggcctgggacgaggagcgctggggcgcacccgagaaccgcaacaagctcggctacgcc
atcctcatcgagctcctcgcgtaccagttcgcctcgcccgtccgctggatcgagacgcaggacatcctcttccgcgacttcaag
tttgagcgcctcgtcgagcttggcccgtcgcccactctcaccggcatggctacgcgcacgcagaagctcaagtacgacgcgc
acgactcgtcggtcggcatcaagcgctcgatctactgcatcgccaagcaccagaaggagatctactaccagttcgatgacgtt
gccggcgaagaggcgcccgctcctgccgcagttgcgccttccgctcccgctcccaaggccgccccagtcgccgccgcccc
tccccctcccgctcctgtcgctgccgcgcctgccgccgccgtcgccgacgagccgctcaaggctgtcgacacgctccgcatc
atcatcgcgcagaagctcaagaagcccgttggcgaagtcccctcaccaagtcgatcaaggagctcgtcggcggcaagtcg
accctccagaacgagattctcggcgaccttcaaggcgagttcagcagcgcgcctgaaaagggcgaggagatgcctctccag
gagctcggcgcggccctccagcagggctactctggcaagctcggcaagtacaccaccggcgtcatctcgcgcatgattggc
gccaagatgcccggcggttttggtctctccgccgtccagggtcacctcggcaagacctacggcctcggcgccggtcgcatcg
atggcgtcctcctcttcgccgtcacgcaggagccggctaagcgtctcgccaacgagggtgaggcgaaggcttgggtcgact
cggtcgcgcaaggctacgcctcgatggctggcatctcgctcgccgccggcggtggagctgctgctgctgcccccgcgatgg
cgttcgccgctccggccgcagctggcggtggagcgcccgctaagactatattgatattgggtgactcattgtccgctggttatg
gtattaatcctgaacaaggttgggtcgccttattgcaaaagagattggatcaacaattcccaaagcaacataaagtaatcaatgc
atctgtttcaggtgaaactacatctggtgctttggcaagattaccaaagttgttaaccacttacagacctaacgttgtcgtaattgaa
ttgggtggtaacgacgccttaagaggtcaaccacctcaaatgatccaatcaaatttggaaaagttaatacaacactcccaaaaa
gctaagagtaaggttgtcgtattcggtatgaagatcccacctaactatggtacagcatactctcaagccttcgaaaataactataa
ggttgtctcacaaacctaccaagtcaaattgttaccatttttcttggatggtgttgctggtcataagtccttaatgcaaaatgaccaa
atccacccaaacgccaaagctcaaagtatattgttgaacaacgcttacccttacatcaagggtgcattagctggtggaggcgga
ggcggcgcggctgtcggcggcgccggctttatgatcaacaccgagcagctcgacaagatgcaggagaagcaggacaactt
cgtctcgcagcaggtcgagctcttcctccgctacctcggcaaggactcgcgcgagggccaccgcctcgccgacatgcagaa
ggcagaggtcgccaacctccaggagaagctcgactcgatcgctcgcgagcacggcgacgcctatgtccagggcatccagc
ccgtcttcgacccgctcaaggcccgccacttcaactcgtcgtggaactgggtccgtcaggacgcgctcatgatgtggatggac
atcctcttcggccgcctcaccaccgtcgaccgcgacatcaccgctcgctgccttgtcatcatgaaccgcgccgacccttctctc
atcgactacatgcagtacaccatcgacaacaccccccgtcgagcgcggcgagcattacgtcctcgccaagcaattcggccagc
agctcctcgacaactgccgcgagatgatcggccaggctccgctctacaaggacgtcaccttcccgaccgcgcccaagacga
ccgtcaacgccaagggcgacatcatcaccgaggaggtcaaccgccccggcgtctctcgcctcgagaagtatgtcgccgaga
tggctgccggctcaaaggtcaccgtcgccagcgtcaacctcgacaaggtccaggagcaggtcgagaagctgtacaagctcg
tcaagtcgcagccgcagatttcgaagcagcacatgacgtcgatcaagtcgctgtacgctgaggtcgttcgcggtctcggcaag
gacgccggccctcctccggtccacaaggccggcactcgcgcccgccgcccctcgagccagttcctccgtcccgcagccgt
ctccgaggcgactttcctccccgaggacaaggtgcctctcctgcacctcaagcgcaagatcggcaacgactggcaatactcg
agcaagctcacgtcgctctacctcgacatcctcaaggagattgccacgtcgggtgtcaccttcgagcacaagaacgcgctcat
gaccggtgtcggcaagggctccatcggtatcgagatcgtcaaggggtctcctcgctggtggcgctcgcgtcgtcatcacgacct
cgcgctactcgcgctcgactgtcgagtactaccaggcgatctaccaggaggtcggctcgaagggctcgtcgctcaccgtcgt
ccccttcaaccagggctcgaagcaggatgtcgaggcgctcgtcgacttcatttattcgaaggataagggtctcggcatggacc
tcgactacatcctcccccttcgccgcccttcccgagaacggccgcgagatcgacggcatcgacgaccgctccgagctcgccc
accgcatcatgctcaccaacctcctccgcctcctcggtgccgtcaagtcgaagaaggccgccctcaagctcacgacccgccc
aaccgaggtcgtcctcccgctttcgccgaaccacggcctcttcggcaacgacggtctctactcggagtcgaagatctcgctcg
agacgctcttcaaccgctggagctcggagagctggggcgagtacctctgcctcgctggcgctgtcatcggatggacgcgcg
gtaccggtctcatgtcggcgacgaactcggtcgccgaaggtatcgaggcgcaggggttgcaggacgttctccgccaaggaga
tggccttcaacattctcggcctcatgcacccgctcgtcttcgacgtcgcgcagatcgagcctgtctgggccgacctcaacggtg
gcatggacaagctccccgaccttgccaacctcacgaccgagatccgcaagaagctcaacctcaccgcgtcgacccgccgc
gccatcgccaaggacaactcgttcgactacaaggtcgcgcacggcccggcgatggagcagatacaccagcggatcaacgt
cgccccgcgcgccaacttctccccttcccttccccgagctcaagccgatcgatgccaagtcggagctcgcgaagctccgtggc
ctcatcgacctcgagaaggtcgtagtcatgaccggttacgccgaggtcggaccgttcggctcgtcgcgcacgcgctgggag
atggaggcgaacggcaccttctccatccagggcacactcgagcttgcgtacgtcatgggcctcatcaagcactttgagggtcg FIG. 10 (Continued)

cctcaaggacggcacgctctacgtcggatgggtcgacgccaagacgaacgaaccgctggacgacaaggacgtcaaggct
gcgtacgagaagcacattctcgcgcacaccggcatccgcctcatcgagccggagatcttcaacggctacgacccgaagcgc
aagggcttcacgcaggagatcgagatccagcacgacctcgagcccatcgaggcgtccgaggaggacgcggctcgcttcaa
gcgcgagcacggcgcgctcgtcgacgtctacaccgaggacggcagcaagttcttcgtcaagttcaagaagggcgccaagct
gcacattcccaaggctgttgccttcgaccgccttgtcgccggacagatcccgactggctggtcgcacaaggccttcggtatcc
ccgacgacattgcctcgcaggttgaccgcacctcgctgtgggcgctcgtctcggtcgccgaggcgctcatgatggccggcat
caccgacccgtatgagctctacaagtggattcacccgagcgaggtcggttcgtcgctcggatccggcatgggaggcatcacg
agtatctcgaagatgttccgcgaccgccgcgaggagaaggacgtccagaaggacatcctccaggagaccttcatcaatacg
gtcgccggatgggtcaacctcctccttctctcgtcatccggaccgatcaagatccccgtcggcgcctgcgcgactgccctcca
gtcggtcgagatcgcctgcgacaccatcctcagcggcaaggccaagatcatggtctcgggaggctacgacgacttctccga
ggagggctcgtacgagttcgcaaacatgaaggcgacctcgaacagcgagaccgagttcgctgccggccgcgagccgaac
gagatgtcgcgtccgacgaccagcacccgtgccggcttcatggagtcgatgggttgcggtgctcaggtcctgatgtcggcga
agacggccatcgagatgggcgccaccatctacggcatcgtcgcctacaccgcgaccgccaccgacaaggctggtcgctcg
attcccgccccggacgcggtgtcatgggtaccgcgcgcgagatcacctccaagtaccctcgcccatcctcgatgtcaccta
ccgccgccgccagctcgagttccgtcgcaagcagatctcgcagtggctcgagaacgagaccgagctcctcaagttcgaggt
ctcctcgcacggacaggccacaaagctccccgacgactacgtctccgagcgcctcgcatccatcgaacgcgaagccaagc
gccaggaggccgaggctctcgcgacgtacggcatgctcgccggccaggacccgaccatcgccccgctccgtcgcgctctc
gccgtttggggtctcaccatcgacgacgttggagtcgcctcgttccacggcacctcgaccgttgccaacgacaagaacgagt
cgaacgcgtacaacgagcagttccgtcaccttggccgcgccaagggtaacgcctgccccgtcatcgctcagaagtggctca
ccggacacccgaagggaggtgccgccgcctggatgctcaacggcttggcccaggtcattcagagcggtctcgttcccggca
accgcaacgccgacaacatcggcgaagagcttcgcgcgttcgagtacctgctctacccgtccaagtcgatccagaccgacg
gcatcaaggctggtctcctcacctcgttcggcttcggtcaagtcggtggccaggctctcatcgttcacccgagtctgctcatcgg
cgcgctcgagcccgcccagttcgaggcgtacaagaagctcaacgaccagcgcaagaagtggtcataccgtcgcttcaacga
tttcttcacgaacggcaagctcgtcattatcaaggacggcacgcccttcacgcccgagcaggagaacacgaccctcctcaac
ccgctcgtccgcgccgtgcccgacaagactggctcgtactcgatgccgaaggagttccctgccaccgtccctcgcagcaaca
acgccgaagtcgccaacaagctcgtcagcgcggctgtcggcggtgctttcggcgtcggcacggacgtcgagctgatcagcg
ccgtcccgacctcggagtcgttcctcgagaggaacttcacccaggacgagatcgcctactgcaaggccgcacccgacttccg
cgctagcctcgccgcgcgctggtccgccaaggaggccactttcaaggctctcaagaccgagtcgaagggcgccgccgcca
gcatgcaggacatcgaggtcgtctccacgtcgcagggcccgactatcaagctccacggcgaggtcgagaagatcgcccag
gccgccggcatcacggccttcgaggtctcgctctcgcactcggaggacgtcgcttgcgccgtcgtcatcgcccagaagtag

SEQ ID NO.6:
>AkFAS-ACPII2TE
Atggaacaacataaaactgagaaactttcagcagccgatgaaaagttgagtgagagtacaattcattggcttgctgcaacaga
tgtcccttcaaactttgtactcttttccggacaagggtatcaatactttgatgagctccgggaactgtatgaaactggcacagatga
ggttaaaggcttcctttacttgcttcgaaaacactgcaggaagagatctgtagtgaaaaagcgaaaactgtcgctttcaaatttgt
caatgagcttgactttacgaaatggatagaagaggatatcgatgtggatcaaacctacatcttttctgctccagtttcttttcccctta
atatttgtcgctcaagttgcaaggtacttgcaaactttaaacttgctaagaacagaccacaaacaatttatccagacaattaaagg
gtctagtggtcatagtcaagggattgttgctgctgtattgatatctacatcgcctgacaacgacagaattgttgagaatgcagtca
aactttgcagatatatgttatggcaaggggctgagatgccatgaaagcagtgtaaacagattcagtggcaaaaaccacaaatcga
aaaagtctaaagtttattcctttgatgaatcgacccgcatggtaaagtattctcccatgcttgctgtcaatggtctcacggaatccct
cctcaacgattttatgaagaaaactgaatccattattgaagcaagaagaacgatacaacaaagtataaccgaagagaatcattt
tttgaaacaccaacagaaaaggatgagaaaagtaaaagacttaatatgtttcaaattgcacttgcaatggccccaagtcatttgt
tgtctctggagcgccaaaaacacttattgagctagaacaaagaataaaggagtcaactacatcgtctccaaactctcaaacacg
tataccatttagcaagcgcaagccagttgttaaaatgtatttcctcaaggttggggctgcttttcatactgaaatttgtaatgacgcc
tctagtaaactaaaagccgatgtggtccaaatgaaattgagtatctcgccaaaggaaatattaattcctgtctaccatacaaaaga

FIG. 10 (Continued)

tggttcgaatttatcggagatctcagcagatgtgaatgttgtcgatttgctaattgatatgcaaactagtcaagtcaatgatttcaga
aaaaccttgaagagtatttcaagtcagaatgggtgtcaaacgttattgattttggtccaggtgacggaactgctaaattgtgcct
gaaacgaaagtctggaactggtatactagttgtcgcggctactggaccactacgaaacagaagatgtgcatatggtagaaatct
tgtcggtctaaactctgttttgctggaaaaaaatcctatactagggatgaattgggggaagaatttaagcccagactgtcgagt
cgcaagaatgacaaccaaatcattgtcggaactagatttagtgacttgactggaaagccgcctgtaattctacctggaatgacg
cctactacatccttcacggcatcgatttggttgccgcctgtagtaatggtgggtatcatggcgaacttgctggtggtggattgcc
actgccagaatacttcaaagcgaaaattgatgagctagtgagcaagcaaaactctggagtaggcataaacataaacatgcttta
cctaaactcctacttatggggttttcaattttccactgccattcagatggcgaaagatggatatcccatagaatctatcacttgcgcc
gccggagttccaactactgaaaaagcgaaagaaataatgcatcagttgaaagaagctggaattaaatacattgccttcaaacct
ggatcaagagccgcaattatggatgtattatctattgctagagaaaaccccaatagttcaatcgtactgcaatggacaggagga
cgtggaggtggacatcactccttcgaagactttcatgctcctttgctcgacacttatcaagaaattagagaacacccaaacgttgt
tctcgtcgtaggctccggatttggagatgcagagaagtcatacccatatttagatggttcgtggtctacattgcctccacataact
gtgaatcgagaatgccatgtgatgcagttttatttggatctaggtgcatggttgcaaaagaagctgctacctctccagaagttaag
caattgattgttaacgctaagggcgtccgagaaaacgaatcttgggaaatgtcttacgaaaacgatgctggtggaattctcactg
taacttccgaactcggcgagcctatccataagataaacaaccgcgggatgaagctatggagagagtttgacagaaagtacttct
cattaccttcgggccaagaaagggaaaaggctatagtgaaagataaaaaggagataattagaaggattaatgcagattttcaaa
aagtttactttggaaggaaggccgatggaactgttgtggacattgcatatatgacatatggtgaaattttacggagaatggtgga
cctaatgtacgtaaccggaggaggagatggaaaacaacatagatttgcgccaaacagatggatagacgttacgtaccaaact
agaacgttcaagttttagttcgcacagaaagacggttttgagagacaaaaaaatggcctttgcaactgatatgagaaaactcg
aatcttttccgataaagtgcattgatgagttcgtcaagtgctaccctcaagtagataaagtgctggtatcggacgaagatgctgga
tattttatcgaactttgtcgaaaccttagaaacggaaaaccggtaaattttattcctcaaattgatggctctttagcttactggttcaaa
aaagactctctctggtgttctgaacagattgacgcggttcccgacaatgaccctggcagagtttgcatactacatggcccagtag
cagcgcaatattcagtagtgtcagatgagcccatgcgaaatcctcggtaacattcacaagggatacgtggacaagttgaaa
gaggagaagtatgaggtggccaaagttgaaacaatcggaaagctacctgaatacaaaggttccaacaagtctttccgcaaattt
cttcgttatggttggttcaatgccctgtttcaaagtaccgtaatggtcaaggagaaaaagtgggtcagaaacattattccaggaat
catacaaacggaaaacgaaaacattgtattctcagagcgaacagcaatgaatgatatgtgtctcatcgaagttcttttaaatgatt
cacagagaactctagctttcatagagtttgaaggaaagcacatttctgtgtctttgcaggattctgaacctgtaaacagcacactg
accctgtattttgagtaccatcctgaaactcctcactctccgttatttcaagtcacaaatggaagcaaaagtattgctagatcaatca
aacagtattacaggaatatatgggattgtcaggatgttgtttctatccatgatacattttccgaaagcttcaccgtcacgagagaag
acatcgaaaggttcaatggcgcaattcaatatgcggtaaatacttcggagggaactttagactttgcaattgttgcaggatggaa
atcactgataaaagctctgttttcaaaagagatagacggcagtctgttagatcttgttcacatctcccactcatacaaactacttgta
gaggagaaggagagaacgcttgttcaagctggagagaaaatttgttcggaatctcgcgttatttcagtacagatattaccaggt
gttggaaaaagtataacagttaaaggggtactctctagaaacacagtcaaatgggttgaagtccaatccgagttttaatccgag
gcaatttcttcgattttcaaaagactttcaaggaatatagctacaaagctgaggttttatgtaaagacgatacagttccgcaaatcct
aaactcacaggaatggcttttttctggactctggagtcagacctctatctaaacacgataaagttgtatttcaaatcgatcgcgttgt
ggaaaagagaaagtctgtgacaaatatttctgatattttagttgctggtaatgttgttcgaatcaatacacctgaagagatcgatgg
ttttattgaattgaaagaccaaggaagcccaaagggaatcatcattgggaaagttgatttaagccttgaaaatgccaatctgagt
gaaaatccaattattacatatttggattccattaaagaatcaaaattgcacggtagtgtttttgaatcgggaggatatactgtgatgc
cgaggccccgaactagtaacagcgccaagtattgtcgaaagcattgtgatgcatctgcttctagagatatgaatccaattcatcg
gaatcgcacattcgctaagttagctggactccccggtggtagtaccattgtgcacggaatgtggacagctgcaatgagcagaa
gaattctagaattacatacagttctcggagaccatcgccgtatttccacatactcggttaaatttaccggcatggtgttcccagaag
acaaactagccgttatggtcaaacacgttggtgttacggaaggtagacttattcttgatgtagatgttagcaaagtagaaacgca
agagcgggttctccacggacgagctgaagtagaagggccgtcgacatcattcctattcactggtcaaggatccgcaaaagttg
ggatgggaatggacagctacgaagaaaagcagtcggcacgggcagtttggcaaactgcagataaattttgaggaaaaattt
ggatttcaattgttgatattgtcaaaaataatccaaaagagttgactgttcgttcggtggatcacaagggaaagtgattcgagaa
aactacagagccattaaaagggaagatggatctcaattgatccgagaaatccatagtaataccacgtcatttacatttcgttcacc FIG. 10 (Continued)

aaatgggcttttatttgccacgcaattttctcagccggcgctggtactagtgcaaaaagcagcgtttgaagaaatgcttcaagga
gggtttgttccgtcaaacagtatgtttgctggtcattctcttggtgaatacgcagctcttgcctcgtatgcaaacgttctgagtatcg
aagacttagttgaaactgtattttaagaggaatggtaatgcaaaatgcagttgcaagggacgacgaaggaacatctgattacg
gtatggtggctgccaatccttcaagagtcagtaaaacgttctcggcacaattgttgatggaaatcgtccagaaaattgacgacga
atcagatgacagtcatcttctccaagtagtaaatttcaatattagagatgctcagtacgtaatagctggaaatctggaattgttagat
agtctatcgaatgttctcaatgtaatttcaaacagccacgacaaaacctttgacagaagcattatccaagctgcaatgataaagg
ctgaaaataggagaagaagctgcaaggaaaacaatcaaccttttccgtcttaagcgtggaatcgcaaccattcctcttcacggca
ttgatgtaccttttcattctcgacagcttttgaatgggtacctgcttttcggtctctactagaaccaagatttacggaagaaatgatt
caaaagtacttgcctaggttgatcggaaagtacattcctaatgtgcacgcagaaccgttttccattagcaaagagtacattgaaa
aggttgcaagtgtaacaaaatcgccagcgttgtacaagcttctatctacatactcaacaatgtgtgactcatcaaaagcaagaat
cttgctcatagagcttttagctcatcaatttgcaatgccagttcaatggatagatacccaggactatatactctccaggcacacaca
gcgaataattgagatgggcccagccccaactcttgttggtatggcgaaaaagacattgcaatctagaatatatggtgacgaaga
agactacaaacctagtattctgtggtggaatcaaaaccaggaggaaatcttctataacttggacaatcaaggaatatctattcaac
agttttttgcaagaattaaaaggaactgaagatgacgagtcacagtctgatgatatgtcatcatatacccagtcagacgagactat
acaaagaactgcaaagaacagggttatgccagaagcaaatgcaaacgacaaggagaaagtggggaatgaacttcaaaaga
aggaagttacaaacaggcctcttcatgtcctaagagtcctcatctcaaccaaacttaagaagaaaatgttggaggtaaaggcaa
cagacaccatcaagggtgtttctggtggaaaaagtgcgattcaaaatgagctaattggagaaataaacgctgaatacagcagtt
ttagagatattgaagatatttcggaagtttctttagctgagctagctagaagggcccccatcccggcaggaaacagttcttggtaaa
gttacaacgaaaatggtgaacaaaatgttttctagcaaactgcccggaaaatttggtcctaatgatactaaggagtacttacaaa
gcaaactctcggatgcgtccacagtcgattcagtgtctcttcatgccctgactctgcagccggtttctagactagctaccctgga
gaggcacaggcatggcttgattctgtttgtagagactttgaaaacgatcagagaatcagtattctaaagaacaaaagtccaaatt
cgaacgaaagtgtgatgatttctgaacaaaggactgttcaaaacaactttgtacaaattaagactatattgatattgggtgactcat
tgtccgctggttatggtattaatcctgaacaaggttgggtcgccttattgcaaaagagattggatcaacaattcccaaagcaacat
aaagtaatcaatgcatctgtttcaggtgaaactacatctggtgctttggcaagattaccaaagttgttaaccacttacagacctaac
gttgtcgtaattgaattgggtggtaacgacgccttaagaggtcaaccacctcaaatgatccaatcaaatttggaaaagttaataca
acactcccaaaaagctaagagtaaggttgtcgtattcggtatgaagatcccacctaactatggtacagcatactctcaagccttc
gaaaataactataaggttgtctcacaaacctaccaagtcaaattgttaccattttcttggatggtgttgctggtcataagtccttaat
gcaaaatgaccaaatccacccaaacgccaaagctcaaagtatattgttgaacaacgcttacccttacatcaagggtgcattacg
tactctctcttcaggtgatagtagtcctgctcattcgacaaaagatatcctttcgtccactgcaatgaagaaattgaaaaaattgtac
ttggaccaggtggatgtcttcaacacttttttgggagaggatcgacgggccaaacttcaaaaggttctaacagaggaaaccagt
gcaaaagatagaatagaggctcagctccttgaattaaaggaagaacttggagacccttttgtgacgggatacaaccccagttt
aatgaagctcggatacgaatctatgattcatactggaactgggtggtgcaggatgcattagaactccattatcatacattctcttgt
gtgttgaactcaaaaggcaagaacgtaaatattcccaattcatctaacagctattttcgcgcaatgagcgactggataacttcttc
aaacgaaaagttggaagaaaataaacctccgcaggcttggtttcgcaattacctttgtaatcgtgccactccagaacttctaacc
gttgtacaatactttgcagcaagaatgaacgaacaaggacattcagaatatgctcaagcagtatctcttttagcagaacaagtatc
acagtggatatctagaccacctgtacacatagcattgtttgcatctctagaacctagggtgacagttgatagtgctaacaattttgg
attgaaatatgaagaaaaaccaagaaagtttgtggctgtcggtgaaaacaaagctttctcgtgtgataatgcgtccctgtatgtta
aagaaatgagcaagggggctatttatgaccaccgtgtggcttcgaaagttgaacatcccagccaaagtgtataccttctcccga
taattctttctttccaaacgaggaagagagtgaccagatttcaagcggaatgagactaccaaaaacacaaggagaaatccagc
gtgattttcaagactccctgctggtcagaagctagaagtcatgagaaagagtgttaatcggtcgtccgacacagatgaggaaa
ttgccaacatcgttcgacaaaactataacagtatccatgtggcaaaaaacgtacctttggtgcatttgaaatcgccttctaaatttg
acaagacgggtaagagtactcgatgagcctttgacatcaatgtacttgagttgtttgcatgatattgcaacaagtggagttagctttg
caggacaaaacgctttggtgacaggagccggcttttggttcattgggattgaattaatcaaaccgttgcttgagggggggggcaa
cggttttagtaacagttagacttaatcggactgacgagcaaatgcaaattgttaatgaaaggtttcaaagattgtacgaagagttt
gggtccagaggaagcaagctcgttctggttccttgcaattgcgcttcaaatcaagatgtacattccctcattagacacatctatga
gaaattgaaacttgacctagattttatatttccatttgctgctatcggggagcaagggaaagatgtgtctgaaattggctccaaatc FIG. 10 (Continued)

tgaagtcgctcatagactaatgctgactaatactataagattactaggtgcagtgaaaaaggccaaagaggatagatgcattga
aacaaggcctgcactggttctgttgccatgctctccaaaccatggggattttggactagatgggttatatgcagaatcaaagcttg
gattggaatccctagtaaacaagtggaaaagtgaagaatggggaaattacctaagtatttgcgctgcagtcataggttggacaa
ggtccaaactcatgtggcagaacaatgtcgttgccgagggaatagaaaagttgggagtgagaaccttttctactacagagact
gcttttaacctgattggtctactacatcctgatatcgtgtctcatgcagcagaagaacctctatgggcagaccttactggaaactg
gggcgctgctcctgacttgaaggaacattcaaaaaggattcgaacgtcacttctggcacaaagtaaagcagcaaaagccatat
cgctgtcgtcaaaatcgctcgttatagaaccttctgaatccaagacgaaagcgcagacagaaattgttaacacatacctagctg
gtgtgaatgataagttgaggcttccgctagcaaatcccgaaaagttctgcaatccattccctaaaattccatcccaggaacgaat
ggattcattagcataccttaaacactcagtagatctcaaaaagtcgtagtagtagtaggatatggagaaattgggccttgggga
aattcgcgcactagatgggagatggagtcattcggtgaattctcgcttgaaggtgcaatcgaacttgcttggctcgttggcttaat
caaaccagttactggaccgttaaaaaatgatcctagaacgcaatactttggttgggtagatgcagaatcagaagagccagttgc
agatcatgaaataaagactcgatatgagaaagtactgcttcagcactctgggattcgtcttattgaaccggagctctttgaaggat
ataatccaaagaaaaagtcaattctgagacaagtagccatcgctgaagacatgaaaccaatagaagtagcttctttggaagaag
cccagcagtacgtgaatgagttagggaaagagttcatagacgttttaatgaaaacgttgaatctaatgatggacaatggtatatt
cgcctaaaagcaggagcagtggtctccattcctggagcgttaagcttcaacagatttattgctggtcagctacctacaggatgg
gatgcaaaacgactaggaataccagatgatattgccgactctgtagatcctgttacgctatatgctctggtttcaacagttgaagc
cttggtgtgtgctggattgacagatccatatgaactgtatcaatatgtgcatgtaagtcaagttggaaacacgtcaggtggcggc
atgggagggatgcgatcattgaagcgaatgttcctagaaagaaaacttgatgcagaaatcccttctgatactttagcagagtcat
ttattaacacaatgccagcctgggtgaacatgctgcttctgtcaagctcgggaccaataaagactccagtcggtgcttgcgcca
cagcggcagagtcggtagacataggaattgaaaccatcttagcaggaaaagccagagtcgttatagcgggcgggtatgatga
cttttgtgaaacgggaagtaatgagtttgccatgatgggagcaacttccaacagtcaaacagaagctgaaaaaggcagatttcc
acgtgaggcatcaagaccaatgacagatacacgtgccggattcatggaatcacaaggcgctggtatgcaagtgttaatggatg
ctgaattagccattcagatggggcttccagtatatggtattcttgctctgtcaaacactgctaccgatagacaaggaagatccgtg
cccgccccaggtcgtggaatactaaccactgcgagagaagtgcgctcaaaaaactctaaaagtagccacaacggcaaacca
gtagaaaatcctctattgtctgtaaagttccgcaaaaaacatttgagacaagagctcgatgctatagatctgtgggccagccaag
agatatcgaacatgtctgaggaattctcacagaattcaagaaaaatggaaaacaggaaaggttttgtagaaacaatgcgaaaa
aagaagcgttcggcagcttttgaaacctggggacaaggattctataggaatgatgactccatagcccctttacgcggagctttgt
ccgtatggggattaacagttgatgatcttcttgtgggaagttttcacggaactggaaccaatcttaacgatacgaatgagtcctcc
ttagtgaataagcagcttaagcatttggatcgaaaagaaggaaacattctgttagtagtaactcaaaaatatctgactggtcatcc
aaagggtgcagctgctgcctggatgctcaatggattgctgcaatgcatgaattctggaagagtaccgggaaaccgaaacttgg
acaatgtagatggaaagctcagaacgaacggttacttgttctatccaaatcggacaattgaggttccaagagtggaagcagcttt
tcttaaaagctttggatttggtcaagccggagctgaagttgtcattattcatcctgatcgtctcctggctgttttaagtgaagaaaat
ctgaaatcgtatatacttcgaagaaatgaaagagagaaaagagcatatcgatatcatcaaggcgtaatgagtggacatcatact
atggtgcaagtgaaggaatttgctccatatgaagacgatatcctagaagaaatatatttgaatccaagagctagggcttcctttga
ctcatcgaaaagtacttggacgtttcacaaatataggaacgacaaagatactgtagacgataaagatgaaatggagcaagattc
attgaatgaatcagtagatcttccgaaagatattacaaaagttggatcaccctctgaaatacgtattccagtaaaaacaagattgg
aagttactgttcgtgaaggagtcgaaggtttgacgaaaaaggacaagttttcaagtcaaggggttggcgttgatgttgaaccagt
ttcaacttttgcacaacatgaagagaaaacgatctttattcagaacaacttcactgagaatgaacagctgtattgtaatcatgctgc
aagtccagcagcaagctatgcgggtagatgggcagcgaaggaagcagtgattaaagccatcagcaattcttcacttgaaaca
agatcactttggcaaggagctgagggtaaactgatcgacattgaaatcattcaaagtaattctggtgctcctgaggtagtcttgca
tggtcatgcaaaagaagtattccaaactttaggtcttacaaatgttaaggtttctatcagtcatactccagaagttgcagtagccca
agcaataacaaattaa

SEQ ID NO. 7:
>AcTesA
aagactatattgatattgggtgactcattgtccgctggttatggtattaatcctgaacaaggttgggtcgccttattgcaaaagaga
ttggatcaacaattcccaaagcaacataaagtaatcaatgcatctgtttcaggtgaaactacatctggtgctttggcaagattacc
aaagttgttaaccacttacagacctaacgttgtcgtaattgaattgggtggtaacgacgccttaagaggtcaaccacctcaaatg
atccaatcaaatttggaaaagttaatacaacactcccaaaaagctaagagtaaggttgtcgtattcggtatgaagatcccaccta
actatggtacagcatactctcaagccttcgaaaataactataaggttgtctcacaaacctaccaagtcaaattgttaccattttctt
ggatggtgttgctggtcataagtccttaatgcaaaatgaccaaatccacccaaacgccaaagctcaaagtatattgttgaacaac
gcttacccttacatcaagggtgcatta

SEQ ID NO. 8:
>RtFAS1_AA
mngratrsvtgtstpvhtattrplvllhpstqtrislhvpstsqewiaaevardtfqdwlhaaeksgnlvgfeaaelddeqage
gddekelvltayflkhvagllpfpstatspataavllaafnhfasvylsgtdvhtltaslaapvralvissfflaktklevegIgkv
lpkqsesallqkaatgqaevfalfggqgmnevyfdelqtlhdlytplltpflarasehlvslaaaeqhtllydhsldalawlqd
pstrpevpylatcavslpligltqlcqyvvygkgsslgpaelgakfkgatghsqgvvsalviaheyppaskdgsdawepfy
eqalrgltvlfqiglqgtlafpsiaispalesssvengegvptamlavtgldlkslekkiaevnghvksegrdetvsislyngar
afvvtgapkdlvgladglrknrapagkdqskiphskrlpvfsmrflpinvpyhshllqgatekalatfsaeeaahwapssft
cavyntedgsdmrqlsassvlesvfqqiftspihwvshatnfpssathaidfgtggasgigslcarnwegrgirtimlgnrg
egvgagkeawgkkvpteekwnerfhprlvrtsdgkihldtpfsrllskpplmvggmtpttvkagfvsavlragyhielag
gghynekavrakvaeiqklvnkpgmgitlnslyinqrqwtfqfplwakmkqegepveglcvaagipstekakeiidtlr
eagikhvsfkpgsvdgirqvvniasanpdfpiilqwtggragghhscedfhapilatyasirqhpniklvagsgfgsaegc
ypylsgewsekqygvarmpfdgfmfaswvmvakeahtsesvkqlivdapgvedgqweqtydkptggiltvnselge
pihkvatrgvklwaefdkkvfslskekqlawladnkkyvidrlnadfqkpwfpakadgspcdladmtyaevnarlvrl
myvahekrwidpslrnlvgdwirrveerlsnvndsgikisalqsyselnepeaflkqflaqypqaedqilasadvsyflais
qrpgqkpvpfipvldanfsiwfkkdslwqaediedeavfdqdpqrvcilqgpvaakhctstqtpiaemlgniehqlvknvld
dyyggdesqiptidylapppkpvdagailaenniahsveeladggkkhvysingvlpptgdwhaalagpkldwlqafls
nvsiqageqsipnpvkkvlaprhgqrveltlnkdgqplkldvfggl

SEQ ID NO. 9:
>RtFAS2_AA
Mvaaqdlplalsisfapesstismtlfnqpeaskpalplelkykydpstpyapiheitedrnqrikqhywdlwglgnkad
qgisqlkitdefqgdlvtisadeieafcrvvgiegeaykrnhkagmqvpldfaiklgwkaimkpifpstidgdllklvhlsn
gfrvlpdtptlqvgdvvtttsriesitnsdtgktvsvrgvislvssadskgkdastedriplievtssffyrgkfsdyaqtfsrvah
ptysvpittpeavavlqskewfqwdddskplevgtklqfkvesnyvyadkssyamatvtggayvitpelklavkvatvd
ytsegegviqgdpvieylkrhgsaldqpimlenggysltkagqctfttpasnldysltsgdtnpihtnpyfaslaylpgtithg
mhssartrkfveqvaadnvgarvrkyevgftamclpsrkmevrlkhvgmtadgnrlikvetvdveggnvvlsgtaeva
qaptayvftgqgsqepgmgmelyanspvaravwdeadrhlgevygfsileivrtnpkektvhfgglkgqatrqkymd
msytttdhegnvktlplfgdidlrtsrytfssptgllyatqfaqialvvtekaafedmrakglvqkdcvfaghslgeysalasia
dilpisalvdvvfyrgitmqraverdhlnrssygmvavnpsrigksfgdaalrevvdtiarrgnilievvnynvegqqyvv
aghlvalqsltnvlnflkiqkidlakltetmsieqvkehlceivdecvqkardlqaktgfitlergfatiplpgidvpfhsrylw
agvmpfrtylskkvnpahfnadllvgryipnltavhyevskeyaerihtqtssprlnkilkawdeerwgapenrnklgyai
liellayqfaspvrwietqdilfrdfkferlvelgpsptltgmatrtqklkydahdssvgikrsiyciakhqkeiyyqfddvag eeapapaavapsapapkaapvaaappppapvaaapaaavadeplkavdtlriiiaqklkkpvgevpltksikelvggkst
lqneilgdlqgefssapekgeemplqelgaalqqgysgklgkyttgvisrmigakmpggfglsavqghlgktyglgagri
dgvllfavtqepakrlanegeakawvdsvaqgyasmagislaagggaaaaapamafaapaaagggapaavpdeplka
tdtlraiiaqklkkqipdvpltksikdlvggkstlqneilgdlqgefssapekgeemplqelgaalnqgysgtlgkhtsglvar
mmgakmpggfglsaakahlskahglgpgrtdgallvaltkepekrlgseadakawldgvaqayasqagitlgagggggg
gaavggagfminteqldkmqekqdnfvsqqvelflrylgkdsreghrladmqkaevanlqekldsiarehgdayvqgi
qpvfdplkarhfnsswnwvrqdalmmwmdilfgrlttvdrditarclvimnradpslidymqytidntpvergehyvla
kqfgqqlldncremigqaplykdvtfptapkttvnakgdiiteevnrpgvsrlekyvaemaagskvtvasvnldkvqeq
veklyklvksqpqiskqhmtsiksslyaevvrglgkdagpppvhkagtrarrpssqflrpaavseatflpedkvpllhlkrki
gndwqysskltslyldilkeiatsgvtfehknalmtgvgkgsigieivkgllaggarvvittsrysrstveyyqaiyqevgsk
gssltvvpfnqgskqdvealvdfiyskdkglgmdldyilpfaalpengreidgiddrselahrimltnllrllgavkskkaal
klttrptevvlplspnhglfgndglyseskisletlfnrwsseswgeylclagavigwtrgtglmsatnsvaegieaqgcrtfs
akemafnilglmhplvfdvaqiepvwadlnggmdklpdlanltteirkklnltastrraiakdnsfdykvahgpameqih
qrinvapranfslpfpelkpidakselaklrglidlekvvvmtgyaevgpfgssrtrwemeangtfsiqgtlelayvmglik
hfegrlkdgtlyvgwvdaktnepldkdvkaayekhilahtgirliepeifngydpkrkgftqeieiqhdlepieaseedaa
rfkrehgalvdvytedgskffvkfkkgaklhipkavafdrlvagqiptgwshkafgipddiasqvdrtslwalvsvaealm
magitdpyelykwihpsevgsslgsgmggitsiskmfrdrreekdvqkdilqetfintvagwvnllllssssgpikipvgac
atalqsveiacdtilsgkakimvsggyddfseegsyefanmkatsnsetefaagrepnemsrpttstragfmesmgcgaq
vlmsaktaiemgatiygivaytatatdkagrsipapgrgvmgtareitskypspildvtyrrrqlefrrkqisqwlenetellk
fevsshgqatklpddyvserlasiereakrqeaealatygmlagqdptiaplrralavwgltiddvgvasfhgtstvandkn
esnayneqfrhlgrakgnacpviaqkwltghpkggaaawmlnglaqviqsglvpgnrnadnigeelrafeyllypsksi
qtdgikaglltsfgfgqvggqalivhpslligalepaqfeaykklndqrkkwsyrrfndfftngklviikdgtpftpeqenttll
nplvravpdktgsysmpkefpatvprsnnaevanklvsaavggafgvgtdvelisavptsesflernftqdeiayckaapd
fraslaarwsakeatfkalkteskgaaasmqdievvstsqgptiklhgevekiaqaagitafevslshsedvacavviaqk

SEQ ID NO. 10:
>AkFAS_AA
meqhkteklsaadeklsestihwlaatdvpsnfvlfsgqgyqyfdelrelyetgtdevkgflllasktlqeeicsekaktvafk
fvneldftkwieedidvdqtyifsapvsfpliifvaqvarylqtlnllrtdhkqfiqtikgssghsqgivaavlistspdndrive
navklcrymlwqglrchessvnrfsgknhkskkskvysfdestrmvkyspmlavngltesllndfmkktesiiearrtiq
qkynrresffetptekdekskrlnmfqialangpksfvvsgapktieleqrikesttsspnsqtripfskrkpvvkmyflkv
gaafhteicndassklkadvvqmklsispkeilipvyhtkdgsnlseisadvnvvdllidmqtsqvndfrktlksissqngv
snvidfgpgdgtaklclkrksgtgilvvaatgplrnrrcaygrnlvglnsvlleknpilgmnwgeefkprlssrkndnqiiv
gtrfsdltgkppvilpgmtpttsfhgidlvaacsnggyhgelagglplpeyfkakidelvskqnsgvgininmlylnsyl
wgfqfstaiqmakdgypiesitcaagvpttekakeimhqlkeagikyiafkpgsraaimdvlsiarenpnssivlqwtggr
ggghhsfedfhaplldtyqeirehpnvvlvvgsgfgdaeksypyldgswstlpphncesrmpcdavlfgsrcmvakea
atspevkqlivnakgvreneswemsyendaggiltvtselgepihkinnrgmklwrefdrkyfslpsgqerekaivkdk
keiirrinadfqkvyfgrkadgtvvdiaymtygeilrrmvdlmyvtgggdgkqhrfapnrwidvtyqtrtfkflvrterrflr
dkkmafatdmrklesfpikcidefvkcypqvdkvlvsdedagyfielcrnlrngkpvnfipqidgslaywfkkdslwcs
eqidavpdndpgrvcilhgpvaaqysvvsdepiceilgnihkgyvdklkeekyevakvetigklpeykgsnksfrkflry
gwfnalfqstvmvkekkwvrniipgiiqtenenivfsertamndmclievllndsqrtlafiefegkhisvslqdsepvnst
ltlyfeyhpetphsplfqvtngsksiarsikqyyrniwdcqdvvsihdtfsesftvtredierfngaiqyavntsegtldfaiva
gwkslikalfskeidgslldlvhishsyklvveekertlvqagekicsesrvisvqilpgvgksitvkgvlsrntvkwvevqs
eflirgnffdfqktfkeysykaevlckddtvpqilnsqewlfldsgvrplskhdkvvfqidrvvekrksvtnisdilvagnv
vrintpeeidgfielkdqgspkgiiigkvdlslenanlsenpiityldsikesklhgsvfesggytvmprpelvtapsivesiv FIG. 10 (Continued)

yasasrdmnpihrnrtfaklaglpggstivhgmwtaamsrrilelhtvlgdhrristysvkftgmvfpedklavmvkhvg
vtegrlildvdvskvetqervlhgraevegpstsflftgqgsakvgmgmdsyeekqsaravwqtadkflrkkfgfsivdiv
knmpkeltvrfggsqgkvirenyraikredgsqlireihsnttsftfrspngllfatqfsqpalvlvqkaafeemlqggfvpsn
smfaghslgeyaalasyanvlsiedlvetvflrgmvmqnavarddegtsdygmvaanpsrvsktfsaqllmeivqkidd
esddshllqvvnfnirdaqyviagnlelldslsnvlnvisnshdktfdrsiiqaamikaenrrrsckennqpfrlkrgiatiplh
gidvpfhsrqllngvpafrslleprfteemiqkylprligkyipnvhaepfsiskeyiekvasvtkspalykllstystmcdss
karilliellahqfampvqwidtqdyilsrhtqriiemgpaptlvgmakktlqsriygdeedykpsilwwnqnqeeifynl
dnqgisiqqflqelkgteddesqsddmssytqsdetiqrtaknrvmpeanandkekvgnelqkkevtnrplhvlrvlistk
lkkkmlevkatdtikgvsggksaiqneligeinaeyssfrdiedisevslaelarrapsrqetvlgkvttkmvnkmfssklp
gkfgpndtkeylqsklsdastvdsvslhaltlqpvsrlatpgeaqawldsvcrdfendqrisilknkspnsnesvmiseqrt
vqnnfvqiseepvnskhvllslismklqkeissinetstikslvngksavqneilgeiasefrtdesegaadislselgeklgig
yagpgsvvsrhinkmlnsklpgsfnsssakkylsmqgfgkgrsdsvlvhaltmqpksrlqgvedakswldsvcssygk
wanidltvsrtlssgdsspahstkdilsstamkklkklyldqvdvfntflgedrraklqkvlteetsakdrieaqllelkeelgd
pfcdgiqpqfneaririydsywnwvvqdalelhyhtfscvlnskgknvnipnssnsyframsdwitssnekleenkppq
awfrnylcnratpelltvvqyfaarmneqghseyaqavsllaeqvsqwisrppvhialfasleprvtvdsannfglkyeek
prkfvavgenkafscdnaslyvkemskglfydhrvaskvehpsqsvylspdnsffpneeesdqissgmrlpktqgeiqr
dfsrlpagqklevmrksvnrssdtdeeianivrqnynsihvaknvplvhlkspskfdktvrvldepltsmylsclhdiatsg
vsfagqnalvtgagfgsigielikpllegatvlvtvrlnrtdeqmqivnerfqrlyeefgsrgsklvlvpcncasnqdvhsli
rhiyeklkldldfifpfaaigeqgkdvseigsksevahrlmltntirllgavkkakedrcietrpalvllpcspnhgdfgldgly
aesklgleslvnkwkseewgnylsicaavigwtrsklmwqnnvvaegieklgvrtfsttetafnligllhpdivshaaeepl
wadltgnwgaapdlkehskrirtsllaqskaakaislsskslviepseskṭkaqteivntylagvndklrlplanpekfcnpf
pkipsqermdslaylkhsvdlkkvvvvvgygeigpwgnsrtrwemesfgefslegaielawlvglikpvtgplkndprt
qyfgwvdaeseepvadheiktryekvllqhsgirliepelfegynpkkksilrqvaiaedmkpievasleeaqqyvnelg
kefidvfnenvesndgqwyirlkagavvsipgalsfnrfiagqlptgwdakrlgipddiadsvdpvtlyalvstvealvcag
ltdpyelyqyvhvsqvgntsgggmggmrslkrmflerkldaeipsdtlaesfintmpawvnmlllsssgpiktpvgacat
aaesvdigietilagkarvviaggyddfcetgsnefammgatsnsqteaekgrfpreasrpmtdtragfmesqgagmqvl
mdaelaiqmglpvygilalsntatdrqgrsvpapgrgilttarevrsknsksshngkpvenpllsvkfrkkhlrqeldaidl
wasqeisnmseefsqnsrkmenrkgfvetmrkkkrsaafetwgqgfyrnddsiaplrgalsvwgltvddllvgsfhgtgt
nlndtnesslvnkqlkhldrkegnillvvtqkyltghpkgaaaawmlngllqcmnsgrvpgnrnldnvdgklrtngylfy
pnrtievprveaaflksfgfgqagaevviihpdrllavlseenlksyilrrnerekrayryhqgvmsghhtmvqvkefapy
eddileeiylnprarasfdsskstwtfhkyrndkdtvddkdemeqdslnesvdlpkditkvgspseiripvktrlevtvreg
vegltkkdkfssqgvgvdvepvstfaqheektifiqnnfteneqlycnhaaspaasyagrwaakeavikaisnssletrsl
wqgaegklidieiiqsnsgapevvlhghakevfqtlgltnvkvsishtpevavaqaitn

SEQ ID NO. 11:
> RtFAS_ACPII2TE_AA
Mvaaqdlplalsisfapesstismtlfnqpeaskpalplelkykydpstpyapiheitedrnqrikqhywdlwglgnkad
qgisqlkitdefqgdlvtisadeieafcrvvgiegeaykrnhkagmqvpldfaiklgwkaimkpifpstidgdllklvhlsn
gfrvlpdtptlqvgdvvtttsriesitnsdtgktvsvrgvislvssadskgkdastedripllievtssffyrgkfsdyaqtfsrvah
ptysvpittpeavavlqskewfqwdddskplevgtklqfkvesnyvyadkssyamatvtggayvitpelklavkvatvd
ytsegegviqgdpvieylkrhgsaldqpimlenggysltkagqctfttpasnldysltsgdtnpihtnpyfaslaylpgtithg
mhssartrkfveqvaadnvgarvrkyevgftamclpsrkmevrlkhvgmtadgnrlikvetvdveggnvvlsgtaeva
qaptayvftgqgsqepgmgmelyanspvaravwdeadrhlgevygfsileivrtnpkektvhfgglkgqatrqkymd
msytttdhegnvktlplfgdidlrtsrytfssptgllyatqfaqialvvtekaafedmrakglvqkdcvfaghslgeysalasia
dilpisalvdvvfyrgitmqraverdhlnrssygmvavnpsrigksfgdaalrevvdtiarrgnilievvnynvegqqyvv aghlvalqsltnvlnflkiqkidlakltetmsieqvkehlceivdecvqkardlqaktgfitlergfatiplpgidvpfhsrylw
agvmpfrtylskkvnpahfnadllvgryipnltavhyevskeyaerihtqtssprlnkilkawdeerwgapenrnklgyai
liellayqfaspvrwietqdilfrdfkferlvelgpsptltgmatrtqklkydahdssvgikrsiyciakhqkeiyyqfddvag
eeapapaavapsapapkaapvaaapppppapvaaapaaavadeplkavdtlriiiaqklkkpvgevpltksikelvggkst
lqneilgdlqgefssapekgeemplqelgaalqqgysgklgkyttgvisrmigakmpggfglsavqghlgktyglgagri
dgvllfavtqepakrlanegeakawvdsvaqgyasmagislaagggaaaaapamafaapaaagggapaktililgdsls
agyginpeqgwvallqkrldqqfpkqhkvinasvsgettsgalarlpklIttyrpnvvvielggndalrgqppqmiqsnle
kliqhsqkakskvvvfgmkippnygtaysqafennykvvsqtyqvkllpffldgvaghkslmqndqihpnakaqsill
nnaypyikgalagggggggaavggagfminteqldkmqekqdnfvsqqvelflrylgkdsreghrladmqkaevanlq
ekldsiarehgdayvqgiqpvfdplkarhfnsswnwvrqdalmmwmdilfgrlttvdrditarclvimnradpslidym
qytidntpvergehyvlakqfgqqlldncremigqaplykdvtfptapkttvnakgdiiteevnrpgvsrlekyvaemaa
gskvtvasvnldkvqeqveklyklvksqpqiskqhmtsikslyaevvrglgkdagpppvhkagtrarrpssqflrpaavs
eatflpedkvpllhlkrkigndwqysskltslyldilkeiatsgvtfehknalmtgvgkgsigieivkgllaggarvvittsrys
rstveyyqaiyqevgskgssltvvpfnqgskqdvealvdfiyskdkglgmdldyilpfaalpengreidgiddrselahri
mltnllrllgavkskkaalklttrptevvlplspnhglfgndglyseskisletlfnrwsseswgeylclagavigwtrgtglm
satnsvaegieaqgcrtfsakemafnilglmhplvfdvaqiepvwadlnggmdklpdlanltteirkklnltastrraiakd
nsfdykvahgpameqihqrinvapranfslpfpelkpidakselaklrglidlekvvvmtgyaevgpfgssrtrwemea
ngtfsiqgtlelayvmglikhfegrlkdgtlyvgwvdaktnepIddkdvkaayekhilahtgirliepeifngydpkrkgft
qeieiqhdlepieaseedaarfkrehgalvdvytedgskffvkfkkgaklhipkavafdrlvagqiptgwshkafgipddi
asqvdrtslwalvsvaealmmagitdpyelykwihpsevgsslgsgmggitsiskmfrdrreekdvqkdilqetfintva
gwvnllllssssgpikipvgacatalqsveiacdtilsgkakimvsggyddfseegsyefanmkatsnsetefaagrepnem
srpttstragfmesmgcgaqvlmsaktaiemgatiygivaytatatdkagrsipapgrgvmgtareitskypspildvtyrr
rqlefrrkqisqwlenetellkfevsshgqatklpddyvserlasierakrqeaealatygmlagqdptiaplrralavwglti
ddvgvasfhgtstvandknesnayneqfrhlgrakgnacpviaqkwltghpkggaaawmlnglaqviqsglvpgnrna
dnigeelrafeyllypsksiqtdgikaglltsfgfgqvggqalivhpslligalepaqfeaykklndqrkkwsyrrfndffting
klviikdgtpftpeqenttllnplvravpdktgsysmpkefpatvprsnnaevanklvsaavggafgvgtdvelisavptse
sflernftqdeiayckaapdfraslaarwsakeatfkalkteskgaaasmqdievvstsqgptiklhgevekiaqaagitafe
vslshsedvacavviaqk SEQ ID NO. 12:
>AkFAS-ACPII2TE_AA
Meqhkteklsaadeklsestihwlaatdvpsnfvlfsgqgyqyfdelrelyetgtdevkgflllasktlqeeicsekaktvaf
kfvneldftkwieedidvdqtyifsapvsfpllfvaqvarylqtInllrtdhkqfiqtikgssghsqgivaavlistspdndriv
enavklcrymlwqglrchessvnrfsgknhkskkskvysfdestrmvkyspmlavngltesllndfmkktesiiearrti
qqkynrresffetptekdekskrlnmfqialangpksfvvsgapktlieleqrikesttsspnsqtripfskrkpvvkmyflk
vgaafhteicndasskIkadvvqmklsispkeilipvyhtkdgsnlseisadvnvvdllidmqtsqvndfrktlksissqng
vsnvidfgpgdgtaklclkrksgtgilvvaatgplrnrrcaygrnlvglnsvlleknpilgmnwgeefkprlssrkndnqii
vgtrfsdltgkppvilpgmtpttsfhgidlvaacsnggyhgelagggIplpeyfkakidelvskqnsgvgininmlylnsyl
wgfqfstaiqmakdgypiesitcaagvpttekakeimhqlkeagikyiafkpgsraaimdvlsiarenpnssivlqwtggr
ggghhsfedfhaplIdtyqeirehpnvvlvvgsgfgdaeksypyldgswstlpphncesrmpcdavlfgsrcmvakea
atspevkqlivnakgvreneswemsyendaggiltvtselgepihkinnrgmklwrefdrkyfslpsgqerekaivkdk
keiirrinadfqkvyfgrkadgtvvdiaymtygeilrrmvdlmyvtgggdgkqhrfapnrwidvtyqtrtfkflvrterrflr
dkkmafatdmrrklesfpikcidefvkcypqvdkvlvsdedagyfielcrnlrngkpvnfipqidgslaywfkkdslwcs
eqidavpdndpgrvcilhgpvaaqysvvsdepiceilgnihkgyvdklkeekyevakvetigklpeykgsnksfrkflry
gwfnalfqstvmvkekkwvrniipgiiqtenenivfsertamndmclievllndsqrtlafiefegkhisvslqdsepvnst ltlyfeyhpetphsplfqvtngsksiarsikqyyrniwdcqdvvsihdtfsesftvtredierfngaiqyavntsegtldfaiva
gwkslikalfskeidgslldlvhishsykllveekertlvqagekicsesrvisvqilpgvgksitvkgvlsrntvkwvevqs
eflirgnffdfqktfkeysykaevlckddtvpqilnsqewlfldsgvrplskhdkvvfqidrvvekrksvtnisdilvagnv
vrintpeeidgfielkdqgspkgiiigkvdlslenanlsenpiityldsikesklhgsvfesggytvmprpelvtapsivesiv
yasasrdmnpihrnrtfaklaglpggstivhgmwtaamsrrilelhtvlgdhrristysvkftgmvfpedklavmvkhvg
vtegrlildvdvskvetqervlhgraevegpstsflftgqgsakvgmgmdsyeekqsaravwqtadkflrkkfgfsivdiv
knnpkeltvrfggsqgkvirenyraikredgsqlireihsnttsftfrspngllfatqfsqpalvlvqkaafeemlqggfvpsn
smfaghslgeyaalasyanvlsiedlvetvflrgmvmqnavarddegtsdygmvaanpsrvsktfsaqllmeivqkidd
esddshllqvvnfnirdaqyviagnlelldslsnvlnvisnshdktfdrsiiqaamikaenrrrsckennqpfrlkrgiatiplh
gidvpfhsrqllngvpafrslleprfteemiqkylprligkyipnvhaepfsiskeyiekvasvtkspalykllstystmcdss
karilliellahqfampvqwidtqdyilsrhtqriiemgpaptlvgmakktlqsriygdeedykpsilwwnqnqeeifynl
dnqgisiqqflqelkgteddesqsddmssytqsdetiqrtaknrvmpeanandkekvgnelqkkevtnrplhvlrvlistk
lkkkmlevkatdtikgvsggksaiqneligeinaeyssfrdiediseevslaelarrapsrqetvlgkvttkmvnkmfssklp
gkfgpndtkeylqsklsdastvdsvslhaltlqpvsrlatpgeaqawldsvcrdfendqrisilknkspnsnesvmiseqrt
vqnnfvqiktililgdslsagyginpeqgwvallqkrldqqfpkqhkvinasvsgettsgalarlpkllttyrpnvvvielgg
ndalrgqppqmiqsnlekliqhsqkakskvvvfgmkippnygtaysqafennykvvsqtyqvkllpffldgvaghksl
mqndqihpnakaqsillnnaypyikgalrtlssgdsspahstkdilsstamkklkklyldqvdvfntflgedrraklqkvlte
etsakdrieaqllelkeelgdpfcdgiqpqfneaririydsywnwvvqdalelhyhtfscvlnskgknvnipnssnsyfra
msdwitssnekleenkppqawfrnylcnratpelltvvqyfaarmneqghseyaqavsllaeqvsqwisrppvhialfas
leprvtvdsannfglkyeekprkfvavgenkafscdnaslyvkemskglfydhrvaskvehpsqsvylspdnsffpnee
esdqissgmrlpktqgeiqrdfsrlpagqklevmrksvnrssdteeianivrqnynsihvaknvplvhlkspskfdktvr
vldepltsmylsclhdiatsgvsfagqnalvtgagfgsigielikplleggatvlvtvrlnrtdeqmqivnerfqrlyeefgsrg
sklvlvpcncasnqdvhslirhiyeklkldldfifpfaaigeqgkdvseigsksevahrlmltntirllgavkkakedrcietr
palvllpcspnhgdfgldglyaesklgleslvnkwkseewgnylsicaavigwtrsklmwqnnvvaegieklgvrtfstte
tafnliglllhpdivshaaeeplwadltgnwgaapdlkehskrirtsllaqskaakaislsskslviepsesktkaqteivntyla
gvndklrlplanpekfcnpfpkipsqermdslaylkhsvdlkkvvvvvgygeigpwgnsrtrwemesfgefslegaiel
awlvglikpvtgplkndprtqyfgwvdaeseepvadheiktryekvllqhsgirliepelfegynpkkksilrqvaiaedm
kpievasleeaqqyvnelgkefidvfnenvesndgqwyirlkagavvsipgalsfnrfiagqlptgwdakrlgipddiads
vdpvtlyalvstvealvcagltdpyelyqyvhvsqvgntsgggmggmrslkrmflerkldaeipsdtlaesfintmpawv
nmlllsssgpiktpvgacataaesvdigietilagkarvviaggyddfcetgsnefammgatsnsqteaekgrfpreasrp
mtdtragfmesqgagmqvlmdaelaiqmglpvygilalsntatdrqgrsvpapgrgilttarevrsknsksshngkpve
npllsvkfrkkhlrqeldaidlwasqeisnmseefsqnsrkmenrkgfvetmrkkkrsaafetwgqgfyrnddsiaplrg
alsvwgltvddllvgsfhgtgtnlndtnesslvnkqlkhldrkegnillvvtqkyltghpkgaaaawmlngllqcmnsgrv
pgnrnldnvdgklrtngylfypnrtievprveaaflksfgfgqagaevviihpdrllavlseenlksyilrrnerekrayryhq
gvmsghhtmvqvkefapyeddileeiylnprarasfdssksktwtfhkyrndkdtvddkdemeqdslnesvdlpkditk
vgspseiripvktrlevtvregvegltkkdkfssqgvgvdvepvstfaqheektifiqnnfteneqlycnhaaspaasyagr
waakeavikaisnssletrslwqgaegklidieiiqsnsgapevvlhghakevfqtlgltnvkvsishtpevavaqaitn

SEQ ID NO. 13:
> AcTesA_AA
ktililgdslsagyginpeqgwvallqkrldqqfpkqhkvinasvsgettsgalarlpkllttyrpnvvvielggndalrgqp
pqmiqsnlekliqhsqkakskvvvfgmkippnygtaysqafennykvvsqtyqvkllpffldgvaghkslmqndqih
pnakaqsillnnaypyikgal FIG. 10 (Continued)

SEQ ID NO. 14:
> ScFAS2_AA
mkpeveqelahilltellayqfaspvrwietqdvflkdfntervveigpsptlagmaqrtlknkyesydaalslhreilcysk
dakeiyytpdpselaakeeapakeeapaptpaasapapaaaapapvaaaapaaaaaeiadepvkaslllhvlvahklkksl
dsipmsktikdlvggkstvqneilgdlgkefgttpekpeetpleelaetfqdtfsgalgkqsssllsrlisskmpggftitvark
ylqtrwglpsgrqdgvllvalsnepaarlgseadakafldsmaqkyasivgvdlssaasasgaagagaaagaamidagal
eeitkdhkvlarqqlqvlarylkmdldngerkflkekdtvaelqaqldylnaelgeffvngvatsfsrkkartfdsswnwak
qsllslyfeiihgvlknvdrevvseainimnrsndalikfmeyhisntdetkgenyqlvktlgeqlienckqvldvdpvyk
dvakptgpktaidkngnityseeprekvrklsqyvqemalggpitkesqptieedltrvykaisaqadkqdissstrvefek
lysdlmkflesskeidpsqttqlagmdvedaldkdstkevaslpnkstisktvsstipretipflhlrkktpagdwkydrqls
slfldglekaafngvtfkdkyvlitgagkgsigaevlqgllqggakvvvttsrfskqvtdyyqsiyakygakgstlivvpfnq
gskqdvealiefiydtekngglgwdldaiipfaaipeqgielehidsksefahrimltnilrmmgcvkkqksargietrpaq
vilpmspnhgtfggdgmysesklsletlfnrwhseswanqltvcgaiigwtrgtglmsanniiaegiekmgvrtfsqke
mafnllglltpevvelcqkspvmadlngglqfvpelkeftaklrkelvetsevrkavsietalehkvvngnsadaayaqvei
qpraniqldfpelkpykqvkqiapaeleglldlervivvtgfaevgpwgsartrwemeafgefslegcvemawimgfis
yhngnlkgrpytgwvdsktkepvddkdvkakyetsilehsgirliepelfngynpekkemiqeviveedlepfeasketa
eqfkhqhgdkvdifeipetgeysvkllkgatlyipkalrfdrlvagqiptgwnaktygisddiisqvdpitlfvlvsvveafia
sgitdpyemykyvhvsevgncsgsgmggvsalrgmfkdrfkdepvqndilqesfintmsawvnmllisssgpiktpv
gacatsvesvdigvetilsgkaricivggyddfqeegsfefgnmkatsntleefehgrtpaemsrpattttrngfmeaqgagi
qiimqadlalkmgvpiygivamaatatdkigrsvpapgkgilttarehhssvkyaspnlnmkyrkrqlvtreaqikdwv
enelealkleaeeipsedqnefllertreihneaesqlraaqqqwgndfykrdpriaplrgalatygltiddlgvasfhgtstka
ndknesatinemmkhlgrsegnpvigvfqkfltghpkgaagawmmngalqilnsgiipgnrmadnvdkileqfeyvl
ypsktlktdgvravsitsfgfgqkggqaivvhpdylygaitedryneyvakvsareksaykffhngmiynklfvskehap
ytdeleedvyldplarvskdkksgsltfnskniqskdsyinantietakmienmtkekvsnggvgvdvelitsinvendtfi
ernftpqeieycsaqpsvqssfagtwsakeavfkslgvkslgggaalkdieivrvnknapavelhgnakkaaeeagvtdv
kvsishddlqavavavstkk

SEQ ID NO. 15:
> ScFAS2-TE-ACP
atgaagccggaagttgagcaagaattagctcatattttgctaactgaattgttagcttatcaatttgcctctcctgtgagatggattg
aaactcaagatgttttttgaaggattttaacactgaaagggttgttgaaatcggtccttctccaactttggctgggatggctcaaag
aaccttgaagaataaatacgaatcttacgatgctgctctgtctttacatagagaaatcttatgctattcgaaggatgccaaagagat
ttattataccccagatccatccgaactagctgcaaaggaagagcccgctaaggaagaagctcctgctccaactccagctgcta
gtgctcctgctcctgcagcagcagccccagctcccgtcgcggcagcagcccagctgcagcagctgctgaaagactat
attgatattgggtgactcattgtccgctggttatggtattaatcctgaacaaggttgggtcgccttattgcaaaagagattggatca
acaattcccaaagcaacataaagtaatcaatgcatctgtttcaggtgaaactacatctggtgctttggcaagattaccaaagttgtt
aaccacttacagacctaacgttgtcgtaattgaattgggtggtaacgacgccttaagaggtcaaccacctcaaatgatccaatca
aatttggaaaagttaatacaacactcccaaaaagctaagagtaaggttgtcgtattcggtatgaagatcccacctaactatggtac
agcatactctcaagccttcgaaaataactataaggttgtctcacaaacctaccaagtcaaattgttaccatttttcttggatggtgtt
gctggtcataagtccttaatgcaaaatgaccaaatccacccaaacgccaaagctcaagtatattgttgaacaacgcttaccctt
acatcaagggtgcattagccggcggtggagctgctgctgctgccccgcgatggcgttcgccgctccggccgcagctggc
ggtggagcgcccgctgccgatgaacctgtcaaggcttcccctattgttgcacgttttggttgctcacaagttgaagaagtcgttag
attccattccaatgtccaagacaatcaaagacttggtcggtggtaaatctacagtccaaaatgaaattttgggtgatttaggtaaa
gaatttggtactactcctgaaaaaccagaagaaactccattagaagaattggcagaaactttccaagatccttctctggagcatt
gggtaagcaatcttcctcgttattatcaagattaatctcatctaagatgcctggtggggtttactattactgtcgctagaaaatacttac aaactcgctggggactaccatctggtagacaagatggtgtccttttggtagctttatctaacgagcctgctgctcgtctaggttctg
aagctgatgccaaggctttcttggactccatggctcaaaaatacgcttccattgttggtgttgacttatcatcagctgctagcgcta
gtggtgctgccggtgcaggtgctgctgccggtgcagctatgatcgatgctggcgctctggaagaaataaccaaagaccacaa
ggttttggcgcgtcaacaactgcaagtattggctcgttatctaaaaatggacttggataacggtgaaagaaagttcttgaaagaa
aaggacactgttgctgaacttcaagctcagttggattacttgaatgccgaattaggtgaattctttgttaacggtgttgctacttcttt
ctctagaaaaaaggccagaaccttcgattcttcctggaactgggctaaacaatctttattatcattatactttgagataattcatggt
gtcttgaaaaacgttgatagagaggttgttagtgaagctatcaatatcatgaacagatctaacgatgctttgattaaattcatggaa
taccatatctctaacactgatgaaacaaaaggtgaaaactatcaattggttaaaactcttggtgagcagttgattgaaaactgtaa
acaagttttggatgttgatccagtttacaaagatgttgctaagcctaccggtccaaaaactgctattgacaagaacggtaacatta
catactcagaagagccaagagaaaaggttaggaaattatctcaatacgtacaagaaatggcccttggtggtccaatcaccaaa
gaatctcaacctactattgaagaggatttgactcgtgtttacaaggcaatcagtgctcaagctgataaacaagatatttccagctc
caccaggggttgaatttgaaaaactatatagtgatttgatgaagttcttggaaagctccaaagaaatcgatccttctcaaacaaccc
aattggccggtatggatgttgaggatgctttggacaaagattccaccaaagaagttgcttctttgccaaacaaatctaccatttcta
agacggtatcttcaactattccaagagaaactattccgttcttacatttgagaaagaagactcctgccggagattggaaatatgac
cgccaattgtcttctctttttcttagatggtttagaaaaggctgccttcaacggtgtcaccttcaaggacaaatacgtcttgatcactg
gtgctggtaaggggttctattggtgctgaagtcttgcaaggtttgttacaaggtggtgctaaggttgttgttaccacctctcgtttctct
aagcaagttacagactactaccaatccatttacgccaaatatggtgctaagggttctacttgattgttgttccattcaaccaaggtt
ctaagcaagacgttgaagctttgattgaatttatctacgacactgaaaagaatggtggtttaggttgggatctagatgctattattcc
attcgcggccattccagaacaaggtattgaattagaacatattgattctaagtctgaatttgctcatagaatcatgttgaccaatatc
ttaagaatgatggggttgtgtcaagaagcaaaaatctgcaagaggtattgaaacaagaccagctcaagtcattctaccaatgtctc
caaaccatggtactttcggtggtgatggtatgtattcagaatccaagttgtctttggaaactttgttcaacagatggcactctgaatc
ctgggccaatcaattaaccgtttgcggtgctattattggttggactagaggtactggtttaatgagcgctaataacatcattgctga
aggcattgaaaagatgggtgttcgtacttctctcaaaaggaaatggctttcaacttattgggtctattgactccagaagtcgtaga
attgtgccaaaaatcacctgttatggctgacttgaatggtggtttgcaatttgttcctgaattgaaggaattcactgctaaattgcgt
aaagagttggttgaaacttctgaagttagaaaggcagtttccatcgaaactgctttggagcataaggttgtcaatggcaatagcg
ctgatgctgcatatgctcaagtcgaaattcaaccaagagctaacattcaactggacttcccagaattgaaaccatacaaacaggt
taaacaaattgctcccgctgagcttgaaggtttgttggatttggaaagagttattgtagttaccggttttgctgaagtcggcccatg
gggttcggccagaacaagatgggaaatggaagcttttggtgaattttcgttggaaggttgcgttgaaatggcctggattatggg
cttcatttcataccataacggtaatttgaagggtcgtccatacactggttgggttgattccaaaacaaaagaaccagttgatgaca
aggacgttaaggccaagtatgaaacatcaatcctagaacacagtggtatcagattgatcgaaccagagttattcaatggttacaa
cccagaaaagaaggaaatgattcaagaagtcattgtcgaagaagacttggaaccatttgaggcttcgaaggaaactgccgaa
caatttaaacaccaacatggtgacaaagtggatatcttcgaaatcccagaaacaggagagtactctgttaagttactaaagggtg
ccacttatacattccaaaggctttgagatttgaccgttggttgcaggtcaaattccaactggttggaatgctaagacttatggtat
ctctgatgatatcatttctcaggttgacccaatcacattattcgttttggtctctgttgtggaagcatttattgcatctggtatcaccga
cccatacgaaatgtacaaatacgtacatgtttctgaggttggtaactgttctggttctggtatgggtggtgtttctgccttacgtggt
atgtttaaggaccgtttcaaggatgagcctgtccaaaatgatattttacaagaatcatttatcaacaccatgtccgctttgggttaata
tgttgttgatttcctcatctggtccaatcaagacacctgttggtgcctgtgccacatccgtggaatctgttgacattggtgtagaaac
catcttgtctggtaaggctagaatctgtattgtcggtggttacgatgatttccaagaagaaggctccttgagttcggtaacatgaa
ggccacttccaacactttggaagaatttgaacatggtcgtaccccagcggaaatgtccagacctgccaccactacccgtaacg
gttttatggaagctcaaggtgctggtattcaaatcatcatgcaagctgatttagctttgaagatgggtgtgccaatttacggtattgt
tgccatggctgctaccgccaccgataagattggtagatctgtgccagctccaggtaagggtattttaaccactgctcgtgaacac
cactccagtgttaagtatgcttcaccaaacttgaacatgaagtacagaaagcgccaattggttactcgtgaagctcagattaaag
attgggtagaaaacgaattggaagctttgaagttggaggccgaagaaattccaagcgaagaccaaaacgagttcttacttgaa
cgtaccagagaaatccacaacgaagctgaaagtcaattgagagctgcacaacaacaatggggtaacgacttctacaagagg
gacccacgtattgctccattgagaggagcactggctacttacggtttaactattgatgacttgggtgtcgcttcattccacggtac
atccacaaaggctaatgacaagaacgaatctgccacaattaatgaaatgatgaagcatttgggtagatctgaaggtaatcccgt FIG. 10 (Continued)

cattggtgttttccaaaagttcttgactggtcatccaaagggtgctgctggtgcatggatgatgaatggtgctttgcaaattctaaa
cagtggtattattccaggtaaccgtaacgctgataacgtggataagatcttggagcaatttgaatacgtcttgtacccatccaaga
ctttaaagaccgacggtgtcagagccgtgtccatcacttcttcggttttggtcaaaagggtggtcaagctattgtggttcatccag
actacttatacggtgctatcactgaagacagatacaacgagtatgtcgccaaggttagtgccagagagaaaagtgcctacaaat
tcttccataatggtatgatctacaacaagttgttcgtaagtaaagagcatgctccatacactgatgaattggaagaggatgtttactt
ggacccattagcccgtgtatctaaggataagaaatcaggctccttgactttcaactctaaaaacatccaaagcaaggacagttac
atcaatgctaacaccattgaaactgccaagatgattgaaaacatgaccaaggagaaagtctctaacggtggcgtcggtgtagat
gttgaattaatcactagcatcaacgttgaaaatgatactttatcgagcgcaatttcaccccgcaagaaatagagtactgcagcgc
gcagcctagtgtgcaaagctctttcgctgggacatggtccgccaaagaggctgttttcaagtccttaggcgtcaagtccttaggc
ggtggtgctgcattgaaagacatcgaaatcgtacgcgttaacaaaaacgctccagccgttgaactgcacggtaacgccaaaa
aggctgccgaagaagctggtgttaccgatgtgaaggtatctatttctcacgatgacctccaagctgtcgcggtcgccgtttctac
taagaaatag

SEQ ID NO. 16:
> ScFAS2-ACP-TE atgaagccggaagttgagcaagaattagctcatatttttgctaactgaattgttagcttatcaatttgcctctcctgtgagatggattg
aaactcaagatgttttttgaaggattttaacactgaaagggttgttgaaatcggtccttctccaactttggctgggatggctcaaag
aaccttgaagaataaatacgaatcttacgatgctgctctgtctttacatagagaaatcttatgctattcgaaggatgccaaagagat
ttattataccccagatccatccgaactagctgcaaaggaagagcccgctaaggaagaagctcctgctccaactccagctgcta
gtgctcctgctcctgcagcagcagcccccagctcccgtcgcggcagcagcccagctgcagcagctgctgagattgccgatg
aacctgtcaaggcttcccctattgttgcacgttttggttgctcacaagttgaagaagtcgttagattccattccaatgtccaagacaat
caaagacttggtcggtggtaaatctacagtccaaaatgaaattttgggtgatttaggtaaagaatttggtactactcctgaaaaac
cagaagaaactccattagaagaattggcagaaactttccaagataccttctctggagcattgggtaagcaatcttcctcgttattat
caagattaatctcatctaagatgcctggtgggtttactattactgtcgctagaaaatacttacaaactcgctggggactaccatctg
gtagacaagatggtgtccttttggtagctttatcaacgagcctgctgctcgtctaggttctgaagctgatgccaaggctttcttgg
actccatggctcaaaaatacgcttccattgttggtgttgacttatcatcagctgccggcggtggagctgctgctgctgccccgc
gatggcgttcgccgctccggccgcagctggcggtggagcgcccgctaagactatattgatattgggtgactcattgtccgctg
gttatggtattaatcctgaacaaggttgggtcgccttattgcaaaagagattggatcaacaattcccaaagcaacataaagtaatc
aatgcatctgtttcaggtgaaactacatctggtgctttggcaagattaccaaagttgttaaccacttacagacctaacgttgtcgta
attgaattgggtggtaacgacgccttaagaggtcaaccacctcaaatgatccaatcaaatttggaaaagttaatacaacactccc
aaaaagctaagagtaaggttgtcgtattcggtatgaagatcccacctaactatggtacagcatactctcaagccttcgaaaataa
ctataaggttgtctcacaaacctaccaagtcaaattgttaccattttcttggatggtgttgctggtcataagtccttaatgcaaaatg
accaaatccacccaaacgccaaagctcaaagtatattgttgaacaacgcttacccttacatcaagggtgcattagctggtgctag
cgctagtggtgctgccggtgcaggtgctgctgccggtgcagctatgatcgatgctggcgctctggaagaaataaccaaagac
cacaaggttttggcgcgtcaacaactgcaagtattggctcgttatctaaaaatggacttggataacggtgaaagaaagttcttga
agaaaaggacactgttgctgaacttcaagctcagttggattacttgaatgccgaattaggtgaattctttgttaacggtgttgcta
cttctttctctagaaaaaaggccagaaccttcgattcttcctggaactgggctaaacaatctttattatcattatactttgagataattc
atggtgtcttgaaaaacgttgatagagaggttgttagtgaagctatcaatatcatgaacagatctaacgatgctttgattaaattcat
ggaataccatatctctaacactgatgaaacaaaaggtgaaaactatcaattggttaaaactcttggtgagcagttgattgaaaact
gtaaacaagttttggatgttgatccagtttacaaagatgttgctaagcctaccggtccaaaaactgctattgacaagaacggtaac
attacatactcagaagagccaagagaaaaggttaggaaattatctcaatacgtacaagaaatggcccttggtggtccaatcacc
aaagaatctcaacctactattgaagaggatttgactcgtgtttacaaggcaatcagtgctcaagctgataaacaagatatttccag
ctccaccagggttgaatttgaaaaactatatagtgatttgatgaagttcttggaaagctccaaagaaatcgatccttctcaaacaa
cccaattggccggtatggatgttgaggatgctttggacaaagattccaccaaagaagttgcttctttgccaaacaaatctaccatt
tctaagacggtatcttcaactattccaagagaaactattccgttcttacatttgagaagaagactcctgccggagattggaaatat FIG. 10 (Continued)

gaccgccaattgtcttctcttttcttagatggtttagaaaaggctgccttcaacggtgtcaccttcaaggacaaatacgtcttgatca
ctggtgctggtaagggttctattggtgctgaagtcttgcaaggtttgttacaaggtggtgctaaggttgttgttaccacctctcgttt
ctctaagcaagttacagactactaccaatccatttacgccaaatatggtgctaagggttctactttgattgttgttccattcaaccaa
ggttctaagcaagacgttgaagctttgattgaatttatctacgacactgaaaagaatggtggtttaggttgggatctagatgctatt
attccattcgcggccattccagaacaaggtattgaattagaacatattgattctaagtctgaatttgctcatagaatcatgttgacca
atatcttaagaatgatgggttgtgtcaagaagcaaaaatctgcaagaggtattgaaacaagaccagctcaagtcattctaccaat
gtctccaaaccatggtactttcggtggtgatggtatgtattcagaatccaagttgtctttggaaactttgttcaacagatggcactct
gaatcctgggccaatcaattaaccgtttgcggtgctattattggttggactagaggtactggtttaatgagcgctaataacatcatt
gctgaaggcattgaaaagatgggtgttcgtactttctctcaaaaggaaatggctttcaacttattgggtctattgactccagaagtc
gtagaattgtgccaaaaatcacctgttatggctgacttgaatggtggtttgcaatttgttcctgaattgaaggaattcactgctaaat
tgcgtaaagagttggttgaaacttctgaagttagaaaggcagtttccatcgaaactgctttggagcataaggttgtcaatggcaat
agcgctgatgctgcatatgctcaagtcgaaattcaaccaagagctaacattcaactggacttcccagaattgaaaccatacaaa
caggttaaacaaattgctcccgctgagcttgaaggtttgttggatttggaaagagttattgtagttaccggttttgctgaagtcggc
ccatggggttcggccagaacaagatgggaaatggaagcttttggtgaattttcgttggaaggttgcgttgaaatggcctggatta
tgggcttcatttcataccataacggtaatttgaagggtcgtccatacactggttgggttgattccaaaacaaaagaaccagttgat
gacaaggacgttaaggccaagtatgaaacatcaatcctagaacacagtggtatcagattgatcgaaccagagttattcaatggt
tacaacccagaaaagaaggaaatgattcaagaagtcattgtcgaagaagacttggaaccatttgaggcttcgaaggaaactgc
cgaacaatttaaacaccaacatggtgacaaagtggatatcttcgaaatcccagaaacaggagagtactctgttaagttactaaa
gggtgccactttatacattccaaaggctttgagatttgaccgtttggttgcaggtcaaattccaactggttggaatgctaagacttat
ggtatctctgatgatatcatttctcaggttgacccaatcacattattcgttttggtctctgttgtggaagcatttattgcatctggtatca
ccgacccatacgaaatgtacaaatacgtacatgtttctgaggttggtaactgttctggttctggtatgggtggtgtttctgccttacg
tggtatgtttaaggaccgtttcaaggatgagcctgtccaaaatgatattttacaagaatcatttatcaacaccatgtccgcttgggtt
aatatgttgttgatttcctcatctggtccaatcaagacacctgttggtgcctgtgccacatccgtggaatctgttgacattggtgtag
aaaccatcttgtctggtaaggctagaatctgtattgtcggtggttacgatgatttccaagaagaaggctcctttgagttcggtaaca
tgaaggccacttccaacactttggaagaatttgaacatggtcgtaccccagcgggaaatgtccagacctgccaccactacccgta
acggttttatggaagctcaaggtgctggtattcaaatcatcatgcaagctgatttagctttgaagatgggtgtgccaatttacggta
ttgttgccatggctgctaccgccaccgataagattggtagatctgtgccagctccaggtaagggtatttttaaccactgctcgtgaa
caccactccagtgttaagtatgcttcaccaaacttgaacatgaagtacagaaagcgccaattggttactcgtgaagctcagatta
aagattgggtagaaaacgaattggaagctttgaagttggaggccgaagaaattccaagcgaagaccaaaacgagttcttactt
gaacgtaccagagaaatccacaacgaagctgaaagtcaattgagagctgcacaacaacaatggggtaacgacttctacaaga
gggacccacgtattgctccattgagaggagcactggctacttacggtttaactattgatgacttgggtgtcgcttcattccacggt
acatccacaaaggctaatgacaagaacgaatctgccacaattaatgaaatgatgaagcatttgggtagatctgaaggtaatccc
gtcattggtgttttccaaaagttcttgactggtcatccaaagggtgctgctggtgcatggatgatgaatggtgctttgcaaattctaa
acagtggtattattccaggtaaccgtaacgctgataacgtggataagatcttggagcaatttgaatacgtcttgtacccatccaag
actttaaagaccgacggtgtcagagccgtgtccatcacttctttcggttttggtcaaaagggtggtcaagctattgtggttcatcca
gactacttatacggtgctatcactgaagacagatacaacgagtatgtcgccaaggttagtgccagagagaaaagtgcctacaa
attcttccataatggtatgatctacaacaagttgttcgtaagtaaagagcatgctccatacactgatgaattggaagaggatgttta
cttggacccattagcccgtgtatctaaggataagaaatcaggctccttgactttcaactctaaaaacatccaaagcaaggacagt
tacatcaatgctaacaccattgaaactgccaagatgattgaaaacatgaccaaggagaaagtctctaacggtggcgtcggtgta
gatgttgaattaatcactagcatcaacgttgaaaatgatactttatcgagcgcaatttcaccccgcaagaaatagagtactgcag
cgcgcagcctagtgtgcaaagctctttcgctgggacatggtccgccaaagaggctgttttcaagtccttaggcgtcaagtcctta
ggcggtggtgctgcattgaaagacatcgaaatcgtacgcgttaacaaaaacgctccagccgttgaactgcacggtaacgcca
aaaaggctgccgaagaagctggtgttaccgatgtgaaggtatctatttctcacgatgacctccaagctgtcgcgggtcgccgtttc
tactaagaaatag FIG. 10 (Continued)

SEQ ID NO. 17:
> ScFAS2-TE-ACP_AA
mkpeveqelahilltellayqfaspvrwietqdvflkdfntervveigpsptlagmaqrtlknkyesydaalslhreilcysk
dakeiyytpdpselaakeepakeeapaptpaasapapaaaapapvaaaapaaaaaeiktililgdslsagyginpeqgwv
allqkrldqqfpkqhkvinasvsgettsgalarlpklIttyrpnvvvielggndalrgqppqmiqsnlekliqhsqkakskv
vvfgmkippnygtaysqafennykvvsqtyqvkllpffldgvaghkslmqndqihpnakaqsillnnaypyikgalag
ggaaaaapamafaapaaagggapaadepvkaslllhvlvahklkksldsipmsktikdlvggkstvqneilgdlgkefgt
tpekpeetpleelaetfqdtfsgalgkqsssllsrlisskmpggftitvarkylqtrwglpsgrqdgvllvalsnepaarlgsea
dakafldsmaqkyasivgvdlssaasasgaagagaaagaamidagaleeitkdhkvlarqqlqvlarylkmdldngerkf
lkekdtvaelqaqldylnaelgeffvngvatsfsrkkartfdsswnwakqsllslyfeiihgvlknvdrevvseainimnrs
ndalikfmeyhisntdetkgenyqlvktlgeqlienckqvldvdpvykdvakptgpktaidkngnityseeprekvrkls
qyvqemalggpitkesqptieedltrvykaisaqadkqdissstrvefeklysdlmkflesskeidpsqttqlagmdvedal
dkdstkevaslpnkstisktvsstipretipflhlrkktpagdwkydrqlsslfldglekaafngvtfkdkyvlitgagkgsiga
evlqgllqggakvvvttsrfskqvtdyyqsiyakygakgstlivvpfnqgskqdvealiefiydtekngglgwdldaiipfa
aipeqgielehidsksefahrimltnilrmmgcvkkqksargietrpaqvilpmspnhgtfggdgmysesklsletlfnrw
hseswanqltvcgaiigwtrgtglmsanniiaegiekmgvrtfsqkemafnllglltpevvelcqkspvmadlngglqfv
pelkeftaklrkelvetsevrkavsietalehkvvngnsadaayaqveiqpraniqldfpelkpykqvkqiapaelegIldle
rvivvtgfaevgpwgsartrwemeafgefslegcvemawimgfisyhngnlkgrpytgwvdsktkepvddkdvkak
yetsilehsgirliepelfngynpekkemiqeviveedlepfeasketaeqfkhqhgdkvdifeipetgeysvkllkgatlyi
pkalrfdrlvagqiptgwnaktygisddiisqvdpitlfvlvsvveafiasgitdpyemykyvhvsevgncsgsgmggvs
alrgmfkdrfkdepvqndilqesfintmsawvnmllissgpiktpvgacatsvesvdigvetilsgkaricivggyddfq
eegsfefgnmkatsntleefehgrtpaemsrpatttrngfmeaqgagiqiimqadlalkmgvpiygivamaatatdkigr
svpapgkgilttarehhssvkyaspnlnmkyrkrqlvtreaqikdwvenelealkleaeeipsedqnefllertreihneaes
qlraaqqqwgndfykrdpriaplrgalatygltiddlgvasfhgtstkandknesatinemmkhlgrsegnpvigvfqkflt
ghpkgaagawmmngalqilnsgiipgnrnadnvdkileqfeyvlypsktlktdgvravsitsfgfgqkggqaivvhpdy
lygaitedryneyvakvsareksaykffhngmiynklfvskehapytdeleedvyldplarvskdkksgsltfnskniqsk
dsyinantietakmienmtkekvsnggvgvdvelitsinvendtfiernftpqeieycsaqpsvqssfagtwsakeavfks
lgvkslgggaalkdieivrvnknapavelhgnakkaaeeagvtdvkvsishddlqavavavstkk

SEQ ID NO. 18:
> name: ScFAS2-ACP-TE_AA
mkpeveqelahilltellayqfaspvrwietqdvflkdfntervveigpsptlagmaqrtlknkyesydaalslhreilcysk
dakeiyytpdpselaakeepakeeapaptpaasapapaaaapapvaaaapaaaaaeiadepvkaslllhvlvahklkksl
dsipmsktikdlvggkstvqneilgdlgkefgttpekpeetpleelaetfqdtfsgalgkqsssllsrlisskmpggftitvark
ylqtrwglpsgrqdgvllvalsnepaarlgseadakafldsmaqkyasivgvdlssaagggaaaaapamafaapaaagg
gapaktililgdslsagyginpeqgwvallqkrldqqfpkqhkvinasvsgettsgalarlpklIttyrpnvvvielggndalr
gqppqmiqsnlekliqhsqkakskvvvfgmkippnygtaysqafennykvvsqtyqvkllpffldgvaghkslmqnd
qihpnakaqsillnnaypyikgalagasasgaagagaaagaamidagaleeitkdhkvlarqqlqvlarylkmdldnger
kflkekdtvaelqaqldylnaelgeffvngvatsfsrkkartfdsswnwakqsllslyfeiihgvlknvdrevvseainimnr
sndalikfmeyhisntdetkgenyqlvktlgeqlienckqvldvdpvykdvakptgpktaidkngnityseeprekvrkls
qyvqemalggpitkesqptieedltrvykaisaqadkqdissstrvefeklysdlmkflesskeidpsqttqlagmdvedal
dkdstkevaslpnkstisktvsstipretipflhlrkktpagdwkydrqlsslfldglekaafngvtfkdkyvlitgagkgsiga
evlqgllqggakvvvttsrfskqvtdyyqsiyakygakgstlivvpfnqgskqdvealiefiydtekngglgwdldaiipfa
aipeqgielehidsksefahrimltnilrmmgcvkkqksargietrpaqvilpmspnhgtfggdgmysesklsletlfnrw
hseswanqltvcgaiigwtrgtglmsanniiaegiekmgvrtfsqkemafnllglltpevvelcqkspvmadlngglqfv

FIG. 10 (Continued)

pelkeftaklrkelvetsevrkavsietalehkvvngnsadaayaqveiqpraniqldfpelkpykqvkqiapaeleglldle
rvivvtgfaevgpwgsartrwemeafgefslegcvemawimgfisyhngnlkgrpytgwvdsktkepvddkdvkak
yetsilehsgirliepelfngynpekkemiqeviveedlepfeasketaeqfkhqhgdkvdifeipetgeysvkllkgatlyi
pkalrfdrlvagqiptgwnaktygisddiisqvdpitlfvlvsvveafiasgitdpyemykyvhvsevgncsgsgmggvs
alrgmfkdrfkdepvqndilqesfintmsawvnmllisssgpiktpvgacatsvesvdigvetilsgkaricivggyddfq
eegsfefgnmkatsntleefehgrtpaemsrpatttrngfmeaqgagiqiimqadlalkmgvpiygivamaatatdkigr
svpapgkgilttarehhssvkyaspnlnmkyrkrqlvtreaqikdwvenelealkleaeeipsedqnefllertreihneaes
qlraaqqqwgndfykrdpriaplrgalatygltiddlgvasfhgtstkandknesatinemmkhlgrsegnpvigvfqkflt
ghpkgaagawmmngalqilnsgiipgnrnadnvdkileqfeyvlypsktlktdgvravsitsfgfgqkggqaivvhpdy
lygaitedryneyvakvsareksaykffhngmiynklfvskehapytdeleedvyldplarvskdkksgsltfnskniqsk
dsyinantietakmienmtkekvsnggvgvdvelitsinvendtfiernftpqeieycsaqpsvqssfagtwsakeavfks
lgvkslgggaalkdieivrvnknapavelhgnakkaaeeagvtdvkvsishddlqavavavstkk SEQ ID NO. 19:
>name: ScFAS1
atggacgcttactccacaagaccattaaccctatctcacggttctttagagcacgtgcttctggtaccaaccgcttcatttttcattg
cttcgcaattacaagaacaatttaataaaattttgcccgaacccactgaagggtttgctgcagatgacgagcctaccacacctgc
tgaactagtggggaaattccttggctacgtatcttctctagtcgaaccttccaaggtcggtcaattcgatcaggtcttgaaccttg
cttaacagaatttgaaaactgttatttagaaggcaatgacattcacgccttggctgctaaactattacaggaaaacgacacaacttt
agtgaagactaaagaactaattaaaaattatattaccgccagaataatggctaagagaccatttgacaaaaaatccaactctgct
cttttagggccgtcggcgagggtaacgcacaattggtagccattttcggtggtcaaggtaacaccgacgactactttgaagaat
tgcgtgatctatatcaaacttatcatgtcttagtgggagatttaatcaagttctccgctgaaactttaagtgaactgattagaactact
ttagatgctgaaaaagtctttactcaaggtttaaacatattggaatggttggagaacccttcaaatacccagacaaggactattta
ctttccattccaatttcatgccccttaattggtgtcattcaattggctcactacgtagttactgccaagcttttgggtttcactccaggt
gagttaagatcttacttaaaaggtgctacaggtcactctcaaggtttggttactgctgtcgccatagctgagacggattcctggga
atccttcttcgtctccgtaagaaaagcaattactgtattattcttcatcggtgttcgttgttacgaagcatacccaaacacttccctac
caccatccatcttggaagattccttggaaaacaatgaaggtgttccatctccaatgttgtccatttccaatctaactcaagaacaag
ttcaagactatgtaaataagactaactctcatttgccagctggtaaacaagttgaaatttctctagtcaatggtgcgaagaatctag
tcgtatcgggcccaccacaatcattatatggtttaaacttgactttaagaaaggccaaggccccatctggactggatcaatcaag
aatcccattcagcgaaagaaaattgaagttctccaataggttcttacctgttgcatcaccattccattcccatctattggttccagctt
cagatttgattaacaaagacttagtcaaaaacaatgtcagctttaacgctaaagatattcaaatccccgtttacgacacttttgatg
gttcagatctaagagtcctttcaggttccatttccgagagaatcgtcgactgcatcattagattacctgtcaaatgggaaactacta
cacaattcaaagccacccacatattagactttggtccaggtggagcttccggtttaggtgttttaacccatcgtaataaagatggt
actggtgttcgtgttatcgttgccggtactctcgacattaacccagatgatgattacggattcaagcaagaaatctttgatgttacta
gtaatggtttgaagaaaaatccaaactggttggaagaataccatccaaaattaattaagaacaaatcaggcaaaattttgtcgaa
acaaaattttctaaattaatcggtagaccacctttattggttcctggtatgacaccatgtactgtttctccagatttcgtagctgctacc
acaaatgctggttataccattgagttggccggtggtggttacttttccgcagcaggtatgaccgccgctattgattctgtggtttctc
agatagaaaagggtagtaccttcggtatcaacttgatctacgtcaatccatttatgttacaatggggtattccattaatcaaggaac
taagaagcaaaggttatccaattcaattcttgaccattggtgctggtgtcccatcattggaagttgctagtaatacatagagacat
taggtttgaagtacttgggtttgaaaccaggttccattgatgctatttcgcaagttataaacattgctaaagcacatccaaacttccc
aatagctttacaatggaccggtggtagaggtggtggtcatcattctttcgaagatgcccacactccaatgttacaaatgtactcca
agattagaagacatccaaacattatgttgatattcggttctggtttcggttctgctgatgacacttacccatacttaaccggtgaatg
gtccacaaaattcgattatccaccaatgccattcgatggtttcctatttggttcgagggtcatgattgctaaggaagttaaaacttct
cctgatgctaagaagtgtattgctgcttgtactggtgttcctgatgataaatgggaacaaacctacaagaagccaactggtggtat
tgtcactgttcgctctgaaatgggtgaaccaattcacaaaattgccactcgtggtgttatgctatggaaggaattcgacgaaacc atcttcaacttaccaaagaataagttggtaccaactttggaagcaaagagagattacattatctcaagattgaacgccgatttcca
aaaaccatggttgctaccgtcaacggtcaagcccgtgacctagccacaatgacatacgaagaagttgcaaagagattggtgg
aattaatgttcatcagatctaccaactcttggtttgatgtcacatggagaaccttactggtgatttcctacgtcgtgtcgaagaacg
tttcactaaaagtaagacattgtctttaatccaatcctattctctactagacaagcctgatgaagctattgaaaagtatttaatgctta
tcctgccgctagggaacagttcttgaatgcgcaagatattgatcactttttgagcatgtgtcaaaatccaatgcaaaaaccagtgc
cttttgttccagttttggatcgtagattcgagattttttcaaaaaagattcgttatggcaatctgagcacttggaagccgtcgtcgac
caagacgttcaaagaacatgtatcctacatggacctgttgcagcacaattcactaaagtcatcgatgaaccaattaagagcatta
tggatggtattcacgatggtcacatcaaaaagttactacatcaatattacggtgacgatgagtcaaagattccagcagttgagtac
tttggtggtgaaagccctgtagacgtacaaagtcaagttgattcttcctctgtatctgaagactcagctgtttttaaggcaacatcct
ctactgatgaagaaagctggtttaaggctttggcgggatccgaaattaactggagacatgcaagtttcttatgttcctttatcactc
aagataaaatgtttgtttctaacccaattagaaaagttttcaagccaagccaaggaatggttgttgagatttccaacggcaatactt
cttcaaagactgttgtcactctttcagaacctgttcaaggtgaattgaaaccaactgttattttgaagttgttgaaggagaacataat
ccaaatggaaatgattgagaacagaactatggatggtaagcccgtcagcttgccattgttgtacaacttcaacccagataatggt
tttgctccaatctctgaagttatggaggacagaaaccaaagaattaaggaaatgtactggaaattatggattgatgagcctttcaa
tttggactttgacccaagagatgtcattaagggcaaagatttcgagatcaccgctaaagaagtttatgactttacacacgctgttg
gaaacaattgtgaagacttcgtttctagacctgatagaacgatgttggccccaatggactttgctattgttgtcggatggagagcc
atcatcaaggccatttccctaatacggtcgatggtgacttattgaagttggttcatttgtctaacggctacaagatgattcctggcg
ctaagccactgcaagttggtgatgttgtttcaactactgctgttattgaatctgtcgtcaaccaacctacaggaaagattgtcgatg
tggtaggtacattatcgagaaatggcaagcctgtcatggaagtcacctcctcattcttctacagaggcaactatactgactttgaa
aacactttccaaaagactgttgaacctgtttatcaaatgcacatcaaaacttctaaagatatagctgtcttgcgctctaaggagtgg
ttccaattggacgatgaagacttcgatctgttaaacaaaactttgactttcgaaactgaaactgaagttacttcaagaatgctaac
atcttctcttcagtgaaatgttttggcccaattaaagttgaattgccaaccaaagaaaccgtggagatcggtattgtcgattacgaa
gccggtgcctctcacggtaaccctgttgttgatttcttgaagagaaacggttccacattggaacaaaaggtcaatctagaaaatc
ctattccaattgcagtacttgattcgtacactccaagtaccaacgaaccatacgctagagtttctggtgatttgaatccaattcacgt
ttcacgtcattttgcctcttacgcaaacttgccaggtactatcacgcacggtatgttttcttctgcttccgtccgtgctttgattgaaaa
ctgggctgctgacagtgtttcatccagggtacgtggctacacttgtcaatttgttgacatggttttgcctaacactgctttgaaaaca
tcgattcaacatgttggtatgatcaatggtagaaaattgataaagtttgaaactagaaatgaagatgacgttgtagttttgactggt
gaagccgaaattgaacaacctgttactaccttcgttttcactggtcaaggttcacaagaacaaggtatgggtatggacttatacaa
aacttctaaagctgctcaagatgtttggaatagagctgacaaccatttcaaggacacttatggtttctctatcttagacattgtcatta
acaacccagttaacttaacaattcacttcggtggtgaaaagggtaagaggatcagagaaaactattctgctatgatctttgagact
atcgtggatggaaaattgaagactgaaaaaattttcaaggaaattaatgagcacagtacttcttacacatttagatctgaaaaagg
tttattgtctgctactcaatttacacaaccagctttaactttgatggaaaaagctgctttcgaagacttgaaatctaaaggtttgatcc
cagccgatgctactttgctggtcactctttaggtgagtatgctgctttggcctcttggctgatgttatgtctatcgaatcttagttg
aagttgtgttctacagaggtatgactatgcaagttgctgttccaagagatgagttgggcagatccaactatggtatgattgccatta
acccaggtagagtcgctgcatcattctctcaagaagctttgcaatatgttgttgagagagttggtaagagaaccggctggttggtt
gaaatcgtcaactacaacgttgaaaaccaacaatatgttgcagctggtgatctaagagctttagacaccgttaccaatgttctaaa
cttcatcaaattacaaaaaattgatattattgaactacaaaagtcctatctttggaagaagttgaaggtcatttgtttgagatcattga
cgaagcttccaagaaatctgctgtcaagcctcgcccacttaaattggagagaggttttgcttgtatcccattagttggtatttctgtt
cctttccattccacctacttgatgaatggtgttaaaccattcaagagtttcttgaagaagaatatcataaaagaaaatgtgaaggtt
gctagattggccggaaagtacattccaaacttgactgcaaaaccattccaggttactaaggaatatttccaggacgtttatgattt
gactggctccgaacctatcaaggaaatcatcgacaactgggaaaagtatgaacaatcctaa SEQ ID NO. 20:
> name: ScFAS1_AA
Mdaystrpltlshgslehvllvptasffiasqlqeqfnkilpeptegfaaddepttpaelvgkflgyvsslvepskvgqfdqvl nlcltefencylegndihalaakllqendttlvktkeliknyitarimakrpfdkksnsalfravgegnaqlvaifggqgntdd
yfeelrdlyqtyhvlvgdlikfsaetlselirttldaekvftqglnilewlenpsntpdkdyllsipiscpligviqlahyvvtakl
lgftpgelrsylkgatghsqglvtavaiaetdswesffvsvrkaitvlffigvrcyeaypntslppsiledslennegvpspml
sisnltqeqvqdyvnktnshlpagkqveislvngaknlvvsgppqslyglnltlrkakapsgldqsripfserklkfsnrflp
vaspfhshllvpasdlinkdlvknnvsfnakdiqipvydtfdgsdlrvlsgsiserivdciirlpvkwetttqfkathildfgp
ggasglgvlthrnkdgtgvrvivagtldinpdddygfkqeifdvtsnglkknpnwleeyhpkliknksgkifvetkfskli
grppllvpgmtpctvspdfvaattnagytielaggggyfsaagmtaaidsvvsqiekgstfginliyvnpfmlqwgiplikel
rskgypiqfltigagvpslevaseyietlglkylglkpgsidaisqviniakahpnfpialqwtggrggghhsfedahtpml
qmyskirrhpnimlifgsgfgsaddtypyltgewstkfdyppmpfdgflfgsrvmiakevktspdakkciaactgvpdd
kweqtykkptggivtvrsemgepihkiatrgvmlwkefdetifnlpknklvptleakrdyiisrlnadfqkpwfatvngq
ardlatmtyeevakrlvelmfirstnswfdvtwrtftgdflrrveerftksktlsliqsyslldkpdeaiekvfnaypaareqfl
naqdidhflsmcqnpmqkpvpfvpvldrrfeiffkkdslwqsehleavvdqdvqrtcilhgpvaaqftkvidepiksim
dgihdghikkllhqyygddeskipaveyfggespvdvqsqvdsssvsedsavfkatsstdeeswfkalagseinwrhas
flcsfitqdkmfvsnpirkvfkpsqgmvveisngntssktvvtlsepvqgelkptvilkllkeniiqmemienrtmdgkp
vslpllynfnpdngfapisevmedrnqrikemywklwidepfnldfdprdvikgkdfeitakevydfthavgnncedfv
srpdrtmlapmdfaivvgwraiikaifpntvdgdllklvhlsngykmipgakplqvgdvvsttaviesvvnqptgkivdv
vgtlsrngkpvmevtssffyrgnytdfentfqktvepvyqmhiktskdiavlrskewfqlddedfdllnktltfetetevtfk
nanifssvkcfgpikvelptketveigivdyeagashgnpvvdflkrngstleqkvnlenpipiavldsytpstnepyarvs
gdlnpihvsrhfasyanlpgtithgmfssasvralienwaadsvssrvrgytcqfvdmvlpntalktsiqhvgmingrkli
kfetrneddvvvltgeaeieqpvttfvftgqgsqeqgmgmdlyktskaaqdvwnradnhfkdtygfsildivinnpvnlt
ihfggekgkrirenysamifetivdgklktekifkeinehstsytfrsekgllsatqftqpaltlmekaafedlkskglipadatf
aghslgeyaalasladvmsieslvevvfyrgmtmqvavprdelgrsnygmiainpgrvaasfsqealqyvvervgkrtg
wlveivnynvenqqyvaagdlraldtvtnvlnfiklqkidiielqkslsleeveghlfeiideaskksavkprplklergfaci
plvgisvpfhstylmngvkpfksflkkniikenvkvarlagkyipnltakpfqvtkeyfqdvydltgsepikeiidnweky
eqs FIG. 10 (Continued)

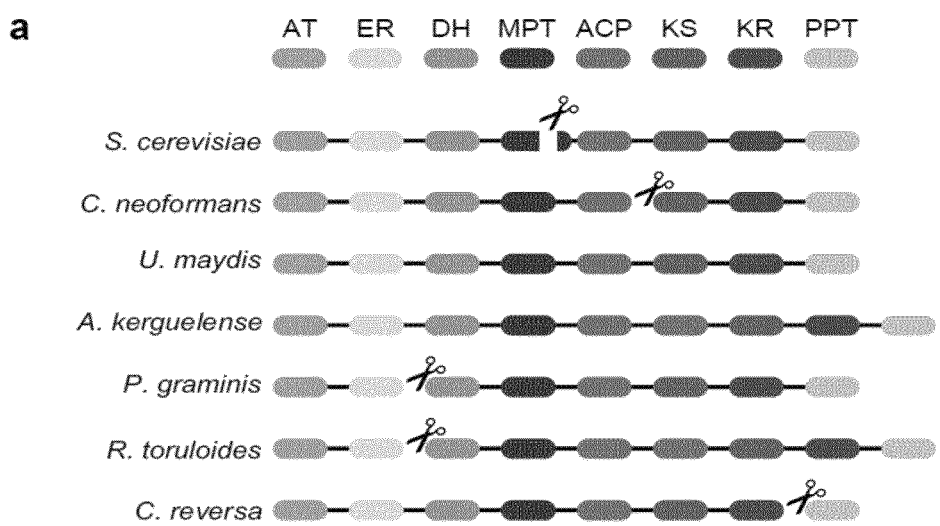
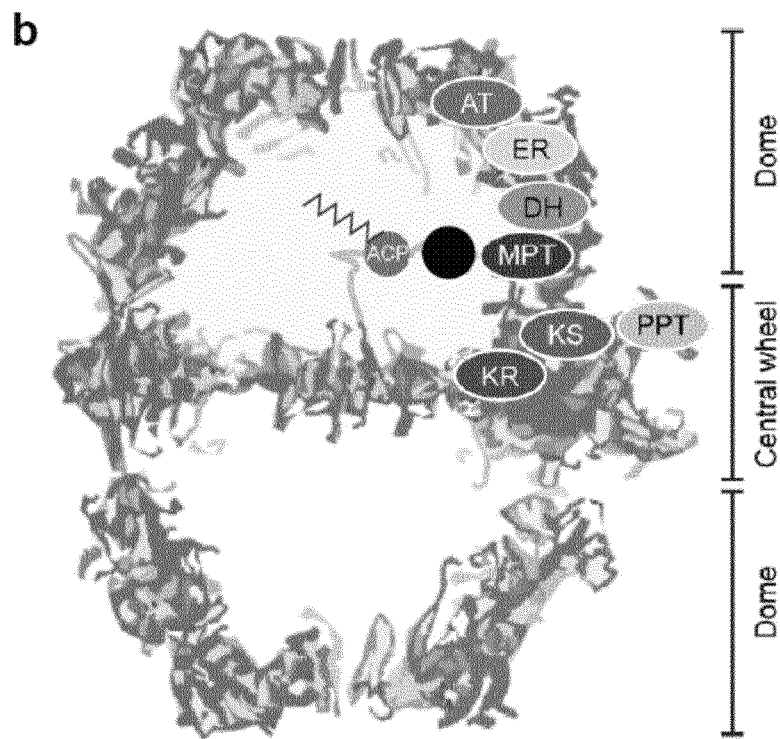
FIG. 11 a
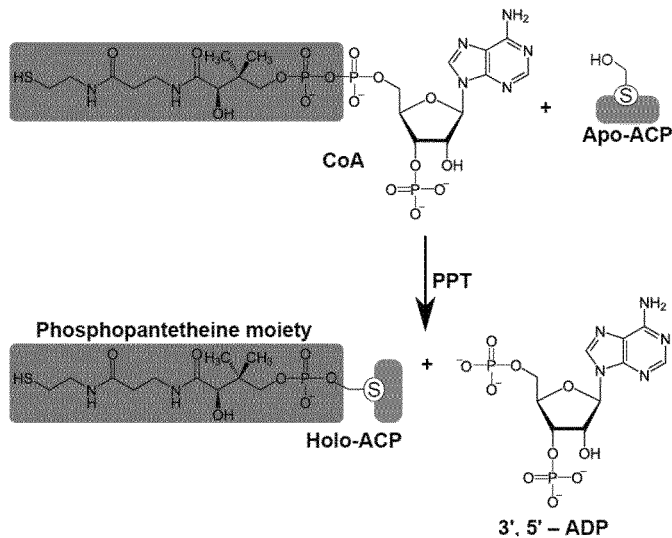
b
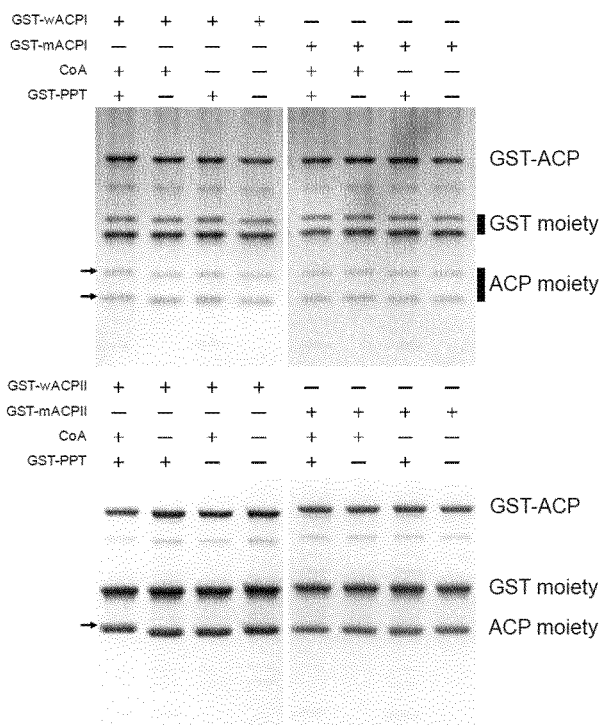
FIG. 12 a
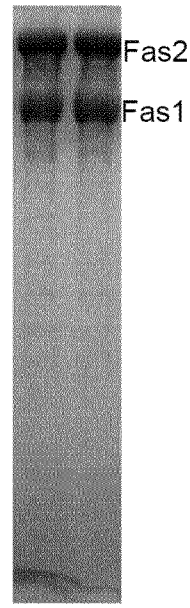
b
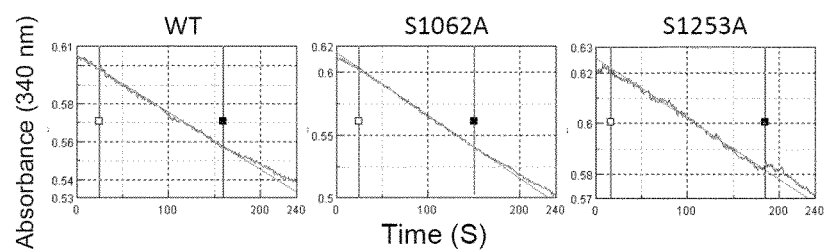
FIG. 13

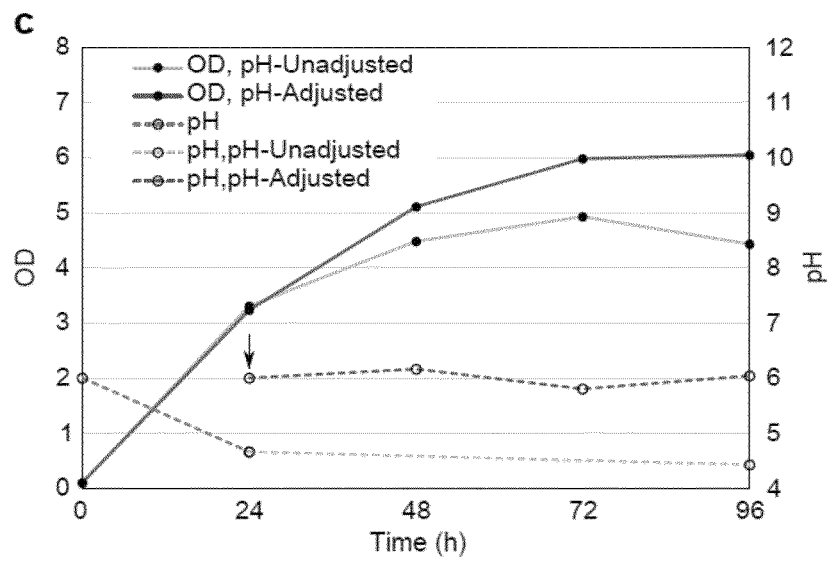
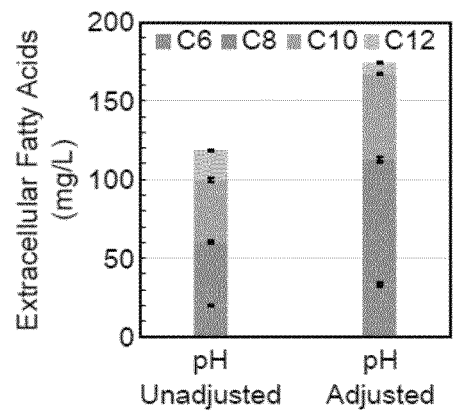
FIG. 17 (CONTINUED)

METHOD OF PRODUCING FATTY ACIDS

CROSS-REFERENCE TO RELATED APPLICATIONS

This application is a § 371 national phase of International Application No. PCT/EP2017/053811, filed on Feb. 20, 2017, which claims the benefit of European Patent Application No. 16158805.8, filed on Mar. 4, 2016, which applications are incorporated by reference herein.

FIELD OF THE INVENTION

The present invention relates to the field of fatty acid production, in particular production of short/medium chain fatty acids (S/MCFA) and derived products such as hydrocarbons, fatty aldehydes, and fatty alcohols. The present invention provides hereto genetic constructs and host cells, methods for producing such as well as methods for using such.

BACKGROUND OF THE INVENTION

Short/medium chain fatty acids (S/MCFAs, e.g. C6-C12) are precursors of many industrial chemicals and biofuels. The main source of S/MCFA is coming from refining of vegetable oil and fossil oil, but world availability is limited for these compounds while consumption is increasing. Therefore, it is of special interest to find new source for these products and in the same time to produce these kinds of fatty acids in a sustainable way by transformation of biomass-based materials by microbes.

The natural process of microbial fatty acid synthesis proceeds via a stepwise addition of two carbon units onto a growing acyl chain bound to acyl carrier protein (ACP). The process begins as a condensation of acetyl-ACP and malonyl-ACP into acetoacetyl-ACP liberating $CO_2$ which drives the reaction forward. The second step involves reduction of acetoacetyl-ACP to D-3-hydroxybutyryl-ACP using NADPH. Following a dehydration to crotonyl-ACP and another reduction using NADPH, butyryl-ACP is formed. The chain elongation typically continues with further addition of malonyl-ACP until an acyl chain of certain length is formed, which is then hydrolyzed by a thioesterase into a free fatty acid.

Recently, most efforts for chain length control were focused on the fatty acid synthesis or reversal of β-oxidation, and the targets for limiting acyl chain elongation are the enzymes responsible for condensation (ketoacyl-ACP synthase and thiolase) or product release (acyl-ACP/CoA thioesterase).

The reversal of the β-oxidation was first established in *E. coli*, and individual functional parts of this pathway were identified. However, this pathway prefers to produce short chain carboxylic acid (butyric acid). Further engineering involves using another thiolase (such as BktB) able to condense acetyl-CoA with C4-C8 acyl-CoA intermediates to produce medium chain fatty acids. The titers in *E. coli* were more than 1 g/L (C6-C10). Recently, after testing more than 40 enzymes, the reversed β-oxidation was realized in yeast, although the capacity is much lower than that in *E. coli*.

In prokaryotes, the dissociated type II fatty acid synthases are used. The end product of fatty acid synthesis is acyl-ACP. A common strategy for producing S/MCFA is expression of short chain acyl-ACP thioesterases, which release S/MCFA from ACP thioester. The short/medium chain acyl-ACPs, the substrates of thioesterases, are also incorporated into long chain fatty acid synthesis. So a cerulenin resistant β-ketoacyl-ACP synthase mutant (FabF*) with lower affinities to medium/long chain acyl-ACP (C8-C14) was used to block the incorporation of short/medium chain acyl-ACPs. Combined strategies used in *E. coli* resulted in titers of 118 mg/L C8 fatty acid.

From the above it is clear that various strategies are investigated and employed in order to produce fatty acids, such as S/MCFA, in particular microbial production of fatty acids. There however remains a need in the art for new and improved methods for fatty acid production, such as S/MCFA. The present invention provides hereto a solution.

SUMMARY OF THE INVENTION

The present invention relates to methods and means for producing or involving the production of fatty acids. The present invention in particular relates to engineering of an organism (for instance yeast, algae . . . ) for production of fatty acids, such as short and medium-chain fatty acids. According to the invention, a Fatty Acid Synthase (FAS), such as preferably a fungal FAS, or a subunit thereof, is engineered by introducing a Thioesterase (TE) resulting in production of fatty acids, in particular short or medium-chain fatty acids (S/MCFA). The present invention focuses on the specific combination of a modified fungal FAS (subunit) with a TE, in particular a heterologous TE, to obtain in particular fatty acids with custom carbon chain length (e.g. from C6 to C12).

According to the invention, a Fatty Acid Synthase (FAS), such as preferably a fungal FAS, or a subunit thereof, without a Thioesterase (TE) domain is complemented with a Thioesterase domain or is engineered by adding a Thioesterase (TE) domain, preferably before or after an Acyl Carrier Protein (ACP) domain (i.e. adjacent an ACP domain) resulting is production of fatty acids, in particular short or medium-chain fatty acids (S/MCFA).

Underlying the present invention is the use of a modified fungal fatty acid synthase (FAS), or a subunit thereof. The present inventions have surprisingly found that the complementation of a FAS with a TE or addition of a TE domain to FAS (subunit) devoid of such TE domain, such as before of after an existing ACP domain allows to tailor fatty acid length, without otherwise affecting or interfering with its fatty acid synthesis function. This finding is all the more surprising for type I FAS, in which individual enzyme domains are encoded as a single (or as two subunit) large multifunctional polypeptide(s). The individual FAS domains are covalently linked and thus structurally constrained. Unexpectedly, in such setting, the introduction of another domain (i.e. TE) not only does not perturb fatty acid synthesis, but moreover allows tailoring of fatty acid chain length. Moreover, some fungal FAS (subunit) genes have been found to encode multiple ACP domains. Advantageously, the present inventors have found that it is possible not only to delete or inactivate one of these duplicated ACP domains without loss of functionality, but additionally that functionality can be altered by replacement of one such ACP domain by a TE domain. The maintained functionality of such modified FAS (subunit) according to the invention is all the more surprising, as typically, the ACP(s) are situated internally in the FAS, such that providing an additional TE for instance directly up- or downstream of an ACP could not have been expected not to alter or in particular deteriorate FAS (subunit) structure and activity.

The invention is particularly captured by the appended claims, which are hereby explicitly incorporated by reference.

In an aspect, the invention relates to a recombinant polynucleic acid encoding a fatty acid synthase (FAS) or a FAS subunit, in particular fungal, in particular yeast, protist, myxomycete, or algae, in particular microalgae FAS, and a thioesterase (TE), which in certain preferred embodiments are encoded as a single ORF, and/or wherein said TE may be provided directly 5' or 3' relative to an acyl carrier protein (ACP) of said FAS (subunit).

In a further aspect, the invention relates to a recombinant prokaryotic or eukaryotic cell comprising, expressing or capable of expressing, such as inducibly or contitutively expressing, a fatty acid synthase (FAS) or a FAS subunit (such as FAS1 and/or FAS2), in particular fungal, in particular yeast, protist, myxomycete, or algae, in particular microalgae FAS, and a (heterologous) thioesterase (TE), which in certain embodiments are encoded as a single ORF, and/or wherein said TE may be provided directly 5' or 3' (or N-terminal or C-terminal) relative to an acyl carrier protein (ACP) of said FAS (subunit).

It is to be understood that according to the invention, the naturally occurring FAS (subunit) is devoid of TE, and hence the FAS (subunit) may be engineered to additionally comprise or contain a TE or alternatively that the FAS is complemented with a TE, such that for instance a recombinant cell according to the invention as described herein comprises, expresses or is capable of expressing a FAS and a TE.

Accordingly, in an aspect, the invention relates to a recombinant prokaryotic or eukaryotic cell comprising, expressing or capable of expressing or polynucleic acid comprising a fatty acid synthase (FAS) or FAS subunit gene sequence originating from a naturally occurring FAS (subunit) gene devoid of Thioesterase domain (TE) encoding nucleotide sequences, wherein a heterologous thioesterase domain (TE) encoding nucleotide sequences is added to said FAS (subunit), preferably before of after (i.e. 5' or 3') an acyl carrier protein domain (ACP) encoding nucleotide sequence.

In a further aspect, the invention relates to a recombinant prokaryotic or eukaryotic cell comprising, expressing or capable of expressing or polynucleic acid comprising a fatty acid synthase (FAS) or FAS subunit gene sequence originating from a FAS (subunit) gene, such as a naturally occurring FAS (subunit) gene, such as a fungal FAS (subunit) in particular yeast, protist, myxomycete, or algae, in particular microalgae FAS (subunit) gene, having at least two acyl carrier protein (ACP) encoding nucleotide sequences, wherein one of said ACP encoding nucleotide sequences is replaced by a thioesterase (TE) encoding nucleotide sequence.

The invention in related aspects also concerns polypeptides encoded by the recombinant polynucleic acid as defined herein, as well as vectors and host cells, such as prokaryotic or eukaryotic host cells, comprising the polynucleic acid as defined herein.

In an alternative aspect, the invention relates to a recombinant prokaryotic or eukaryotic host cell comprising a FAS (subunit) gene sequence originating from a fungal FAS (subunit) gene and additionally encoding a TE encoding nucleotide sequence. Accordingly, the invention also relates to a recombinant host cell comprising a FAS (subunit) gene sequence originating from a naturally occurring FAS (subunit) gene devoid of thioesterase (TE) domain encoding nucleotide sequences, wherein a heterologous thioesterase (TE) domain encoding nucleotide sequences is added to said FAS (subunit), preferably before of after (i.e. 5' or 3') the acyl carrier protein domain (ACP) encoding nucleotide sequence. In an alternative embodiment, said TE is not intergrated in said FAS (subunit) encoding nucleotide sequence. Accordingly, in certain embodiments, the invention relates to a recombinant prokaryotic or eukaryotic host cell comprising a FAS (subunit) gene sequence originating from a fungal FAS (subunit) gene and additionally encoding a TE encoding nucleotide sequence, wherein said TE encoding nucleic acid sequence is located at a different locus than said FAS encoding nucleic acid sequence. In certain embodiments, said FAS and/or said TE are genomically integrated. In certain embodiments, said FAS and/or said TE are episomal, such as provided on a vector.

In related aspects, the invention concerns methods for producing a recombinant prokaryotic or eukaryotic cell as described herein. In certain embodiments, the method comprises the step of introducing in a prokaryotic or eukaryotic cell the recombinant polynucleic acid, polypeptide, or vector as described herein, as well as the use of such cells for producing fatty acids, as well as derivatives thereof, such as hydrocarbons and fatty alcohols and related methods for producing fatty acids, involving the use of such cells.

In derived further aspects, the invention also relates to methods for producing hydrocarbons, such as alkanes or alkenes, or fatty alcohols or fatty aldehydes involving simultaneous or downstream conversion of the fatty acids as produced according to the methods as described herein, in particular involving reduction, hydrogenation, decarboxylation or decarbonylation of the fatty acids.

BRIEF DESCRIPTION OF THE FIGURES

FIG. 1. Domain architecture of the fungal type I FAS. There are eight distinct protein domains in fungal type I FAS, that is, acetyltransferase (AT), enoyl reductase (ER), dehydratase (DH), malonyl/palmitoyl transferase (MPT), acyl carrier protein (ACP), ketoacyl synthase (KS), ketoacyl reductase (KR), phosphopantetheinyl transferase (PPT). Unlike to the FAS from *Saccharomyces cerevisiae*, the FASs from *Rhodosporidium toruloides* and *Aplanochytrium kerguelense* contain two tandem ACP domains, and either the first or the second ACP domains was replaced by a thioesterase (TE) domain. In the FAS from *Saccharomyces cerevisiae*, such a heterogenous acyl-ACP thioesterase (TE) domain was inserted into regions upstream or downstream of the ACP domain. These kinds of modified FASs containing TE domain were used to produce tailored medium chain fatty acids.

FIG. 10. Sequences suitable for use in embodiments according to the invention.

FIG. 12. In vitro phosphopantetheinylation of ACP domains from *R. toroloides* fatty acid synthase by cognate PPT. (a) Phosphopantetheinylation reaction catalyzed by phosphopantetheinyl transferase (PPT). The phosphopantetheine moiety of coenzyme A (CoA) is transferred to the hydroxyl group of serine residue of acyl-carrier protein (ACP). (b) SDS-PAGE analysis of the phosphopantetheinylation products. wACP I (RtFas2, 1022-1184), wACPII (RtFas2, 1213-1375) and PPT (RtFas2, 2809-2928) were expressed and purified as GST fusion proteins. In mACPI and mACPII, the corresponding serine was mutated to alanine as shown in (b). The phosphopantetheinylation reaction mixture was cleaved by enterokinase and separated by 16% Tricine-SDS-PAGE. The phosphopantetheinylated ACPs with slightly higher molecule weight than the apo-ACP were shown by arrows.

FIG. 13. In vitro enzyme activity assay of the purified RtFAS complex. (a) SDS-PAGE analysis of the purified RtFAS complex, two subunits was separated as indicated. (b) Enzymatic activity assay of the purified RtFAS and its mutants. The malonyl-CoA and acetyl-CoA dependent NADPH oxidation was monitored by decrease of absorption at 340 nm.

DETAILED DESCRIPTION OF THE INVENTION

Figure 2:
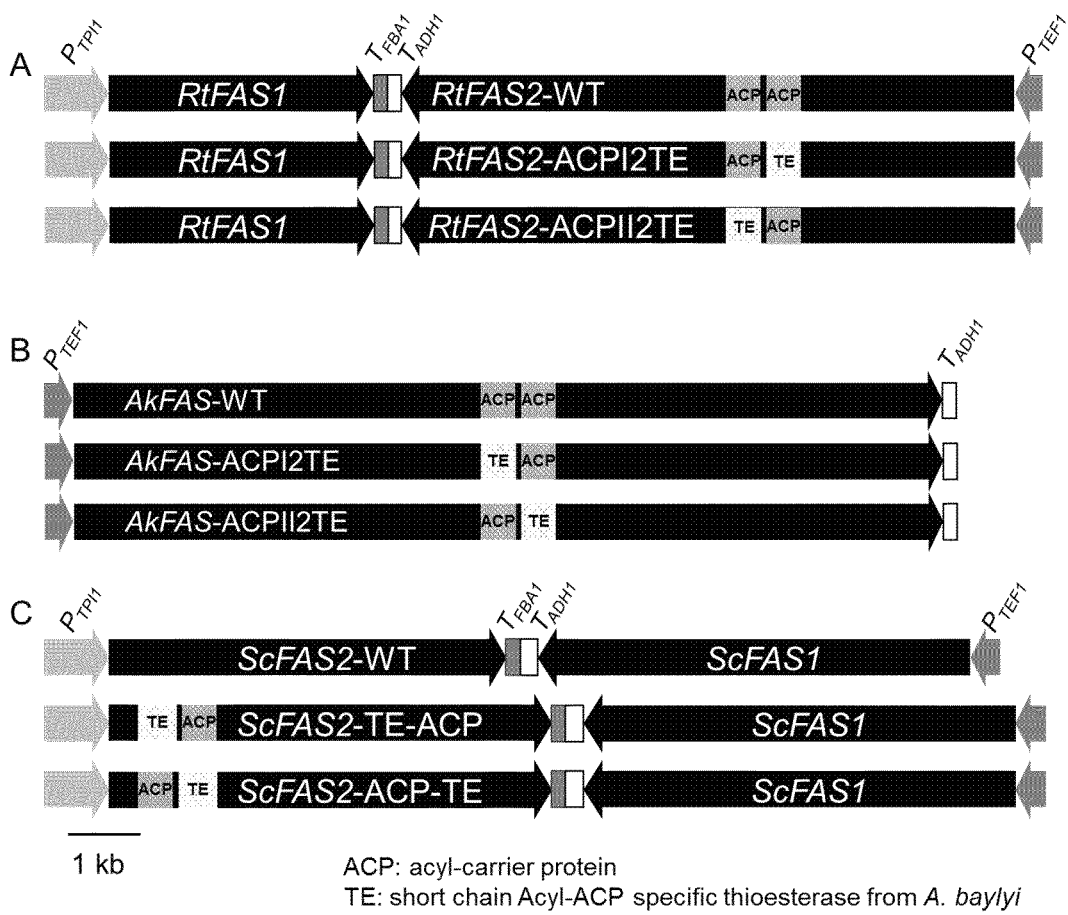
FIG. 2. Expression cassettes of the FAS from *Rhodosporidium toruloides* (A) and *Aplanochytrium kerguelense* (B) and *Saccharomyces cerevisiae* (C). In RtFAS2-ACPI2TE, RtFAS2-ACPII2TE AkFAS2-ACPI2TE and AkFAS2-ACPII2TE, either ACP domain was replaced with a short chain acyl-ACP thioesterase from *Acinetobacter baylyi*. In ScFAS2-TE-ACP and ScFAS2-ACP-TE, the short chain acyl-ACP thioesterase from *A. baylyi* was inserted into the ScFAS2 upstream of downstream of the ACP domain.

The present invention will be described with respect to particular embodiments but the invention is not limited thereto.

Preferred statements (features) and embodiments of the compositions, methods, and uses of this invention are set herein below. Each statements and embodiments of the invention so defined may be combined with any other statement and/or embodiments unless clearly indicated to the contrary. In particular, any feature indicated as being preferred or advantageous may be combined with any other feature or features or statements indicated as being preferred or advantageous. Hereto, the present invention is in particular captured by any one or any combination of one or more of the below numbered aspects and embodiments 1 to 68, with any other statement and/or embodiments.

Numbered statements as disclosed in the present application are:

1. A recombinant polynucleic acid encoding (i) a fatty acid synthase (FAS) or FAS subunit; and (ii) a thioesterase (TE), preferably a heterologous TE, preferably a recombinant polynucleic acid comprising (i) a fatty acid synthase (FAS) encoding sequence or FAS subunit encoding sequence, or a partial fatty acid synthase (FAS) encoding sequence, originating from or derived from a naturally occurring FAS (subunit) gene devoid of thioesterase (TE) encoding nucleotide sequences, wherein a heterologous thioesterase domain (TE) encoding nucleotide sequences is added to said FAS (subunit), preferably before of after an acyl carrier protein domain (ACP) encoding nucleotide sequence of said FAS (subunit), optionally wherein said FAS subunit is FAS 1 or FAS2 or 1. A recombinant prokaryotic or eukaryotic cell comprising, expressing or capable of expressing, or a recombinant polynucleic acid encoding (i) a fatty acid synthase (FAS) or FAS subunit; and (ii) a thioesterase (TE), preferably a heterologous TE, preferably a recombinant prokaryotic or eukaryotic cell comprising, expressing or capable of expressing, or a recombinant polynucleic acid comprising (i) a fatty acid synthase (FAS) encoding sequence or FAS subunit encoding sequence, or a partial fatty acid synthase (FAS) encoding sequence, originating from or derived from a naturally occurring FAS (subunit) gene devoid of thioesterase (TE) encoding nucleotide sequences, wherein a heterologous thioesterase domain (TE) encoding nucleotide sequences is added to said FAS (subunit), preferably before of after an acyl carrier protein domain (ACP) encoding nucleotide sequence of said FAS (subunit), optionally wherein said FAS subunit is FAS 1 or FAS2.

2. The cell or polynucleic acid according to statement 1, wherein said FAS (subunit) and said TE are encoded as a single open reading frame (ORF).

3. The cell or polynucleic acid according to statement 1 or 2, wherein the polynucleic acid sequence encoding said TE is adjacent (directly 5' or 3') relative to the polynucleic acid sequence encoding an acyl carrier protein (ACP) of said FAS (subunit).

4. The cell or polynucleic acid according to any of statements 1 to 3, comprising a fatty acid synthase (FAS) encoding sequence or FAS subunit encoding sequences, or a partial fatty acid synthase (FAS) encoding sequence, originating from or derived from a FAS (subunit) gene, such as a naturally occurring FAS (subunit) gene, having at least two acyl carrier protein (ACP) encoding nucleotide sequences, wherein one of said ACP encoding nucleotide sequences is replaced by a thioesterase (TE) encoding nucleotide sequence.

5. The cell or polynucleic acid according to any of statements 1 to 4, wherein said naturally occurring FAS (subunit) gene is a type I FAS (subunit).

6. The cell or polynucleic acid according to any of statements 1 to 5, wherein said FAS (subunit) is a fungal, in particular yeast, protist, myxomycete, or algae, in particular microalgae, FAS (subunit).

7. The cell or polynucleic acid according to any of statements 1 to 6, wherein said FAS (subunit) is from *Saccharomyces* spp., preferably *S. cerevisiae, Rhodosporidium* spp., preferably *R. toruloides* or *Aplanochytrium* spp., preferably *A. kerguelense*.

8. The cell or polynucleic acid according to any of statements 1 to 7, wherein said TE is an acyl-CoA/ACP TE, preferably a short chain or medium chain acyl-CoA/ACP TE.

9. A recombinant polypeptide encoded by the recombinant polynucleic acid according to any of statements 1 to 8.

10. A recombinant vector comprising the recombinant polynucleic acid according to any of statements 1 to 8 or a polynucleic acid encoding the recombinant polypeptide according to statement 9.

11. The recombinant vector according to statement 10, wherein said vector is an expression vector or a recombination vector.

12. A recombinant prokaryotic or eukaryotic cell comprising the recombinant polynucleic acid according to any of statements 1 to 8, the polypeptide according to statement 9, a polynucleic acid encoding to polypeptide according to statement 6, or the vector according to statement 10 or 11.

13. The recombinant prokaryotic or eukaryotic cell according to statement 12, wherein said recombinant polynucleic acid is genomically integrated.

14. A recombinant prokaryotic or eukaryotic cell comprising a FAS (subunit) protein sequence or a FAS (subunit) protein encoding sequence originating from a FAS (subunit) gene, such as a naturally occurring FAS (subunit) gene, and a TE protein sequence or a TE protein encoding sequence, wherein optionally said FAS (subunit) has at least two ACP polypeptides or ACP polypeptide encoding nucleotide sequences, wherein one of said ACP polypeptides or ACP polypeptide encoding nucleotide sequences is replaced by a TE polypeptide or TE polypeptide encoding nucleotide sequence.

15. The recombinant prokaryotic or eukaryotic cell according to any of statements 1 to 14, wherein said TE or TE encoding nucleotide sequence is a heterologous TE encoding nucleotide sequence, compared to the naturally occurring FAS (subunit).

16. The recombinant prokaryotic or eukaryotic cell according to any of statements 1 to 15, which is a bacterial cell, a fungal cell, or an algae cell.

17. The recombinant prokaryotic or eukaryotic cell according to any of statements 1 to 16, which is a *Saccharomyces* cell, such as a *Saccharomyces cerevisiae* cell.

18. Method for producing a recombinant prokaryotic or eukaryotic cell comprising the step of introducing in a prokaryotic or eukaryotic cell the recombinant polynucleic acid, polypeptide, or vector according to any of statements 1 to 11 or 27-56, or introducing in a prokaryotic or eukaryotic cell a FAS, optionally FAS1 and/or FAS2, and a TE or a polynucleic acid encoding a FAS, optionally FAS1 and/or FAS2, and a TE.

19. Method for producing a recombinant prokaryotic or eukaryotic cell, comprising the steps of
(i) providing a prokaryotic or eukaryotic cell comprising a fatty acid synthase (FAS) gene or FAS subunit gene, optionally a FAS1 and/or FAS2, optionally said FAS (subunit) having at least two acyl carrier protein (ACP) encoding nucleotide sequences, such as comprising two adjacent ACP encoding nucleotide sequences, said FAS (subunit) preferably being devoid of a TE encoding nucleotide sequence; and
(ii) introducing a TE or TE encoding sequence, optionally replacing one of said ACP encoding nucleotide sequences with a TE encoding sequence, wherein said TE encoding nucleotide sequence is preferably introduced, preferably directly, 5' or 3' of an ACP encoding nucleotide sequence of said FAS (subunit).

20. Use of the recombinant polynucleic acid, polypeptide, vector, or cell according to any of statements 1 to 17 or 27-67 in the production of fatty acids, hydrocarbons, fatty aldehydes or fatty alcohols.

21. Method for producing fatty acids, comprising the steps of (i) providing the recombinant prokaryotic or eukaryotic cell according to any of statements 1 to 17 or 60 to 67; and
(ii) culturing said recombinant prokaryotic or eukaryotic cell under suitable culture conditions.

22. The method according to statement 21, further comprising the step of
(iii) isolating and/or purifying said fatty acids.

23. Method for producing (medium or short chain) hydrocarbons, comprising performing the method for producing fatty acids according to statement 21 or 22, further comprising reduction, hydrogenation, decarboxylation or decarbonylation of said fatty acids.

24. Method for producing (medium or short chain) fatty alcohols or fatty aldehydes, comprising performing the method for producing fatty acids according to statement 21 or 22, further comprising hydrogenating said fatty acids, optionally subsequent to esterification of said fatty acids; or further comprising reducing said fatty acids.

25. Use according to statement 20 or method according to statement 21 to 23, wherein said fatty acids are short chain fatty acids (SOFA) or medium chain fatty acids (MCFA).

26. Use according to statement 20 or method according to any of statements 21 to 23, wherein said fatty acids are C1-012 fatty acids, such as C6-C12 fatty acids.

27. The recombinant prokaryotic or eukaryotic cell or recombinant polynucleic acid according to any of statements 1 to 17 or 49 to 56, wherein said FAS is encoded by one or alternatively two discrete and/or separate gene sequences.

28. The recombinant prokaryotic or eukaryotic cell or recombinant polynucleic acid according to any of statements 1 to 17 or 27 or 49 to 56, wherein said FAS is or comprises FAS1 and/or FAS2.

29. The recombinant prokaryotic or eukaryotic cell or recombinant polynucleic acid according to any of statements 1 to 8 or 27 to 28 or 49 to 56, wherein said FAS is or comprises a FAS subunit α and/or a FAS subunit β.

30. The recombinant prokaryotic or eukaryotic cell or recombinant polynucleic acid according to any of statements 1 to 8 or 27 to 28 or 49 to 56, wherein said FAS (subunit) originates from an organism listed in Table 1, preferably *Saccharomyces* sp. (e.g. *S. cerevisiae*), *Rhodosporidium* sp. (e.g. *R. toruloides*) or *Aplanochytrium* sp. (e.g. *A. kerguelense*).

31. The recombinant prokaryotic or eukaryotic cell or recombinant polynucleic acid according to any of statements 1 to 8 or 27 to 28 or 49 to 56, wherein said FAS (subunit) comprises or consists of a sequence as set forth in SEQ ID NO: 1 to 4 or 19, a fragment thereof, or a sequence having at least 50%, preferably at least 60%, more preferably at least 70%, most preferably at least 80% sequence identity with SEQ ID NO: 1 to 4 or 19, or a fragment thereof and/or an orthologue thereof.

32. The recombinant prokaryotic or eukaryotic cell or recombinant polynucleic acid according to statement 31, wherein said fragment comprises an ACP encoding sequence.

33. The recombinant prokaryotic or eukaryotic cell or recombinant polynucleic acid according to statement 31, wherein said sequence having at least 50%, preferably at least 60%, more preferably at least 70%, most preferably at least 80% sequence identity with SEQ ID NO: 1 to 4, or 19 is an orthologue or functional variant of said FAS (subunit) comprising or consisting of a sequence as set forth in SEQ ID NO: 1 to 4, or 19.

34. The recombinant prokaryotic or eukaryotic cell or recombinant polynucleic acid according to any of statements 1 to 8 or 27 to 30 or 49 to 56, comprising a polynucleic acid sequence comprising or consisting of a sequence as set forth in SEQ ID NO: 5, 6, 15, or 16, a fragment thereof, or a sequence having at least 50%, preferably at least 60%, more preferably at least 70%, most preferably at least 80% sequence identity with SEQ ID NO: 5, 6, 15, or 16, or a fragment thereof and/or an orthologue thereof.

35. The recombinant prokaryotic or eukaryotic cell or recombinant polynucleic acid according to statement 34, wherein said fragment comprises an ACP encoding nucleotide sequence and a TE encoding nucleotide sequence, preferably from 5' to 3' an ACP encoding nucleotide sequence and a TE encoding nucleotide sequence, or from 5' to 3' a TE encoding nucleotide sequence and an ACP encoding nucleotide sequence, preferably without intervening (enzyme) coding nucleotide sequences.

36. The recombinant prokaryotic or eukaryotic cell or recombinant polynucleic acid according to statement 34, wherein said sequence having at least 50%, preferably at least 60%, more preferably at least 70%, most preferably at least 80% sequence identity with SEQ ID NO: 5, 6, 15, or 16 or is an orthologue or functional variant of said FAS comprising or consisting of a sequence as set forth in SEQ ID NO: 5, 6, 15, or 16.

37. The recombinant prokaryotic or eukaryotic cell or recombinant polynucleic acid according to any of statements 1 to 8 or 27 to 36 or 43 to 56, wherein said FAS (subunit) comprises or consists of one or more, preferably all of the following domains, preferably from N- to C-terminus: acetyltransferase (AT), enoyl reductase (ER), dehydratase (DH), malonyl/palmitoyl transferase (MPT), acyl carrier protein (ACP), ketoacyl synthase (KS), ketoacyl reductase (KR), phosphopantetheinyl transferase (PPT).

38. The recombinant prokaryotic or eukaryotic cell or recombinant polynucleic acid according to any of statements 1 to 8 or 27 to 37 or 43 to 56, comprising a polynucleic acid sequence wherein said polynucleic acid comprises or consists of a sequence, preferably from 5' to 3' encoding one or more, preferably all of the following domains: acetyl-transferase (AT), enoyl reductase (ER), dehydratase (DH), malonyl-palmitoyl transferase (MPT), acyl carrier protein (ACP), ketoacyl synthase (KS), ketoacyl reductase (KR), phosphopantetheinyl transferase (PPT).

39. The recombinant prokaryotic or eukaryotic cell or recombinant polynucleic acid according to any of statements 1 to 8, or 24 to 38 or 43 to 56, wherein said TE originates from an organism listed in Table 2, preferably TE from *Acinetobacter* sp. (e.g. *A. baylyi* or *A. baumannii*).

40. The recombinant prokaryotic or eukaryotic cell or recombinant polynucleic acid according to any of statements 1 to 8, or 27 to 39 or 43 to 56, wherein said TE comprises or consists of a sequence as set forth in SEQ ID NO: 7 or a sequence having at least 50%, preferably at least 60%, more preferably at least 70%, most preferably at least 80% sequence identity with SEQ ID NO: 7.

41. The recombinant prokaryotic or eukaryotic cell or recombinant polynucleic acid according to statement 40, wherein said sequence having at least 50%, preferably at least 60%, more preferably at least 70%, most preferably at least 80% sequence identity with SEQ ID NO: 7 is an orthologue or functional variant of said TE comprising or consisting of a sequence as set forth in SEQ ID NO: 7.

42. The recombinant prokaryotic or eukaryotic cell or recombinant polynucleic acid according to any of statements 1 to 8, or 27 to 41 or 43 to 56, wherein said nucleotide sequence encoding said ACP is not the most 3' or 5' nucleotide sequence.

43. The recombinant prokaryotic or eukaryotic cell or recombinant polynucleic acid according to statement 42, wherein said ACP encoding sequence is the ACP encoding sequence which is replaced by said TE encoding sequence.

44. The recombinant prokaryotic or eukaryotic cell or recombinant polynucleic acid according to any of statements 4 to 8, or 27 to 43 or 43 to 56, wherein said two ACP encoding sequences are arranged in tandem.

45. The recombinant prokaryotic or eukaryotic cell or recombinant polynucleic acid according to any of statements 1 to 8, or 27 to 44 or 43 to 56, wherein said FAS (subunit) gene(s) encode(s) one or more, preferably all of the following domains: acetyl-transferase (AT), enoyl reductase (ER), dehydratase (DH), malonyl-palmitoyl transferase (MPT), acyl carrier protein (ACP), ketoacyl synthase (KS), ketoacyl reductase (KR), phosphopantetheinyl transferase (PPT).

46. The recombinant prokaryotic or eukaryotic cell or recombinant polynucleic acid according to any of statements 1 to 8, or 27 to 44 or 43 to 56, wherein said naturally occurring FAS (subunit) originates from an oleaginous cell, preferably an oleaginous yeast or oleaginous microalgae.

47. A recombinant prokaryotic or eukaryotic cell or recombinant polynucleic acid encoding from 5' to 3' respectively MPT, ACP, TE, and KS, wherein said TE is preferably heterologous compared to said MPT, ACP, and/or KS.

48. A recombinant prokaryotic or eukaryotic cell or recombinant polynucleic acid encoding from 5' to 3' respectively MPT, TE, ACP, and KS, wherein said TE is preferably heterologous compared to said MPT, ACP, and/or KS.

49. A recombinant prokaryotic or eukaryotic cell or recombinant polynucleic acid comprising or encoding from 5' to 3' respectively:
   AT, ER, DH, MPT, ACP, TE, KS, KR, and PPT;
   AT, ER, DH, MPT, TE, ACP, KS, KR, and PPT;
   AT, ER, DH, MPT, ACP, TE, KS, and KR;
   AT, ER, DH, MPT, TE, ACP, KS, and KR;
   AT, ER, DH, MPT, ACP, TE, and KS;
   AT, ER, DH, MPT, TE, ACP, and KS;
   AT, ER, DH, MPT, ACP, and TE;
   AT, ER, DH, MPT, TE, and ACP;
   ER, DH, MPT, ACP, TE, KS, KR, and PPT;
   ER, DH, MPT, TE, ACP, KS, KR, and PPT;
   DH, MPT, ACP, TE, KS, KR, and PPT;
   DH, MPT, TE, ACP, KS, KR, and PPT;
   MPT, ACP, TE, KS, KR, and PPT;
   MPT, TE, ACP, KS, KR, and PPT;
   ACP, TE, KS, KR, and PPT;
   TE, ACP, KS, KR, and PPT;
   TE and ACP;
   ACP and TE;
   MPT, ACP, TE, and KS; or
   MPT, TE, ACP, and KS,
wherein said TE is preferably heterologous compared to said AT, ER, DH, MPT, ACP, KS, KR, and/or PPT.

50. A recombinant prokaryotic or eukaryotic cell or recombinant polynucleic acid comprising the polynucleic acid according to any of statements 47 to 49.

51. The recombinant prokaryotic or eukaryotic cell or polynucleic acid according to any of statements 47 to 50, encoding from 5' to 3' respectively AT, ER, DH, MPT, TE, ACP, KS, KR, and PPT.

52. The recombinant prokaryotic or eukaryotic cell or polynucleic acid according to any of statements 47 to 51, encoding from 5' to 3' respectively DH, MPT, TE, ACP, KS, KR, and PPT.

53. The recombinant prokaryotic or eukaryotic cell or polynucleic acid according to any of statements 47 to 52, wherein said respectively AT, ER, DH, MPT, ACP, KS, KR, and PPT are derived from a naturally occurring FAS (subunit) gene, preferably a type I FAS (subunit) gene.

54. The recombinant prokaryotic or eukaryotic cell or polynucleic acid according to statement 53, wherein said FAS (subunit) gene is a fungal, in particular yeast, protist, myxomycete, or algae, in particular microalgae, FAS (subunit) gene.

55. The recombinant prokaryotic or eukaryotic cell or polynucleic acid according to any of statements 53 to 54, wherein said naturally occurring FAS (subunit) gene is from *Rhodosporidium* spp., preferably *R. toruloides* or *Aplanochytrium* spp., preferably *A. kerguelense*.

56. The recombinant prokaryotic or eukaryotic cell or polynucleic acid according to any of statements 47 to 55, wherein said TE is an acyl-CoA/ACP TE, preferably a short chain or medium chain acyl-CoA/ACP TE.

57. A recombinant polypeptide encoded by the recombinant polynucleic acid according to any of statements 47 to 56.

58. A recombinant vector comprising the recombinant polynucleic acid according to any of statements 47 to 56 or a polynucleic acid encoding the recombinant polypeptide according to statement 57.

59. The recombinant vector according to statement 58, wherein said vector is an expression vector or a recombination vector.

60. A recombinant prokaryotic or eukaryotic cell comprising the recombinant polynucleic acid according to any of statements 47 to 56, the polypeptide according to statement 57, a polynucleic acid encoding to polypeptide according to statement 57, or the vector according to statement 58 or 59.

61. The recombinant prokaryotic or eukaryotic cell according to any of the previous statements, wherein a polynucleic acid encoding said FAS, FAS1, or FAS2 and/or said TE is genomically integrated.

62. The recombinant prokaryotic or eukaryotic cell according to any of the previous statements, wherein said TE encoding nucleotide sequence is a heterologous TE encoding nucleotide sequence.

63. The recombinant prokaryotic or eukaryotic cell according to any of the previous statements, which is a bacterial cell, a fungal cell, or an algae cell.

64. The recombinant prokaryotic or eukaryotic cell according to any of the previous statements, which is a *Rhodosporidium toruloides* or *Aplanochytrium kerguelense* cell.

65. The recombinant prokaryotic or eukaryotic cell according to any of the previous statements, comprising one or more polynucleic acid encoding AT, ER, DH, MPT, TE, ACP, KS, KR, and PPT.

66. The recombinant prokaryotic or eukaryotic cell according to any of the previous statements which is an oleaginous cell, preferably an oleaginous yeast or oleaginous microalgae cell.

67. The recombinant prokaryotic or eukaryotic cell according to any of the previous statements which is a single cell organism.

68. The recombinant polynucleic acid according to any of the preceding statements, wherein one or more of AT, ER, DH, MPT, KS, KR, and PPT are modified in said FAS (subunit).

Before the present methods of the invention are described, it is to be understood that this invention is not limited to particular methods, components, products or combinations described, as such methods, components, products and combinations may, of course, vary. It is also to be understood that the terminology used herein is not intended to be limiting, since the scope of the present invention will be limited only by the appended claims.

Preferred statements (features) and embodiments of this invention are set herein below. Each statements and embodiments of the invention so defined may be combined with any other statement and/or embodiments unless clearly indicated to the contrary. In particular, any feature indicated as being preferred or advantageous may be combined with any other feature or features or statements indicated as being preferred or advantageous. Hereto, the present invention is in particular captured by any one or any combination of one or more of the above numbered aspects and embodiments 1 to 68, with any other statement and/or embodiments. The present invention will be described with respect to particular embodiments but the invention is not limited thereto but only by the claims. Any reference signs in the claims shall not be construed as limiting the scope.

Where the term "comprising" is used in the present description and claims, it does not exclude other elements or steps. The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of", as well as the terms "consisting essentially of", "consists essentially" and "consists essentially of".

As used herein, the singular forms "a", "an", and "the" include both singular and plural referents unless the context clearly dictates otherwise.

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−20% or less, preferably +/−10% or less, more preferably +/−5% or less, and still more preferably +/−1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the following detailed description of the invention, reference is made to the accompanying drawings that form a part hereof, and in which are shown by way of illustration only of specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, $2^{nd}$ ed., Cold Spring Harbor Press, Plainsview, N.Y. (1989); and Ausubel et al., Current Protocols in Molecular Biology (Supplement 47), John Wiley & Sons, New York (1999), Innis et al., PCR Protocols: A Guide to Methods and Applications, Academic Press: San Diego, 1990. General principles of microbiology are set forth, for example, in Davis, B. D. et al., Microbiology, 3rd edition, Harper & Row, publishers, Philadelphia, Pa. (1980), for definitions and terms of the art. The definitions provided herein should not be construed to have a scope less than understood by a person of ordinary skill in the art.

Unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein.

The inventors have found that surprisingly, despite its complex structure, fatty acid synthase enzyme complexes of micro-organisms can be modified to generate small to medium chain fatty acids.

In an aspect, the invention relates to a recombinant polynucleic acid comprising a fatty acid synthase (FAS) encoding sequence, or a partial fatty acid synthase (FAS) encoding sequence (i.e. a FAS subunit encoding sequence), and a thioesterase (TE) encoding sequence; optionally wherein said FAS (subunit) originates from or is derived from a naturally occurring FAS (subunit) gene having at least two or exactly two acyl carrier protein (ACP) encoding nucleotide sequences, wherein one of said ACP encoding nucleotide sequences is inactivated, disrupted and/or replaced by a thioesterase (TE) encoding nucleotide sequence. In related aspects, the invention relates to a polypeptide encoded by said polynucleic acid, a vector comprising said polynucleic acid, or a vector comprising a polynucleic acid encoding said polypeptide, and a host cell comprising said polynucleic acid, said polypeptide, or said vector.

In an aspect, the invention relates to a recombinant polynucleic acid comprising a fatty acid synthase (FAS) encoding sequence, or a partial fatty acid synthase (FAS) encoding sequence (i.e. a FAS subunit encoding sequence), originating from or derived from a naturally occurring FAS (subunit) gene having an acyl carrier protein (ACP) encoding nucleotide sequence and devoid of thioesterase domain (TE) encoding nucleotide sequence, wherein a heterologous thioesterase domain (TE) encoding nucleotide sequences is added before of after the acyl carrier protein (ACP) encoding nucleotide sequence. In related aspects, the invention relates to a polypeptide encoded by said polynucleic acid, a vector comprising said polynucleic acid, or a vector comprising a polynucleic acid encoding said polypeptide, and a host cell comprising said polynucleic acid, said polypeptide, or said vector.

The application provides the expression of said recombinant polynucleic acids in a host cell. Accordingly, in a related aspect, the invention relates to a recombinant host cell comprising, expressing, or capable of expressing said polynucleic acid comprising a fatty acid synthase (FAS) encoding sequence, or a partial fatty acid synthase (FAS) encoding sequence (i.e. a FAS subunit encoding sequence), and a thioesterase (TE) encoding sequence; optionally wherein said FAS (subunit) originates from or is derived from a naturally occurring FAS (subunit) gene having at least two or exactly two acyl carrier protein (ACP) encoding nucleotide sequences, wherein one of said ACP encoding nucleotide sequences is inactivated, disrupted and/or replaced by a thioesterase (TE) encoding nucleotide sequence. In related aspects, the invention relates to a polypeptide encoded by said polynucleic acid, a vector comprising said polynucleic acid, or a vector comprising a polynucleic acid encoding said polypeptide, and a host cell comprising said polynucleic acid, said polypeptide, or said vector.

Similarly, the invention relates to a recombinant host cell comprising, expressing, or capable of expressing said polynucleic acid comprising a fatty acid synthase (FAS) encoding sequence, or a partial fatty acid synthase (FAS) encoding sequence (i.e. a FAS subunit encoding sequence), originating from or derived from a naturally occurring FAS (subunit) gene having an acyl carrier protein (ACP) encoding nucleotide sequence and devoid of thioesterase domain (TE) encoding nucleotide sequence, wherein a heterologous thioesterase domain (TE) encoding nucleotide sequences is added before of after the acyl carrier protein (ACP) encoding nucleotide sequence. In related aspects, the invention relates to a polypeptide encoded by said polynucleic acid, a vector comprising said polynucleic acid, or a vector comprising a polynucleic acid encoding said polypeptide, and a host cell comprising said polynucleic acid, said polypeptide, or said vector.

It will be understood that, in the recombinant polynucleic acid and the recombinant host cell according to the invention as described herein when referring to a FAS, a functional FAS is intended, which can comprise FAS1, FAS2 or both FAS1 and FAS2 subunits. Accordingly, all individual enzymatic domains necessary for reconstituting a functional FAS are present in said recombinant polynucleic acid (and expressed or capable of being expressed in said cell). For instance, the recombinant polynucleic acid may comprise and the host cell may comprise or express an engineered FAS subunit comprising a TE (such as a FAS1 or FAS2 additionally comprising a TE) and a native or naturally occurring or non-engineered FAS subunit (such as FAS2 or FAS1) to complement the engineered FAS subunit and to reconstitute a functional FAS.

In certain embodiments, the recombinant host cell according to the invention as described herein comprises, expresses or is capable of expressing a functional native or naturally occurring (optionally heterologous) FAS, optionally comprising FAS1 and FAS2 subunits. In such embodiments, the (heterologous) TE encoding sequence is integrated in the FAS encoding sequence, as described herein elsewhere or is provided separately. Accordingly, the FAS may be an engineered native or naturally occurring (heterologous) FAS additionally comprising a TE or alternatively may be a native or naturally occurring (heterologous) FAS complemented with a TE.

As used herein, the terms "nucleic acid molecule", "polynucleotide", "polynucleic acid", "nucleic acid" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

The term "recombinant" as used herein essentially refers to a (poly)nucleic acid, (poly)peptide, cell, or organism which is not naturally occurring or artificial, i.e. man-made. This term refers to an engineered or genetically manipulated (poly)nucleic acid, (poly)peptide, cell, or organism. In contrast, the term "naturally occurring" as used herein refers to a (poly)nucleic acid, (poly)peptide, cell, or organism which is not manipulated and can be found in nature. As used herein, the term "originating from a naturally occurring FAS (subunit)" refers to a polynucleic acid or polypeptide derived from a naturally occurring FAS (subunit) polynucleic acid or polypeptide, which has been artificially modified (i.e. recombinant polynucleic acid or polypeptide). It will be understood that the FAS (subunit) gene, polynucleic acid or protein as referred to herein is modified at least by introducing a TE, whether or not by replacing an ACP in instances where multiple ACPs are originally present in said FAS (subunit). However, further modifications of said FAS (subunit) are also possible. By means of example, one or more of the functional domains (e.g. AT, ER, DH, MPT, KS, KR, and/or PPT) of said FAS (subunit) may be modified, including replacement of such functional domain with for instance and without limitation a corresponding functional domain of an orthologous FAS (subunit).

As used herein, the terms "polypeptide", "protein", "peptide", and "amino acid sequence" are used interchangeably, and refer to a polymeric form of amino acids of any length, which can include coded and non-coded amino acids, chemically or biochemically modified or derivatized amino acids, and polypeptides having modified peptide backbones. As used herein, amino acid residues will be indicated either by their full name or according to the standard three-letter or one-letter amino acid code.

The term "gene" as generally used herein refers to a nucleic acid sequence which contains a coding sequence, a promoter and any other regulatory regions required for expression in a host cell.

As used herein, the term "promoter" refers to an untranslated sequence located within 50 bp upstream the transcription start site and which controls the start of transcription of the structural gene. Generally it is located within about 1 to 1000 bp, preferably 1-500 bp, especially 1-100 bp upstream (i.e., 5') to the translation start codon of a structural gene. Similarly, the term "terminator" refers to an untranslated sequence located downstream (i.e., 3') to the translation stop codon of a structural gene (generally within about 1 to 1000 bp, more typically 1-500 base pairs and especially 1-100 base pairs) and which controls the end of transcription of the structural gene. A promoter or terminator is "operatively linked or connected" or "operably linked or connected" to a coding sequence if its position relative to that of the coding sequence is such that the promoter or terminator, as the case may be, performs its transcriptional control function.

As used herein, the term "heterologous" or "exogenous" refers to the fact that the gene, nucleic acid or protein sequence, domain, or coding sequence under consideration originates from outside of the host organism of concern or study, or refers to the fact that the gene or coding sequence under consideration is not native or endogenous to the host but rather originates or has been cloned from a different cell type or from an organism of a different species than the recipient host.

The term "native" or "endogenous" is used herein with respect to genetic materials (e.g., a gene, promoter or terminator, etc.) that are found (apart from individual-to-individual mutations which do not affect function) within the genome of wild-type cells of the host strain.

The term "overexpression" as used herein when referring to expression of a gene in a host cell, refers to the fact that it is expressed at a higher level than naturally in said host cell. This may imply that it is a foreign gene, not naturally expressed in the host cell or that the endogenous gene has been modified so as to increase expression in said host cell.

The term "inactivation" as used herein when referring to a gene, gene sequence, or sequence encoding a domain present in a host cell, refers to the fact that the gene product is either not expressed or not active in said host cell. This typically implies that the endogenous gene, gene sequence, or sequence encoding a domain has been modified so as to no longer allow expression in said host cell but may also imply that the gene has been modified to ensure that the gene product is no longer active, and includes partial or complete, preferably complete deletion of the gene, gene sequence, or sequence encoding a domain.

By "encoding" is meant that a nucleic acid sequence or part(s) thereof corresponds, by virtue of the genetic code of an organism in question, to a particular amino acid sequence, e.g., the amino acid sequence of a desired polypeptide or protein. By means of example, nucleic acids "encoding" a particular polypeptide or protein may encompass genomic, hnRNA, pre-mRNA, mRNA, cDNA, recombinant or synthetic nucleic acids.

Preferably, a nucleic acid encoding a particular polypeptide or protein may comprise an open reading frame (ORF) encoding said polypeptide or protein. An "open reading frame" or "ORF" refers to a succession of coding nucleotide triplets (codons) starting with a translation initiation codon and closing with a translation termination codon known per se, and not containing any internal in-frame translation termination codon, and potentially capable of encoding a polypeptide. Hence, the term may be synonymous with "coding sequence" as used in the art. In certain embodiment, the polynucleic acid sequences as described herein comprise an open reading frame comprising an ACP encoding sequence and a TE encoding sequence, preferably adjacent to each other.

The term "fatty acid" as used herein refers to any of a large group of organic acids, especially those found in animal and vegetable fats and oils. Characteristically made up of saturated or unsaturated aliphatic compounds with an even number of carbon atoms, this group of acids includes palmitic, stearic, and oleic acids, but also includes short chain fatty acids (SOFA) and medium chain fatty acids (MCFA). Short-chain fatty acids (SOFA) are fatty acids with aliphatic tails of fewer than six carbons (e.g. butyric acid), while medium-chain fatty acids (MCFA) are fatty acids with aliphatic tails of typically 6-12 carbons.

The term "saturated fatty acid" as used herein refers to any fatty acid in which all bonds between carbon atoms are all single bonds.

The term "unsaturated fatty acid" as used herein refers to any fatty acid in which at least one of the bonds between carbon atoms is a double bond.

The term "fatty acid synthase", "fatty acid synthetase", or "FAS" refers to the enzyme complex or multi-enzyme protein that catalyzes fatty acid synthesis. FAS is not a single enzyme but a multimodular enzymatic system composed of different enzymatic or structural units or domains. There are two principal classes of FAS. Type I FAS utilise a single or alternatively two large, multifunctional polypeptide(s) and are common to both mammals and fungi (although the structural arrangement of fungal and mammalian synthases differ). A Type I fatty acid synthase system is also found in the CMN group of bacteria (corynebacteria, mycobacteria, and nocardia). Type II FAS is found in archaea and bacteria, and is characterized by the use of discrete, monofunctional enzymes for fatty acid synthesis. The mechanism of Type I FAS and Type II FAS elongation and reduction is the same, as the domains of the Type II FAS enzymes are largely homologous to their domain counterparts in Type I FAS multienzyme polypeptides. FAS genes typically encode multiple enzymatic units or domains, such as acetyl-transferase (AT), enoyl reductase (ER), dehydratase (DH), malonyl-palmitoyl transferase (MPT), acyl carrier protein (ACP), ketoacyl synthase (KS), ketoacyl reductase (KR), phosphopantetheinyl transferase (PPT), thioesterase (TE), malonyl-acetyl transferase (MAT), some or all of which typically constitute the functional FAS complex. By means of example, and without limitation, fungal FAS typically comprises the following enzymatic domains: acetyl-transferase (AT), enoyl reductase (ER), dehydratase (DH), malonyl-palmitoyl transferase (MPT), acyl carrier protein (ACP), ketoacyl synthase (KS), ketoacyl reductase (KR), phosphopantetheinyl transferase (PPT). Animal, in particular mammalian, FAS typically comprises the following enzymatic domains: ketoacyl synthase (KS), malonyl-acetyl transferase (MAT), dehydratase (DH), enoyl reductase (ER), ketoacyl reductase (KR), acyl carrier protein (ACP), thioesterase (TE). Type I FAS is encoded by one or alternatively two discrete genes or gene sequences. In case FAS is encoded by two genes or gene sequences, the individual gene (sequences) encode FAS1 (also called FAS subunit β, or FAS β-chain) and FAS2 (also called FAS subunit α, FAS α-chain). Which enzymatic domain is comprised in which subunit or chain is variable. By means of example, and without limitation, *Saccharomyces cerevisiae* FAS comprises (arranged from N- to C-terminus) ACP, KS, KR, and PPT on FAS2 (α-chain) and comprises (arranged from N- to C-terminus) AT, ER, DH, and MPT on FAS 1 (β-chain). *Cryptococcus neoformans* FAS comprises (arranged from N- to C-terminus) KS, KR, and PPT on FAS2 (α-chain) and comprises (arranged from N- to C-terminus) AT, ER, DH, MPT, and ACP on FAS 1 (β-chain). *Rhodosporidium toruloides* FAS comprises (arranged from N- to C-terminus) DH, MPT, ACP, KS, KR, and PPT on FAS2 (α-chain) and comprises (arranged from N- to C-terminus) AT and ER on FAS 1 (β-chain). It is noted that *Rhodosporidium toruloides* comprises two ACP domains arranged in tandem. In contrast to the above, other organisms encode FAS as a single gene, and thus FAS is a single polypeptide. By means of example, and without limitation, *Ustilago maydis* and *Aplanochytrium kerguelense* FAS comprise on a single polypeptide (arranged from N- to C-terminus) acetyl-transferase (AT), enoyl reductase (ER), dehydratase (DH), malonyl-palmitoyl transferase (MPT), acyl carrier protein (ACP), ketoacyl synthase (KS), ketoacyl reductase (KR), phosphopantetheinyl transferase (PPT). It is noted that *Aplanochytrium kerguelense* comprises two ACP domains arranged in tandem. As will be appreciated by the skilled person, "tandem" arrangement of ACP refers to two (or more) ACP domains which are located next to each other (i.e. adjacent, as defined herein elsewhere, optionally connected through a linker) in the protein, without intervening other FAS domains, i.e. without intervening AT, ER, DH, MPT, KS, KR, MAT, TE or PPT. As used herein, the term "fatty acid synthase subunit", "fatty acid synthetase subunit", or "FAS subunit" refers to a partial FAS in which not all domains of a fully functional FAS are present. By means of example, a FAS subunit may lack one or more of acetyl-transferase (AT), enoyl reductase (ER), dehydratase (DH), malonyl-palmitoyl transferase (MPT), acyl carrier protein (ACP), ketoacyl synthase (KS), ketoacyl reductase (KR), phosphopantetheinyl transferase (PPT), malonyl-acetyl transferase (MAT). By means of further example, It will be understood that a FAS subunit, while one or more of the enzymatic domains are lacking, the domains which are present are preferably complete and functional, i.e. these domains are preferably not truncated. By means of further example, a FAS subunit as referred to herein may be FAS1 or FAS2, as described herein elsewhere. Preferably, the FAS subunit as referred to herein comprises at least one ACP domain, such as for instance one ACP or two ACP domains, optionally two ACP domains in tandem. Exemplary FAS subunits can for instance be derived from FIG. 1. It will be understood that a FAS subunit as referred to herein does not contain all enzymatic domains necessary for full functionality. In order to achieve full functionality, the FAS subdomain as referred to herein may need to be complemented with the enzymatic domains which are missing in the FAS subunit. Such missing domains may advantageously be provided as a single polypeptide, or as a single ORF encoding a single polypeptide.

For domain organization of representative Type I FAS of animal and fungal origin, reference is made to Maier et al. (2008) "The crystal structure of a mammalian fatty acid synthase"; Science; 321(5894):1315-22 (doi: 10.1126/science.1161269); and Lomakin et al (2007) "The crystal structure of yeast fatty acid synthase, a cellular machine with eight active sites working together"; Cell; 129(2):319-32, which are hereby incorporated in their entirety by reference.

In a preferred embodiment, FAS as described herein is Type I FAS, including FAS1 and/or FAS2. Accordingly, in certain embodiments, FAS as described herein is or comprises FAS1 or FAS2. Preferably, FAS as described herein is or comprises FAS1 or FAS2, wherein said FAS1 or FAS2 comprises an ACP domain. In certain embodiments, when reference is made to a TE domain inserted in FAS upstream or downstream of an ACP, in the case where FAS is composed of two discrete subunits FAS1 and FAS2, the TE domain is inserted on the FAS subunit containing the ACP. Accordingly, in certain embodiments, FAS as referred to herein may related to FAS1 or FAS2, whichever comprises the ACP.

In certain embodiments, the TE as referred to herein, such as preferably the heterologous TE, is provided or inserted in the FAS (subunit), preferably the ACP containing FAS subunit. In certain embodiments, the TE as referred to herein, such as preferably the heterologous TE, is not provided or inserted in the FAS (subunit), In certain embodiments, the TE as referred to herein, such as preferably the heterologous TE, is provided or inserted in the FAS (subunit) upstream or downstream of an ACP of said FAS (subunit), i.e. adjacent or directly adjacent to an ACP of said FAS (subunit), preferably directly upstream or downstream of an ACP of said FAS (subunit), i.e. a TE nucleic acid sequence directly 5' or 3' of a nucleic acid sequence of the ACP, or a TE polypeptide sequence directly N-terminal or C-terminal of a polypeptide sequence of the ACP. As used in this context, the term "directly" indicates that between the ACP and TE sequences no additional domains are present, in particular no additional enzymatic domains are present (such as AT, ER, DH, MPT, KS, KR, or PPT), in particular no additional functional enzymatic domains are present. The skilled person will understand that possibly linker sequences may be present between the ACP and TE sequences, as is known in the art. Linker sequences may however also be absent. It will be understood that linker sequences are not and do not comprise (functional) enzymatic domains. In certain embodiments, a linker sequence of at most 200 nucleotides is present, such as for instance at most 100 nucleotides. In certain embodiments, a linker sequence of at most 70 amino acids is present, such as at most 35 amino acids. In certain embodiments, a linker sequence is encoded by a nucleic acid sequence of SEQ ID NO: 110, or a functional fragment or variant thereof. In certain embodiments, a linker has an amino acid sequence of SEQ ID NO: 111, or a functional fragment or variant thereof, or a nucleic acid sequence encoding an amino acid sequence of SEQ ID NO: 111.

In a preferred embodiment, FAS (subunit) as described herein is FAS (subunit) originating from a single cell organism, preferably selected from the group comprising or consisting of yeast, protist, myxomycete, and microalgae, preferably yeast or microalgae.

In a preferred embodiment, FAS (subunit) as described herein is FAS (subunit) originating from an oleaginous organism, preferably an oleaginous single cell organism. In a preferred embodiment, FAS as described herein is Type I FAS originating from an oleaginous single cell organism, preferably selected from the group comprising or consisting of yeast, protist, myxomycete, and microalgae, preferably yeast or microalgae.

In certain embodiments, FAS (subunit) may be artificial, in that different enzymatic domains may originate from different organisms. In certain embodiments, different enzymatic domains may originate from the same organism. In certain embodiments, different FAS subunits may originate from different organisms. In certain embodiments, different FAS subunits may originate from the same organism.

In certain embodiments, FAS, preferably Type I FAS, as used herein refers to a single polypeptide comprising ACP and one or more, preferably all, other FAS enzyme domains (or a polynucleic acid encoding the respective domains). In certain other embodiments, FAS as used herein refers to FAS1 and/or FAS2 comprising ACP and one or more, preferably all, other FAS1 and/or FAS2 domains (or a polynucleic acid encoding the respective domains). In certain embodiments the TE and ACP (which may reside in a FAS composed as a single protein or a FAS composed of FAS1 and FAS2 subproteins) as referred to herein are encoded by a single open reading frame. Accordingly, in an aspect, the invention relates to a recombinant polynucleic acid encoding a fungal fatty acid synthase (FAS) subunit (e.g. FAS1 or FAS2), said subunit (e.g. FAS1 or FAS2) comprising an ACP and a thioesterase (TE), preferably a heterologous TE.

The skilled person will understand that if FAS is composed of FAS1 and FAS2, TE may be inserted in one of these, preferably adjacent and ACP contained therein. In the methods for producing fatty acids (or derivatives thereof), as referred to herein elsewhere, in certain embodiments, only the so-engineered FAS1 (or FAS2) may be introduced in a host organism, if such host organism naturally contains FAS (which may or may not be the same organism as where the engineered FAS is derived from). In this way, the host organism may complement the other FAS subunit (e.g. a TE containing FAS1 is introduced in a host organism endogenously expressing FAS2).

As referred to herein, the (naturally occurring) FAS (subunit) as referred to herein may in certain embodiments comprise at least two ACP domains, i.e. the FAS (subunit) gene(s) encode at least two ACP domains. In the recombinant polynucleic acid or polypeptide sequences, vectors, cells, or methods as described herein, one of the two ACP domains or ACP encoding sequences may be replaced by a TE domain or TE encoding sequence. The skilled person will understand that if more than two ACP domains are present in the naturally occurring FAS (subunit), more than one ACP domain may be replaced by a TE domain, as long as at least one ACP domain remains. In certain embodiments, where FAS is composed of different FAS subunits, preferably only one of the subunits (or nucleotide sequence encoding the subunit) comprises an ACP (or multiple ACPs), whereas the other subunit (or nucleotide sequence encoding the subunit) does not comprise an ACP.

As referred to herein, the (naturally occurring) FAS (subunit) as referred to herein preferably comprises at least one ACP domain, i.e. the FAS (subunit) gene(s) encode at least one ACP domain and is devoid of TE domain, i.e. the FAS (subunit) gene(s) does not encode a TE domain. In the recombinant polynucleic acid or polypeptide sequences, vectors, cells, or methods as described herein, a TE domain is preferably added before of after the ACP domain or TE encoding sequence has been added before or after the ACP encoding sequence.

Non-limiting examples of suitable (naturally occurring) FAS for use in the aspects according to the invention as described herein, having at least two ACP domains are listed in Table 1. Accordingly, in certain embodiments, the (naturally occurring) FAS is as specified in Table 1 or derived from an organism as listed in Table 1. By extension, the individual FAS domains (or combinations thereof), such as acetyl-transferase (AT), enoyl reductase (ER), dehydratase (DH), malonyl-palmitoyl transferase (MPT), acyl carrier protein (ACP), ketoacyl synthase (KS), ketoacyl reductase (KR), phosphopantetheinyl transferase (PPT), thioesterase (TE), malonyl-acetyl transferase (MAT) may be derived from (naturally occurring) FAS as listed in Table 1.

TABLE 1

FAS from organisms suitable for use according to embodiments of the invention

| GenBank accession number (UniProtKB/Swiss-Prot) | Source organism |
|---|---|
| EMS21161.1 (M7WSW5), EMS21268.1 (M7XM89) | Rhodosporidium toruloides |
| Fas1 (CEQ41577.1), Fas 2 (CEQ41181.1) | Sporidiobolus salmonicolor |
| CDH58408.1 | Lichtheimia corymbifera |
| CDS12520.1 | Absidia idahoensis var. thermophila |
| GAN07093.1 | Mucor ambiguus |
| EPB92410.1 (S2KJ19) | Mucor circinelloides f. circinelloides |
| CEP14499.1 | Parasitella parasitica |
| ADN94479.1 (E2DDL2) | Amylomyces rouxii |
| XP_004364985.1 | Capsaspora owczarzaki |
| XP_008874394.1 | Aphanomyces invadans |
| XP_008613180.1 (T0QIJ7) | Saprolegnia diclina |
| XP_009832890.1 (W4GDM9) | Aphanomyces astaci |
| ETO83784.1 | Phytophthora parasitica |
| ETP47698.1 (W2ZK99) | |
| ETP52845.1 (W3A0S2) | |
| ETI55041.1 (V9FVE1) | |
| XP_008899478.1 (W2QNR7) | |
| XP_008891777.1 (W2RBA8) | |
| ETP19799.1 (W2XCY4) | |
| ETP24851.1 (W2XQ93) | |
| ETP19821.1 (W2XAT5) | |
| ETK94869.1 (W2HIB0) | |
| ETL48260.1 (W2JPB7) | |
| ETM01359.1 (W2LV63) | |
| XP_012208825.1 | Saprolegnia parasitica |
| XP_002997955.1 (D0NXJ3) | Phytophthora infestans |
| XP_002901724.1 (D0NFR3) | |
| XP_009519236.1 (G4YZ90) | Phytophthora sojae |
| XP_009519258.1 (G4Z031) | |
| (H3H6B1) | Phytophthora ramorum |
| (H3GFG1) | |
| (H3GFV5) | |
| ABJ98780.1 (A0FJY8) | Schizochytrium sp. ATCC 20888 |
| KFH67626.1 | Mortierella verticillata |
| Fas1 KGK40757.1, Fas2 KGK36891.1 | Pichia kudriavzevii |
| CCA25392.1 (F0WVF1) | Albugo laibachii |
| CCI41838.1 | Albugo candida |
| KGK36891.1 | Issatchenkia orientalis |
| (M4BNV4.1) | Hyaloperonospora arabidopsidis |
| (K3WEQ6.1) | Pythium ultimum |
| (DOE Joint Genome Institute) | |
| Fas 203878_jgiJGI | Lichtheimia hyalospora |
| Fas 606355_jgi | Mortierella elongata |
| Fas 315358_jgi | Backusella circina |
| Fas 10860_Jgi | Coemansia reversa |
| PPT 86596 | |
| 65122_jgi | Piromyces sp. E2 |
| 38102_jgi | |
| | Peniophora aff. cinerea |
| | Martensiomyces pterosporus |
| | Rhodotorula graminis |
| | Sporobolomyces linderae |
| | Sporobolomyces roseus |
| Fas1 17435, Fas2 19103 | Rhodotorula sp. JG-1b |
| Fas 537721_jgi | Phytophthora capsici |
| Fas 86957_jgi | Schizochytrium aggregatum |
| Fas 83486_jgi | Aurantiochytrium limacinum |
| Fas AKV56231 | Aurantiochytrium mangrovei |
| Fas 103951_jgi | Aplanochytrium kerguelense |
| | Phytophthora cinnamomi var cinnamomi |
| Fas1 (311302) Fas2 (346975) | Meredithblackwellia eburnea |
| Fas1 EGU11303 Fas2 ( ) | Rhodotorula glutinis |
| Fas1 EGG10429, Fas 2 ( ) | Melampsora larici-populina 98AG31 |

The skilled person will understand that beside the FAS/organisms listed in Table 1, additional FAS and organisms may be identified which are suitable according to the present invention, such as without limitation FAS (subunit) which also comprise at least two ACP domains. This may be done for instance by sequence alignments. Methods for comparing sequences and determining sequence identity are well known in the art. By means of example, percentage of sequence identity refers to a percentage of identical nucleic acids or amino acids between two sequences after alignment of these sequences. Alignments and percentages of identity can be performed and calculated with various different programs and algorithms known in the art. Preferred alignment algorithms include BLAST (Altschul, 1990; available for instance at the NCBI website) and Clustal (reviewed in Chenna, 2003; available for instance at the EBI website). Preferably, BLAST is used to calculate the percentage of identity between two sequences, such as the "Blast 2 sequences" algorithm described by Tatusova and Madden 1999 (FEMS Microbiol Lett 174: 247-250), for example using the published default settings or other suitable settings (such as, e.g., for the BLASTN algorithm: cost to open a gap=5, cost to extend a gap=2, penalty for a mismatch=−2, reward for a match=1, gap x_dropoff=50, expectation value=10.0, word size=28; or for the BLASTP algorithm: matrix=Blosum62, cost to open a gap=11, cost to extend a gap=1, expectation value=10.0, word size=3).

By means of example, ACP sequences (as well as FAS (subunit) sequences in general, or selected domain sequences of FAS (subunit), such as acetyl-transferase (AT), enoyl reductase (ER), dehydratase (DH), malonyl-palmitoyl transferase (MPT), acyl carrier protein (ACP), ketoacyl synthase (KS), ketoacyl reductase (KR), phosphopantetheinyl transferase (PPT), thioesterase (TE), malonyl-acetyl transferase (MAT)) may for instance be aligned with sequences as described in Zhu et al. (2012) "A multi-omic map of the lipid-producing yeast *Rhodosporidium toruloides*"; Nat Commun; 3:1112 (doi: 10.1038/ncomms2112), which is explicitly incorporated herein in its entirety by reference.

In certain embodiments, the (naturally occurring) FAS (subunit) has a protein sequence as set forth in SEQ ID NO: 8, 9, 10, 14, or 20, or a functional fragment, variant or orthologue thereof, or has a coding sequence encoding the protein sequence as set forth in SEQ ID NO: 8, 9, 10, 14, or 20, or a functional fragment, variant or orthologue thereof.

In certain embodiments the FAS (subunit) as modified by replacing an ACP domain with a TE domain has a protein sequence as set forth in SEQ ID NO: 11 or 12, or a functional fragment, variant or orthologue thereof, or has a coding sequence encoding the protein sequence as set forth in SEQ ID NO: 11 or 12 or a functional fragment, variant or orthologue thereof.

In certain embodiments the FAS (subunit) is modified by adding a TE domain before or after the ACP domain and has a protein sequence as set forth in SEQ ID NO: 17 or 18, or a functional fragment, variant or orthologue thereof, or has a coding sequence encoding the protein sequence as set forth in SEQ ID NO: 17 or 18 or a functional fragment, variant or orthologue thereof.

In certain embodiments, the FAS (subunit) or the FAS (subunit) encoding polynucleotide sequence, as modified by introducing a TE domain (or replacing an ACP domain with a TE domain), comprises or consists of (a polynucleotide sequence encoding, preferably from 5' to 3)':

AT, ER, DH, MPT, ACP, TE, KS, KR, and PPT;
AT, ER, DH, MPT, TE, ACP, KS, KR, and PPT;
AT, ER, DH, MPT, ACP, TE, KS, and KR;
AT, ER, DH, MPT, TE, ACP, KS, and KR;
AT, ER, DH, MPT, ACP, TE, and KS;
AT, ER, DH, MPT, TE, ACP, and KS;
AT, ER, DH, MPT, ACP, and TE;
AT, ER, DH, MPT, TE, and ACP;
ER, DH, MPT, ACP, TE, KS, KR, and PPT;
ER, DH, MPT, TE, ACP, KS, KR, and PPT;
DH, MPT, ACP, TE, KS, KR, and PPT;
DH, MPT, TE, ACP, KS, KR, and PPT;
MPT, ACP, TE, KS, KR, and PPT;
MPT, TE, ACP, KS, KR, and PPT;
ACP, TE, KS, KR, and PPT;
TE, ACP, KS, KR, and PPT;
TE and ACP;
ACP and TE;
MPT, ACP, TE, and KS; or
MPT, TE, ACP, and KS;
wherein said TE is preferably heterologous compared to said AT, ER, DH, MPT, ACP, KS, KR, and/or PPT, and wherein said AT, ER, DH, MPT, ACP, KS, KR, and/or PPT are preferably not heterologous compared to each other.

As described herein, in certain embodiments (at least) one of the ACP domains in the naturally occurring FAS (subunit) comprising (at least) two ACP domains is replaced by a TE domain. In certain other embodiments, a TE is introduced (directly) upstream or downstream of the ACP of FAS (subunit).

As used herein, the term "replaced" refers to deletion of the ACP domain or the ACP encoding nucleotide sequence and insertion of the TE domain or TE encoding nucleotide sequence at the location of the deleted ACP domain or ACP encoding nucleotide sequence. Replacing of the ACP domain or ACP encoding nucleotide sequences by a TE domain or TE encoding sequence can be done by techniques known in the art, including standard cloning techniques. By means of example, and without limitation, the FAS gene sequence, or part of the FAS gene sequence (i.e. a FAS subunit, such as for instance a partial FAS nucleotide sequence comprising a nucleotide sequence encoding an ACP domain; or for instance (part of) a FAS1 or FAS2 sequence which comprises a nucleotide sequence encoding an ACP domain) can be cloned in vitro. Via standard cloning techniques, including for instance the use of PCR, restriction enzymes or in vitro homologous recombination, the nucleotide sequence encoding ACP may be removed and replaced with a nucleotide sequence encoding TE. In certain embodiments, the resulting recombinant polynucleic acid may be introduced in a prokaryotic or eukaryotic cell as defined herein elsewhere, by techniques known in the art. The skilled person will understand that replacing the ACP encoding sequence with a TE encoding sequence preferably, but not necessarily, entails deletion of the entire ACP coding sequence. It can be that part or all of the original ACP sequence remains. For instance, the TE encoding sequence may be inserted into the ACP encoding sequence, such as to disrupt the ACP encoding sequence to the extent that no functional ACP results. Preferably however, the entide coding sequence of ACP, or most of the coding sequence of ACP is deleted, such as at least 80%, preferably at least 90%, more preferably at least 95% of the coding sequence of ACP is deleted.

As used herein, the term "thioesterase" refers to an enzyme which catalyses the hydrolysis of an ester into an acid and an alcohol, specifically at thiol group. Non-limiting examples of thioesterases include without limitation acetyl-coA hydrolase, palmitoyl-coA hydrolase, succinyl-coA hydrolase, formyl-coA hydrolase, acyl-coA hydrolase, etc. Preferred thioesterases as referred to herein are acyl-ACP/CoA thioesterases, preferably acyl-ACP/CoA thioesterases having specificity for and producing or resulting in the release of SOFA and/or MCFA. Non limiting examples of suitable thioesterases for use in the aspects according to the invention as described herein are listed in Table 2. Accordingly, in certain embodiments, the thioesterase is as specified in Table 2 or derived from an organism listed in Table 2.

TABLE 2

TE from organisms suitable according to embodiments of the invention

| GenBank accession number (UniProtKB/Swiss-Prot) | Source organism | Gene | Preferential product produced |
|---|---|---|---|
| AAC73596.1 | E. coli | tesA without leader sequence | $C_{18:1}$ |
| AAC73555.1 | E. coli | tesB | |
| AAA34215.1 (Q41635); AAC49001.1 | Umbellularia Californica | fatB | $C_{12:0}$ |
| AAC49269.1 (Q39513) | Cuphea hookeriana | fatB2 | $C_{8:0}$-$C_{10:0}$ |
| AAC49269.1; AAC72881.1 | Cuphea hookeriana | fatB3 | $C_{14:0}$-$C_{16:0}$ |
| AAC49151.1 (Q39473) | Cinnamonum camphorum | fatB | $C_{14:0}$ |
| CAA85388.1 | Arabidopsis thaliana | fatB | $C_{16:1}$ |
| NP_189147.1; NP_193041.1 | Arabidopsis thaliana | fatA | $C_{18:1}$ |
| CAC39106.1 | Bradyrhiizobium japonicum | fatA | $C_{18:1}$ |
| AAC72883.1 | Cuphea hookeriana | fatA | $C_{18:1}$ |
| AAL79361.1 | Helianthus annus | fatA1 | |
| JF338905.1 | Cocos nucifera | FatB3 | $C_{12:0}$ |
| AEM72519.1 | Cocos nucifera | fatB1 | $C_{8:0}$, $C_{14:0}$, $C_{16:0}$ |
| XM002515518.1 | Ricinus communis | fatA | $C_{16:1}$ $C_{18:1}$ |
| ABU96744.1 | Jatropha curcas | | $C_{14:0}$, $C_{16:0}$, $C_{16:1}$ |
| EEI82564.1 | Anaerococcus tetradius | | $C_{8:0}$ |
| CAB60830.1 | Cuphea lanceolata | fatB1 | $C_{8:0}$-$C_{18:1}$ |
| AEM72522.1 | Cuphea viscosissima | fatB1 | $C_{8:0}$, $C_{10:0}$ |
| AEM72524.1 | Cuphea viscosissima | fatB3 | $C_{14:0}$ |
| AAC74756.1 (P77781) | E. coli | ydiI | $C_{6:0}$-$C_{10:0}$ |
| AAO77182.1 | Bacteroides thetaiotaomicron | | $C_{4:0}$, $C_{6:0}$ |
| CAH09236.1 | Bacteroides fragilis | | $C_{4:0}$-$C_{16:1}$ |
| EET61113.1 | Marvinbryantia formatexigens Bryantella formatexigens | | $C_{4:0}$-$C_{16:1}$ |
| ABK63754.1 | Lactobacillus brevis | | $C_{8:0}$ |
| NM_145444.1 | Mus musculus | ACOT5 | $C_{16:0}$, $C_{18:0}$ |
| KF543781.1 | Lindera communis | LcFatB | $C_{10:0}$, $C_{12:0}$ |
| AAC49179.1 | Cuphea palustris | CpFatB1 | $C_{8:0}$, $C_{10:0}$ |
| U38189.1 | Cuphea palustris | CpFatB2 | $C_{14:0}$, $C_{16:0}$ |
| ADE82503.1 | Prevotella ruminicola | Pr655 | $C_{4:0}$, $C_{6:0}$, $C_{8:0}$ |
| KC675178.1 | Cuphea pulcherrima | FatB3 | $C_{8:0}$, $C_{10:0}$ |
| AAB71731.1 | Ulmus americana | | $C_{8:0}$, $C_{10:0}$ |
| AAG43857.1 | Iris germanica | | $C_{14:0}$, $C_{16:0}$, $C_{16:1}$ |
| AAG43858.1 | Iris germanica | | $C_{14:0}$, $C_{16:0}$, $C_{16:1}$ |
| EER87824.1 | Sorghum bicolor | | $C_{14:0}$, $C_{16:0}$, $C_{16:1}$ |
| EER88593.1 | Sorghum bicolor | | $C_{14:0}$, $C_{16:0}$, $C_{16:1}$ |
| AAD42220.1 | Elaeis guineensis | | $C_{8:0}$, $C_{14:0}$, $C_{16:1}$ |
| EDQ65090.1 | Physcomitrella patens | | $C_{14:0}$, $C_{16:1}$ |
| EER96252.1 | Sorghum bicolor | | $C_{14:0}$, $C_{16:0}$, $C_{16:1}$ |
| EES11622.1 | Sorghum bicolor | | $C_{14:0}$, $C_{16:0}$, $C_{16:1}$ |
| EEH52851.1 | Micromonas pusilla | | $C_{14:1}$, $C_{16:0}$, $C_{16:1}$ |
| ACL08376.1 | Desulfovibrio vulgaris | | $C_{8:0}$, $C_{12:1}$, $C_{14:1}$ |
| ABR43801.1 | Parabacteroides distasonis | | $C_{8:0}$, -$C_{14:1}$ |
| ABG82470.1 | Clostridium perfringens | | $C_{6:0}$, $C_{8:0}$ |
| EEG55387.1 | Clostridium asparagiforme | | $C_{14:1}$ |
| EDV77528.1 | Geobacillus sp. | | $C_{12:1}$, $C_{14:1}$ |
| BAH81730.1 | Streptococcus dysgalactiae | | $C_{8:0}$ |
| CAD63310.1 | Lactobacillus plantarum | | $C_{8:0}$ |
| CAE80300.1 | Bdellovibrio bacteriovorus | | $C_{8:0}$, $C_{14:1}$ |

TABLE 2-continued

TE from organisms suitable according to embodiments of the invention

| GenBank accession number (UniProtKB/Swiss-Prot) | Source organism | Gene | Preferential product produced |
|---|---|---|---|
| ABN54268.1 | Clostridium thermocellum | | $C_{14:1}$ |
| CAL21736.1 | Yersinia pestis | YpTesB | $C_{4:0}$, -$C_{12:0}$ |
| AAB71665.1 | Homo sapiens | ACOT8 | $C_{2:0}$, -$C_{18:0}$ |
| AAR21571.1 | Arabidopsis thaliana | ACH2 | $C_{12:0}$, -$C_{18:0}$ |
| NP_012553.1 | Saccharomyces cerevisiae | TES1 | |
| YP_598492.1 | Streptococcus pyogenes | | $C_{12:0}$, $C_{14:0}$ |
| AAB71729.1 | Myristica fragrans | | $C_{14:0}$ |
| AAC49783.1 | Cuphea wrightii | | $C_{12:0}$, $C_{14:0}$ |
| AAC49784.1 | Cuphea wrightii | | $C_{10:0}$, -$C_{14:0}$ |
| NM_022705.1 | Rattus norvegicus | TEII | $C_{10:0}$, $C_{12:0}$ |
| NP_666033.1 | Mus musculus | TEII | $C_{8:0}$ |
| XP_008266550.1 | Otyctolagus cuniculus | TEII | $C_{8:0}$, $C_{10:0}$ |
| WP_004921669.1 | Acinetobacter baylyi | AcTesA | $C_{6:0}$-$C_{14:0}$ |

The skilled person will understand that beside the TE/organisms listed in Table 2, additional TE and organisms may be identified which also comprise a suitable TE for use according to the invention. This may be done for instance by sequence alignments, as detailed herein elsewhere.

In certain embodiments, the TE is selected from AcTesA (derived from *Acinetobacter baylyi*; represented by genbank accession number WP_004921669.1), TEII (derived from *Mus musculus*; represented by genbank accession number NP_666033.1), TEII (derived from *Rattus norvegicus*; represented by genbank accession number NM_022705.1), YpTesB (derived from *Yersinia pestis*; represented by genbank accession number CAL21736.1), fatB1 (derived from *Cocos nucifera*; represented by genbank accession number AEM72519.1).

In certain embodiments, the TE has a protein sequence as set forth in SEQ ID NO: 13, or a functional fragment, variant or orthologue thereof, or has a coding sequence encoding the protein sequence as set forth in SEQ ID NO: 13 or a functional fragment, variant or orthologue thereof.

In an aspect, the invention relates to a protein or polypeptide encoded by the polynucleic acid as described herein, according to the various embodiments.

In a further aspect, the invention relates to a vector comprising the polynucleic acid as described herein, according to the various embodiments, or a vector comprising a polynucleic acid encoding the polypeptide as described herein according to the various embodiments.

By "vector" is meant a polynucleotide molecule, preferably a DNA molecule derived, for example, from a plasmid, bacteriophage, or plant/animal virus, into which a polynucleotide can be inserted or cloned. A vector preferably contains one or more unique restriction sites and can be capable of autonomous replication in a defined host cell, or be integrable with the genome of the defined host such that the cloned sequence is reproducible. The choice of the vector will typically depend on the compatibility of the vector with the host cell into which the vector is to be introduced.

According to an embodiment of the present invention, the expression construct is an expression vector, suitable for transformation into host organisms, preferably bacteria, and suitable for maintenance and/or expression of the polynucleic acid according to the present invention as described herein in a transformed host cell.

Vectors of the present invention can be operable as cloning vectors or expression vectors in the selected host strain. Numerous vectors are known to practitioners skilled in the art, and selection of an appropriate vector is a matter of choice. The vectors may, for example, be the pASK-IBA3C expression vector (IBA-life sciences), pUR5750 transformation vector (de Groot et al. 1998 Nature Biotechnology 16, 839-842), the pCGHT3 transformation vector (Chambers et al. 1988 Gene, Volume 68, Issue 1: 15; Scholtmeyer et al. 2001 Appl. Environ. Microbiol. 67(1): 481).

An "expression vector" is a construct that can be used to transform a selected host cell and provides for expression of a coding sequence in the selected host. Expression vectors can for instance be cloning vectors, binary vectors or integrating (e.g. recombination vectors, including homologous recombination, or random integration) vectors. The invention thus also relates to a vector comprising any of the polynucleic acids described herein. Said vector may further comprise regulatory sequences for controlling expression of the polynucleic acid in said host cell. In general, expression involves the use of an expression vector that is able to replicate efficiently in a host cell, such that the host cell accumulates many copies of the expression vector and, in turn, synthesizes high levels of a desired product encoded by the expression vector.

The terms "regulatory sequences" and "control sequence" used herein are to be taken in a broad context and refer to regulatory nucleic acid sequences capable of driving and/or regulating expression of the sequences to which they are ligated (covalently linked) and/or operably, linked. The control sequences differ depending upon the intended host organism and upon the nature of the sequence to be expressed. For expression of a protein in prokaryotes, the control sequences generally include a promoter, a ribosomal binding site, and a terminator. In eukaryotes, control sequences generally include promoters, terminators and, in some instances, enhancers, and/or 5' and 3' untranslated sequences. The term 'control sequence' is intended to include, at a minimum, all components necessary for expression, and may also include additional advantageous components. According to a preferred embodiment of the present invention, the control sequence is operable in a host cell as defined herein elsewhere. The term "control sequence"

encompasses a promoter or a sequence capable of activating or enhancing expression of a nucleic acid molecule in a host cell.

Expression and cloning vectors usually contain a promoter that is recognized by the host organism and is (covalently and) operably linked to the nucleic acid encoding the polypeptide of interest. Promoters are untranslated sequences located upstream (5') to the start codon of a structural gene (generally within about 100 to 1000 bp) that control the transcription and translation of a particular nucleic acid sequence, such as that encoding a fusion protein as defined herein, to which they are operably linked. Such promoters typically fall into two classes, inducible and constitutive. Inducible promoters are promoters that initiate increased levels of transcription from nucleic acid under their control in response to some change in culture conditions, e.g., the presence or absence of a nutrient or a change in temperature. At this time, a large number of promoters recognized by a variety of potential host cells are well known. These promoters are operably linked to nucleic acid encoding the polypeptide of interest by removing the promoter from the source nucleic acid by restriction enzyme digestion and inserting the isolated promoter sequence into the vector. Both the naturally occurring promoter sequence and many heterologous promoters may be used to direct amplification and/or expression of the polypeptide of interest. In general, plasmid vectors containing promoters and control sequences that are derived from species compatible with the host cell are used with these hosts. The vector ordinarily carries one or more replication sites as well as marker sequences, which are capable of providing phenotypic selection in transformed cells.

According to one embodiment of the invention, the vectors comprise a constitutive promoter. Examples of constitutive promoters suitable for the constructs and methods according to the present invention include but are not limited to the CaMV35S promoter, GOS2, actin promoter, ubiquitin promoter, thiolase promoter.

According to another embodiment of the invention, the vectors comprise an inducible promoter. Examples of inducible promoters suitable for the constructs and methods according to the present invention include but are not limited to the lac promoter or xylose inducible promoter Optionally, the present expression vectors will also contain sequences necessary for the termination of transcription and for stabilizing the mRNA, and may thus contain one or more transcription termination sequences. The term "transcription termination sequence" encompasses a control sequence at the end of a transcriptional unit, which signals 3' processing and termination of transcription. Additional regulatory elements, such as transcriptional or translational enhancers, may be incorporated in the expression construct.

The expression constructs of the invention may further include an origin of replication that is required for maintenance and/or replication in a specific cell type. One example is when an expression construct is required to be maintained in a cell as an episomal genetic element (e.g. plasmid or cosmid molecule). Preferred origins of replication include, but are not limited to the f1-ori, colE1 on, and Gram+ bacteria origins of replication.

The expression construct may optionally comprise a selectable marker gene. As used herein, the term "selectable marker gene" includes any gene, which confers a phenotype on a cell in which it is expressed to facilitate the identification and/or selection of cells which are transfected or transformed with an expression construct of the invention. Typical selection marker genes encode proteins that (a) confer resistance to antibiotics or other toxins such as chloramphenicol, zeocin (sh ble gene from *Streptoalloteichus hindustanus*), genetecin, melibiase (MELS), hygromycin (aminoglycoside antibiotic resistance gene from *E. coli*), ampicillin, tetracycline, or kanamycin (kanamycin resistance gene of Tn903), (b) complement auxotrophic deficiencies of the cell. Two prominent examples of auxotrophic deficiencies are the amino acid leucine deficiency (e.g. LEU2 gene) or uracil deficiency (e.g. URA3 gene). Cells that are orotidine-5'-phosphate decarboxylase negative (ura3-) cannot grow on media lacking uracil. Thus a functional URA3 gene can be used as a marker on a cell having a uracil deficiency, and successful transformants can be selected on a medium lacking uracil. Only cells transformed with the functional URA3 gene are able to synthesize uracil and grow on such medium. If the wild-type strain does not have a uracil deficiency (as is the case with *I. orientalis*, for example.), an auxotrophic mutant having the deficiency must be made in order to use URA3 as a selection marker for the strain. Methods for accomplishing this are well known in the art. Preferred selection makers include the zeocin resistance gene, G418 resistance gene, hygromycin resistance gene. The selection marker cassette typically further includes a promoter and terminator sequence, operatively linked to the selection marker gene, and which are operable in the host strain. Visual marker genes may also be used and include for example beta-glucuronidase (GUS), luciferase and Green Fluorescent Protein (GFP).

Construction of suitable vectors containing one or more of the above listed components and including the desired coding and control sequences employs standard ligation techniques. Isolated plasmids or nucleic acid fragments are cleaved, tailored, and religated in the form desired to generate the plasmids required.

As an alternative to the above described expression vectors, being it inducible or constitutive expression vectors, in certain embodiments, the vector as described herein does not comprise regulatory sequences responsible for expression of the protein encoded by the polynucleic acid as described herein. This may for instance be the case for integration or recombination vectors, as is known in the art. By means of example, and without limitation, through recombination, an endogenous FAS gene, or part thereof may be replaced by the polynucleic acid according to the invention as described herein. In this way, the host cell which originally comprised a naturally occurring FAS gene (such as, but not limited to, a FAS gene encoding (at least) two ACP domains), now comprises a recombinant FAS gene comprising a TE domain, under control of the endogenous promoter. Alternatively, random integration may be performed, in which case, the polynucleic acid according to the invention as described herein, preferably is operably linked to one or more regulatory sequences, as described herein elsewhere, such as for instance a constitutive or inducible promoter.

Genetic modification of the host strains is accomplished in one or more steps via the design and construction of appropriate vectors and transformation of the host strain with those vectors. Electroporation and/or chemical (such as calcium chloride- or lithium acetate-based) transformation methods or *Agrobacterium tumefaciens*-mediated transformation methods as known in the art can be used. The vectors can either be cut with particular restriction enzymes or used as circular DNA. The vector used for genetic modification of the host strains may be any vector so long as it can integrate in the genome of the host strain.

Successful transformants (comprising the polynucleic acid or the vector as described herein episomally or genomically integrated) can be selected for in known manner, by taking advantage of the attributes contributed by the marker gene, or by other characteristics (such as ability to produce fatty acids, inability to produce lactic acid or lactate, inability to produce acetic acid or acetate, or ability to grow on specific substrates) contributed by the inserted genes. Screening can be performed by PCR or Southern analysis to confirm that the desired insertions and deletions have taken place, to confirm copy number and to identify the point of integration of genes into the host strain's genome. Activity of the enzyme encoded by the inserted gene and/or lack of activity of enzyme encoded by the deleted gene can be confirmed using known assay methods.

In an aspect, the invention relates to a host cell, in particular a recombinant host cell, preferably a prokaryotic or eukaryotic host cell, expressing or capable of expressing the FAS and TE as described herein, or comprising the polynucleic acid, the polypeptide, or the vector as described herein. Preferably, the host cell expresses or is capable of expressing, such as inducibly or conditionally expressing, the polypeptide encoded by the polynucleic acid according to the invention as described herein. As detailed above, the reference to a recombinant host cell implies that the host cell comprises at least one foreign or heterologous (i.e. non-native) genetic element, more particularly a polynucleotide sequence encoding a FAS(subunit) and/or a polynucleic acid encoding a TE. More particularly, the polynucleic acid encoding a FAS (subunit) is a polynucleic acid which enclosed a FAS which does not comprise a TE domain, more particularly a FAS which is naturally devoid of a TE, most particularly a fungal FAS. In particular embodiments, the heterologous polynucleic acid is a naturally occurring nucleic acid.

In a related aspect, the invention relates to a host cell, in particular a recombinant host cell, preferably a prokaryotic or eukaryotic host cell, expressing or capable of expressing, such as inducibly or conditionally expressing, a FAS (subunit) gene sequence originating from a naturally occurring FAS (subunit) gene (preferably devoid of TE) and further expressing or capable of expressing a (heterologous) TE, such as for instance having a (heterologous) TE nucleotide sequence inserted (preferably (directly) upstream or downstream of ACP of said FAS (subunit)), wherein optionally said FAS (subunit) has at least two ACP encoding nucleotide sequences (preferably in tandem), wherein one of said ACT encoding nucleotide sequences is replaced by a TE encoding nucleotide sequence, wherein said FAS (subunit), ACP, and TE are as detailed herein elsewhere. The skilled person will understand that when reference is made to a FAS subunit, such as a FAS subunit comprising one or more ACP and an engineered TE, preferably directly up- or downstream of ACP, in order to reconstitute a functional FAS, capable of S/MCFA production, a separate subunit may need to be provided, which separate subunit comprises the enzymatic domains which are lacking from the FAS subunit comprising one or more ACP and an engineered TE. Accordingly, in certain embodiments, the invention relates to a host cell as referred to herein, expressing or capable of expressing, such as inducibly or conditionally expressing, multiple FAS subunit gene sequences, such as two FAS subunit gene sequences, originating from a naturally occurring FAS gene (preferably devoid of TE) and having a (heterologous) TE nucleotide sequence inserted (preferably (directly) upstream or downstream of ACP of the FAS subunit containing the ACP, wherein optionally one of said FAS subunits has at least two ACP encoding nucleotide sequences (preferably in tandem), wherein one of said ACT encoding nucleotide sequences is replaced by a TE encoding nucleotide sequence, wherein said FAS (subunit), ACP, and TE are as detailed herein elsewhere. In certain embodiments, the host cell comprises multiple FAS subunits, such that S/MCFA are produced, i.e. all necessary enzyme domains are provided on the multiple FAS subunits combined.

In certain embodiments, the host cell is a bacterial cell, a fungal cell (preferably a yeast cell), or an algae cell (preferably a microalgae cell).

In a preferred embodiment, the host cell is an oleaginous organism or a single cell organism, preferably an oleaginous single cell organism. In particular embodiments, the host cell is a yeast cell, such as an oleaginous yeast cell. In further particular embodiments, the host is selected from *Saccharomycetes* sp (e.g. *S. cerevisiae*, e.g. *S. cerevisiae* PWY12), *Yarrowia* sp. (e.g. *Y. lipolytica*), *Lipomyces* sp. (e.g. *L. starkeyi*), *Synechococcus* sp, *Chlamydomonas* sp. (e.g. *C. reinhardtii*), *Yarrowia* sp. (e.g. *Y. lipolytica*).

In certain embodiments, the host cell is the same species as the cell from which the naturally occurring FAS (subunit) as described herein is derived. In certain embodiments, the host cell is a different species as the cell from which the naturally occurring FAS (subunit) as described herein is derived.

In an aspect, the invention relates to a method for producing a recombinant cell as described herein, comprising the step of introducing the polynucleic acid, the vector, or a polynucleic acid encoding the polypeptide according to the invention as described herein, into a prokaryotic of eukaryotic cell, preferably a prokaryotic or eukaryotic cell as described herein elsewhere. Methods for introducing nucleic acids or proteins are known in the art, and include without limitation transformation, transfection, lipofection, electroporation, use of gene gun, etc. As indicated herein elsewhere, the polynucleic acid or vector which is introduced in the host cell may remain episomal (i.e. extrachromosomal) or may be partially or completely integrated into the host cell genome (either site directed integration or by random integration), and its encoded polypeptide may be constitutively, conditionally, or inducibly expressed.

In a related aspect, the invention provides a method for producing a recombinant cell as described herein, comprising the steps of:
(i) providing a prokaryotic or eukaryotic cell as defined herein and comprising a fatty acid synthase (FAS) gene or multiple FAS subunit genes, preferably a FAS (subunit) as defined herein elsewhere, optionally having at least two acyl carrier protein (ACP, preferably ACP as defined herein elsewhere) encoding nucleotide sequences; and
(ii) introducing or inserting a TE sequence, or replacing one of said ACP encoding nucleotide sequences with a TE encoding sequence, preferably TE as defined herein elsewhere.

This method may advantageously involve the use of knock-in technologies, as known in the art.

The invention is a further aspect relates to the use of the polynucleic acid, vector, polypeptide, or host cell as described herein, in the production of fatty acids, such as in particular short chain and/or medium chain fatty acids.

In a further aspect, the invention relates to a method for producing fatty acids, such as in particular short-chain and/or medium chain fatty acids, comprising the steps of:
(i) providing a recombinant prokaryotic or eukaryotic cell according to the invention as described herein; and
(ii) culturing said recombinant prokaryotic or eukaryotic cell under suitable culture conditions.

Methods for culturing the host cell as described herein are well known in the art. The skilled person will understand that suitable culturing methods include maintaining the host cell viable and metabolically active, and preferably allow growth and/or propagation of the host cell. Suitable culturing conditions include conditions allowing expression of the polypeptide (i.e. the modified FAS or FAS fragment, such as FAS subunit (e.g. FAS1 and/or FAS2), or fragments thereof) which is encoded by the polynucleic acid according to the invention as described herein. Suitable culturing conditions further include provision of the necessary ingredients allowing production of fatty acids, in particular short-chain and/or medium chain fatty acids.

In certain embodiments, the method for producing fatty acids as described herein, further comprises isolating and/or purifying the fatty acids. As used herein, isolating and/or purifying includes separating the fatty acids from the host cells, which may be done by any means known in the art, such as for instance centrifugation, filtration, etc. Further purification steps may include concentrating the fatty acids and/or removing impurities, as well as fatty acid fractionation. Suitable purification methods include for instance TLC.

The invention in a further aspect also provides a method for producing hydrocarbons (e.g. medium or short chain hydrocarbons) comprising performing the method for producing fatty acids according to the invention as described herein, further comprising either reduction, hydrogenation, decarboxylation or decarbonylation of said fatty acid to produce alkenes or alkanes. Optionally said fatty acids may be esterified prior to hydrogenation to produce hydrocarbons, as is known in the art.

The invention in a further aspect also provides a method for producing fatty aldehydes (e.g. medium or short chain fatty aldehydes) comprising performing the method for producing fatty acids according to the invention as described herein, further comprising reducing said fatty acids to fatty aldehydes, as is known in the art.

The invention in a further aspect also provides a method for producing fatty alcohols (e.g. medium or short chain fatty alcohols) comprising performing the method for producing fatty acids according to the invention as described herein, further comprising reducing said fatty acids to fatty aldehydes followed by alcohol dehydrogenase step to convert said fatty aldehydes to fatty alcohols, as is known in the art.

The decarboxylation, hydrogenation, esterification, reduction, etc. steps may be performed subsequent to the production of fatty acids, such as for instance after purification of said fatty acids, but may alternatively be performed simultaneously with production of said fatty acids, such as for instance by introduction of a suitable decarboxylase, carboxylic acid reductase, aldehyde reductase or alcohol dehydrogenase, decarbonylase or other relevant enzyme in the host cell, or a polynucleic acid encoding a suitable decarboxylase, aldehyde reductase or alcohol dehydrogenase, decarbonylase or other relevant enzyme, by means as described herein elsewhere. The skilled person will understand that other means and methods, such as including non-enzymatic methods, known in the art may be used to obtain the desired end-product.

The above disclosure will now be further described by means of the following non-limiting Examples and Figures, in which the figures show:

Example 1: Isolation of the FAS Encoding Genes or cDNA

The cell pellets harvested from 1 ml culture broth of *Rhodosporidium toruloides* in YPD medium (10 g/L yeast extract, 20 g/L peptone, and 20 g/L glucose) were immediately frozen in liquid nitrogen and stored at −70° C. Total RNA was isolated from about 30-50 mg cell samples using the FastRNA Pro Red Kit and FastPrep Instrument (Qbiogen, Inc., Irvine, USA) following the manufacturer's instructions, and the setting of FastPrep Instrument was 6.0 m/s for 60 s. The RNA concentration and quality were determined by Nanodrop ND1000 Spectrophotometer (ThermoFisher Scientific), while the RNA integrity was assessed by agarose gel electrophoresis. cDNA was synthesized by PrimeScript™ High Fidelity RT-PCR Kit (Takara Bio Inc.). Genomic DNA of *Saccharomyces cerevisiae* and *Aplanochytrium kerguelense* were extracted as described before (Burke, D., Dawson, D. & Stearns, T. (2000) Methods in yeast genetics: a *Cold Spring Harbor Laboratory* course manual, Cold Spring Harbor Laboratory Press, Plainview, N.Y.). Gene specific primers (Table 3) were used to amplify the open reading frame (ORF) of FAS genes.

Example 2: Construction of Recombinant Plasmids Expressing FAS and its Mutants

The fragments containing gene promoters and terminators of *Saccharomyces cerevisiae* was amplified from the genomic DNA of *Saccharomyces cerevisiae* CEN.PK113-11C (MATa SUC2 MAL2-8$^c$ ura3-52 his3-Δ1, kindly provided by P. Kötter, University of Frankfurt, Germany) or plasmids previously constructed (Buijs, N. A., Zhou, Y. J., Siewers, V. & Nielsen, J. (2015) Long-chain alkane production by the yeast *Saccharomyces cerevisiae*, *Biotechnol Bioeng.* 112, 1275-1279). And plasmids for expression of FAS complex in yeast were constructed by DNA assembler (Shao, Z., Zhao, H. & Zhao, H. (2009) DNA assembler, an in vivo genetic method for rapid construction of biochemical pathways, *Nucleic Acids Research.* 37, e16. and Zhou, Y. J., Gao, W., Rong, Q., Jin, G., Chu, H., Liu, W., Yang, W., Zhu, Z., Li, G., Zhu, G., Huang, L. & Zhao, Z. K. (2012) Modular Pathway Engineering of Diterpenoid Synthases and the Mevalonic Acid Pathway for Miltiradiene Production, *J Am Chem Soc.* 134, 3234-3241.). An overlap extension PCR protocol which was described before (Heckman K L, Pease L R. 2007. Gene splicing and mutagenesis by PCR-driven overlap extension. Nat. Protoc. 2:924-932.) was used to fusion multiple DNA fragments. Primers and templates of each PCR reactions are listed in Table 4. A yeast 2μ vector pYX212 containing a URA3 selection marker was used and linearized by digestion with restriction enzyme SphI and EcoRI. These fragments (listed in Table 4) accompanied with the linearized vector were transformed into *Saccharomyces cerevisiae* CEN.PK113-11C and selected on SC-URA plates (6.7 g/L yeast nitrogen base without amino acids (ForMedium, Norfolk, UK), 0.77 g/L complete supplement mixture without uracil (ForMedium, Norfolk, UK), 20 g/L glucose). Plasmids were extracted on the transformants by using the Zymoprep yeast plasmid miniprep II kit (Zymo Research, Orange, Calif.), and then transformed into *E. coli* DH5a competent cells. The *E. coli* colonies grown on Luria-Bertani (LB) agar plates with Ampicillin were picked and cultured for plasmid isolation. The extracted plasmids from *E. coli* were restriction digested to calculate the assembly fidelity. The expression cassettes of FAS were illustrated as FIG. 2

TABLE 3

Primers used for construction of plasmids expressing FAS

| Primer Name | Oligonucleotide sequence (5' to 3') | SEQ ID NO |
|---|---|---|
| pFAS-TPI1p-F | GAATTGGGGATCTACGTATGGTC | 21 |
| RtFAS1-TPI1p-R | CGACGTCCCAGTCACGCTCCGCGTCGCTCGGCCGTTCATTTTTAGTTTATGTATGTGTTT | 22 |
| RtFAS1-F | ATGAACGGCCGAGCGACGCGGAG | 23 |
| RtFAS1-R1 | AGACGGACGCAAAGTGGTTGAAGG | 24 |
| RtFAS1-R | TCAGAGCCCGCCGAAGACGTCGAGC | 25 |
| RtFAS1-F1 | ATGTCTACTCGATCAACGGTGTCCTCC | 26 |
| RtFAS1-FBA1t-F | CTCAAGCTCGACGTCTTCGGCGGGCTCTGAGTTAATTCAAATTAATTG | 27 |
| RtFAS2-ADH1t-R | GTCGCTTGCGCCGTCGTCATCGCCCAGAAGTAGGCGAATTTCTTATGATTTATG | 28 |
| RtFAS2-R | CTACTTCTGGGCGATGACGACGG | 29 |
| RtFAS2-F1 | CAACGCCGAAGTCGCCAACAAGC | 30 |
| RtFAS2-F | ATGGTCGCGGCGCAGGACTTG | 31 |
| RtFAS2-ACPI2AcTesA-F1 | GCGGTGGAGCTGCTGCTGCTGCC | 32 |
| RtFAS2-ACPII2AcTesA-R1 | CGGGCGCTCCACCGCCAGCTGCG | 33 |
| RtFAS2-4594-R | CGACAAGATGCAGGAGAAGCAGGACA | 34 |
| RtFAS2-4264-F | GACAAGGCAGCGAGCGGTGATG | 35 |
| RtFAS2-6628-R | GGTCGTCAACTACAACGTCGAGGGA | 36 |
| RtFAS2-6583-F | GGGATTGGAGGGCGACGAGGTGA | 37 |
| RtFAS2-ACPI2AcTesA-R1 | GGCGGCAGGCGCGGCAGCGACAGGA | 38 |
| RtFAS2-ACPI2AcTesA-F | CCCGCTCCTGTCGCTGCCGCGCCTGCCGCCAAGACTATATTGATATTGGGTGAC | 39 |
| RtFAS2-ACPI2AcTesA-R | TCGCGGGGGCAGCAGCAGCAGCTCCACCGCCGGCTAATGCACCCTTGATGTAAGGGTAAGC | 40 |
| RtFAS2-ACPII2AcTesA-F | CTCCGGCCGCAGCTGGCGGTGGAGCGCCCGCTAAGACTATATTGATATTGGGTGAC | 41 |
| RtFAS2-ACPII2AcTesA-R | GACAGCCGCGCCGCCTCCGCCTCCACCAGCTAATGCACCCTTGATGTAAGGGTAAGC | 42 |
| RtFAS2-ACPII2AcTesA-F1 | GCTGGTGGAGGCGGAGGCGGC | 43 |
| RtFAS2-R1 | ATGCCCTGGTCTGCCTTGTTGCC | 44 |
| RtFAS-TEF1p-R | GCGCGAGCGGCAAGTCCTGCGCCGCGACCATTTTGTAATTAAAACTTAGATTAG | 45 |
| TEF1p-F | ATAGCTTCAAAATGTTTCTACTC | 46 |
| TEF1p-HA-F | GAGTAAAAAGGAGTAGAAACATTTTGAAGCTATGGATCCCTAGCTCCAATTCGCCCTATA | 47 |
| pFAS-pYX212t-R | GCCGTAAACCACTAAATCGGAACC | 48 |
| TPI1p-ScFAS2-R | GCAAAATATGAGCTAATTCTTGCTCAACTTCCGGCTTCATTTTTAGTTTATGTATGTGTTT | 49 |
| ScFAS2-F | AAGCCGGAAGTTGAGCAAGAATTAG | 50 |
| ScFAS2-R1 | ACAGGTTCATCGGCAATCTCA | 51 |
| ScFAS2-F1 | TCAGAGCCGTGTCCATCACTT | 52 |

TABLE 3-continued

Primers used for construction of plasmids expressing FAS

| Primer Name | Oligonuleotide sequence (5' to 3') | SEQ ID NO |
|---|---|---|
| ScFAS2-R | CTATTTCTTAGTAGAAACGGCGACC | 53 |
| FBA1t-ScFAS2-F | GTCGCGGTCGCCGTTTCTACTAAGAAATAGGTTAATTCAAA TTAATTG | 54 |
| ADH1t-ScFAS1-R | CGACAACTGGGAAAAGTATGAACAATCCTAAGCGAATTTCT TATGATTATG | 55 |
| ScFAS1-R | GGATTGTTCATACTTTTCCCAG | 56 |
| ScFAS1-F1 | CTGCTGTCAAGCCTCGCCCACT | 57 |
| ScFAS1-R1 | TGTGGTAGGCTCGTCATCTGC | 58 |
| ScFAS1-F | GACGCTTACTCCACAAGACCA | 59 |
| TEF1p-ScFAS1-R | GGGTTAATGGTCTTGTGGAGTAAGCGTCCATTTTGTAATTA AAACTTAGATTAG | 60 |
| ScFAS2-ACPI2TE-R1 | GAGTCACCCAATATCAATATAGTCTTAATCTCAGCAGCTGC TGCAGCTGG | 61 |
| AcTesA-F | AAGACTATATTGATATTGG | 62 |
| AcTesA_ScACP_F | CCGCAGCTGGCGGTGGAGCGCCCGCTGCCGATGAACCTGTC AAGGC | 63 |
| ScFAS2-R2 | AAGATTGTTTAGCCCAGTTCC | 64 |
| ScFAS2-F2 | CGGTGTTGCTACTTCTTTCTC | 65 |
| ADH1t-F | GCGAATTTCTTATGATTTATGA | 66 |
| pFAS-FBA1t-F | ATAGTTTTTTAATGAGTATTGAATC | 67 |
| AcTesA_ScACP-R | GGCAGCAGCAGCAGCTCCACCGCCGGCAGCTGATGATAAGT CAACACC | 68 |
| AcTesA-R | ACCAGCTAATGCACCCTTGATG | 69 |
| ScFAS2-ACPII2TE-F1 | CCTTACATCAAGGGTGCATTAGCTGGTGCTAGCGCTAGTGG TGCTGCCGGT | 70 |
| pZWM-2p-F | AAGGGCCATGACCACCTGATGCACCAATTAGGTAGGTCTGG CTATGTCTATACCTCTGGCCGTCGCATCCCCGGTTCATTTT C | 71 |
| pZWM-AmpR-R | TTGGCAATTTTTTGCTCTTCTATATAACAGTTGAAATTTGA ATAAGAACATCTTCTCAAAGAGAGGCGGTTTGCGTATTGG | 72 |
| pZWM-KlURA3-F | TTTGAGAAGATGTTCTTATTCAAATTTCAACTGTTATATAGA AGAGCAAAAAATTGCCAATTCGATGATGTAGTTTCTGGTT | 73 |
| pZWM-KlURA3-R | CACCTTTCGAGAGGACGATGCCCGTGTCTAAATGATTCGAC CAGCCTAAGAATGTTCAACGTGATTCTGGGTAGAAGATCG | 74 |
| pZW M-TEF1p-F | GTTGAACATTCTTAGGCTGGTCGAATCATTTAGACACGGGC ATCGTCCTCTCGAAAGGTGATAGCTTCAAAATGTTTCTACT CC | 75 |
| TEF1p-R | ATTAAAACTTAGATTAGATTGC | 76 |
| TEF1p-AkFAS-F | GAAAGCATAGCAATCTAATCTAAGTTTTAATTACAAAATGG AACAACATAAAACTGAGAAAC | 77 |
| AkFAS-499-R | TTCTGTCGTTGTCAGGCGATGTA | 78 |
| AkFAS-149-F | TGTATGAAACTGGCACAGATGAG | 79 |
| AkFAS-5039-R | GTAAATGACGTGGTATTACTATGGA | 80 |
| AkFAS-4919-F | AGTTGACTGTTCGTTTCGGTGGA | 81 |
| AkFAS-10868-R | ATCGGTAGCAGTGTTTGACAGAGCA | 82 |

TABLE 3-continued

Primers used for construction of plasmids expressing FAS

| Primer Name | Oligonuleotide sequence (5' to 3') | SEQ ID NO |
|---|---|---|
| AkFAS-10610-F | TAGCGGGCGGGTATGATGACTTT | 83 |
| ADH1t-AkFAS-R | TTAATAATAAAAATCATAAATCATAAGAAATTCGCTTAATTTGTTATTGCTTGGGCTACT | 84 |
| ADH1t-F | GCGAATTTCTTATGATTTATGA | 85 |
| pZWM-ADH1t-R | GCCAGAGGTATAGACATAGCCAGACCTACCTAATTGGTGCATCAGGTGGTCATGGCCCTTCCGGTAGAGGTGTGGTCAATAAG | 86 |
| pZWM-R | GCCAGAGGTATAGACATAGCCA | 87 |
| pZWM-F | GTTGAACATTCTTAGGCTGG | 88 |
| AkFAS-6900-R | AATTTGTACAAAGTTGTTTTGA | 89 |
| AkFAS-6800-F | AAAAGTCCAAATTCGAACGAA | 90 |
| AkFAS-6300-R | CTTTTGAAGTTCATTCCCCAC | 91 |
| AkFAS-ACPI2TE-F | GGAGAAAGTGGGGAATGAACTTCAAAAGAAGACTATATTGATATTGGGTGAC | 92 |
| AkFAS-ACPI2TE-R | CACACTTTCGTTCGAATTTGGACTTTTTAATGCACCCTTGATGTAAGGGTAAGC | 93 |
| AkFAS-8000-R | AGCACTATCAACTGTCACCCT | 94 |
| AkFAS-7900-F | TGTAATCGTGCCACTCCAGAAC | 95 |
| AkFAS-ACPII2TE-F | GACTGTTCAAAACAACTTTGTACAAATTAAGACTATATTGATATTGGGTGAC | 96 |
| Ak FAS-ACPII2TE-R | GGACTACTATCACCTGAAGAGAGAGTACGTAATGCACCCTTGATGTAAGGGTAAGC | 97 |
| AkFAS-7400-F | CGTACTCTCTCTTCAGGTGATAG | 98 |
| dURA3-Up-F | AAACGACGTTGAAATTGAGGCTACTGCG | 99 |
| dURA3-UP-R | GAAGAAGAATGACCATACGTAGATCCCCAATTCGGACTAGGATGAGTAGCAGCACGTTCC | 100 |
| TPI1p-R | TTAGTTTATGTATGTGTTTTTTGTA | 101 |
| pFAS-FBA1t-R | GTAAGCTACTATGAAAGACTTTACA | 102 |
| TEF1p-KanMX-F | GAGTAAAAAAGGAGTAGAAACATTTTGAAGCTATAAGCTTCGTACGCTGCAGGTCG | 103 |
| dURA3-KanMX-R | CTGGCCGCATCTTCTCAAATATGCTTCCCCGACTCACTATAGGGAGACCG | 104 |
| URA3-Down-F | GGGAAGCATATTTGAGAAGATGCGGC | 105 |
| URA3-Down-R | GGAAACGCTGCCCTACACGTTCGC | 106 |
| ID-dURA3-UP | AGGGAAGACAAGCAACGAAA | 107 |
| ID-dURA3-DOWN | CGTCAAGGTCTGTTGAGTGC | 108 |

TABLE 4

PCR fragments used for the assembly of plasmids expressing the genes or ORFs of FAS

| Name | Length (bp) | Primer_1 | Primer_2 | Templates |
|---|---|---|---|---|
| pRtFAS-1 | 966 | pFAS-TPI1p-F | RtFAS1-TPI1p-R | pYX212 |
| pRtFAS-2 | 391 | RtFAS1-F | RtFAS1-R1 | cDNA of R. toruloides |

TABLE 4-continued

PCR fragments used for the assembly of plasmids expressing the genes or ORFs of FAS

| Name | Length (bp) | Primer_1 | Primer_2 | Templates |
|---|---|---|---|---|
| pRtFAS-3 | 1318 | pFAS-TPI1p-F | RtFAS1-R1 | Fusion products of pRtFAS-1 and 2 |
| pRtFAS-4 | 3801 | RtFAS1-F | RtFAS1-R | cDNA of *R. toruloides* |
| pRtFAS-5 | 236 | RtFAS1-F1 | RtFAS1-R | cDNA of *R. toruloides* |
| pRtFAS-6 | 505 | RtFAS1-FBA1t-F | RtFAS2-ADH1t-R | pKB16 |
| pRtFAS-7 | 406 | RtFAS2-R | RtFAS2-F1 | cDNA of *R. toruloides* |
| pRtFAS-8 | 1084 | RtFAS1-F1 | RtFAS2-F1 | Fusion products of pRtFAS-5, 6 and 7 |
| pRtFAS-9 | 5228 | RtFAS2-R | RtFAS2-ACPI2AcTesA-F1 | cDNA of *R. toruloides* |
| pRtFAS-10 | 3631 | RtFAS2-ACPII2AcTesA-R1 | RtFAS2-F | cDNA of *R. toruloides* |
| pRtFAS-11 | 248 | RtFAS2-R1 | RtFAS2-F | cDNA of *R. toruloides* |
| pRtFAS-12 | 443 | RtFAS2-TEF1p-R | TEF1p-F | pKB16 |
| pRtFAS-13 | 251 | TEF1p-HA-F | pFAS-pYX212t-R | pYX212 |
| pRtFAS-14 | 1049 | RtFAS2-R1 | pFAS-pYX212t-R | Fusion products of pRtFAS-11, 12 and 13 |
| pRtFAS-15 | 4594 | RtFAS2-R | RtFAS2-4594-R | pRtFAS-WT |
| pRtFAS-16 | 396 | RtFAS2-4264-F | RtFAS2-ACPII2AcTesA-F1 | pRtFAS-WT |
| pRtFAS-17 | 605 | RtFAS2-ACPII2AcTesA-F | RtFAS2-ACPII2AcTesA-R | pUC57-AcTesA |
| pRtFAS-18 | 72 | RtFAS2-ACPI2AcTesA-F1 | RtFAS2-ACPII2AcTesA-R1 | pRtFAS-WT |
| pRtFAS-19 | 1013 | RtFAS2-4264-F | RtFAS2-ACPII2AcTesA-F1 | Fusion products of pRtFAS-16, 17 and 18 |
| pRtFAS-20 | 2227 | RtFAS2-6583-F | RtFAS2-F | pRtFAS-WT |
| pRtFAS-21 | 607 | RtFAS2-ACPII2AcTesA-F | RtFAS2-ACPII2AcTesA-R | pUC57-AcTesA |
| pRtFAS-22 | 901 | RtFAS2-ACPII2AcTesA-R1 | RtFAS2-6628-R | pRtFAS-WT |
| pRtFAS-23 | 1520 | RtFAS2-ACPII2AcTesA-R1 | RtFAS2-6628-R | Fusion products of pRtFAS-18, 21 and 22 |
| pScFAS-1 | 967 | pFAS-TPI1p-F | TPI1p-ScFAS2-R | pYX212 |
| pScFAS-2 | 431 | ScFAS2-F | ScFAS2-R1 | Genomic DNA of *S. cerevisiae* |
| pScFAS-3 | 1361 | pFAS-TPI1p-F | ScFAS2-R1 | Fusion products of pScFAS-1 and 2 |
| pScFAS-4 | 5661 | ScFAS2-F | ScFAS2-R | Genomic DNA of *S. cerevisiae* |
| pScFAS-5 | 758 | ScFAS2-F1 | ScFAS2-R | Genomic DNA of *S. cerevisiae* |
| pScFAS-6 | 504 | FBA1t-ScFAS2-F | ADH1t-ScFAS1-R | pKB16 |
| pScFAS-7 | 302 | ScFAS1-R | ScFAS1-F1 | Genomic DNA of *S. cerevisiae* |
| pScFAS-8 | 1506 | ScFAS2-F1 | ScFAS1-F1 | Fusion products of pScFAS-5, 6 and 7 |
| pScFAS-9 | 6150 | ScFAS1-R | ScFAS1-F | Genomic DNA of *S. cerevisiae* |
| pScFAS-10 | 165 | ScFAS1-R1 | ScFAS1-F | Genomic DNA of *S. cerevisiae* |
| pScFAS-11 | 443 | TEF1p-ScFAS1-R | TEF1p-F | pKB16 |
| pScFAS-12 | 251 | TEF1p-HA-F | pFAS-pYX212t-R | pYX212 |
| pScFAS-13 | 969 | ScFAS2-R1 | pFAS-pYX212t-R | Fusion products of pScFAS-10, 11 and 12 |
| pScFAS-14 | 1365 | pFAS-TPI1p-F | ScFAS2-ACPI2TE-R1 | pScFAS-WT |
| pScFAS-15 | 443 | ScFAS2-F | ScFAS2-ACPI2TE-R1 | pScFAS-WT |
| pScFAS-16 | 619 | AcTesA-F | RtFAS2-ACPII2AcTesA-R1 | pRtFAS-ACPI2TE |
| pScFAS-17 | 843 | AcTesA_ScACP_F | ScFAS2-R2 | pScFAS-WT |
| pScFAS-18 | 1855 | ScFAS2-F | ScFAS2-R2 | Fusion products of pRtFAS-15, 16 and 17 |
| pScFAS-19 | 4944 | ScFAS2-F2 | ADH1t-F | pScFAS-WT |
| pScFAS-20 | 7188 | pFAS-FBA1t-F | pFAS-pYX212t-R | pScFAS-WT |
| pScFAS-21 | 1860 | pFAS-TPI1p-F | AcTesA_ScACP-R | pScFAS-WT |
| pScFAS-22 | 940 | ScFAS2-F | AcTesA_ScACP-R | pScFAS-WT |
| pScFAS-23 | 623 | RtFAS2-ACPII2AcTesA-F1 | AcTesA-R | pRtFAS-ACPII2TE |
| pScFAS-24 | 349 | ScFAS2-ACPII2TE-F1 | ScFAS2-R2 | pScFAS-WT |

TABLE 4-continued

PCR fragments used for the assembly of plasmids expressing the genes or ORFs of FAS

| Name | Length (bp) | Primer_1 | Primer_2 | Templates |
|---|---|---|---|---|
| pScFAS-25 | 1855 | ScFAS2-F | ScFAS2-R2 | Fusion products of pScFAS-22, 23 and 24 |
| pAkFAS-1 | 3744 | pZWM-2μ-F | pZWM-AmpR-R | pYX212 |
| pAkFAS-2 | 1404 | pZWM-KlURA3-F | pZWM-KlURA3-R | pWJ4402 |
| pAkFAS-3 | 466 | pZWM-TEF1p-F | TEF1p-R | pKB16 |
| pAkFAS-4 | 536 | TEF1p-AkFAS-F | AkFAS-499-R | Genomic DNA of *A. kerguelense* |
| pAkFAS-5 | 971 | pZWM-F | AkFAS-499-R | Fusion products of pAkFAS-3 and 4 |
| pAkFAS-6 | 4891 | AkFAS-149-F | AkFAS-5039-R | Genomic DNA of *A. kerguelense* |
| pAkFAS-7 | 5945 | AkFAS-4919-F | AkFAS-10868-R | Genomic DNA of *A. kerguelense* |
| pAkFAS-8 | 1852 | AkFAS-10610-F | ADH1t-AkFAS-R | Genomic DNA of *A. kerguelense* |
| pAkFAS-9 | 248 | ADH1t-F | pZWM-ADH1t-R | pKB16 |
| pAkFAS-10 | 2065 | AkFAS-10610-F | pZWM-R | Fusion products of pAkFAS-8 and 9 |
| pAkFAS-11 | 5682 | ADH1t-F | TEF1p-R | pAKFAS-WT |
| pAkFAS-12 | 1412 | AkFAS-4919-F | AkFAS-6300-R | pAKFAS-WT |
| pAkFAS-13 | 598 | AkFAS-ACPI2TE-F | AkFAS-ACPI2TE-R | pUC57-AcTesA |
| pAkFAS-13 | 72 | AkFAS-6800-F | AkFAS-6900-R | pAKFAS-WT |
| pAkFAS-15 | 2027 | AkFAS-4919-F | AkFAS-6900-R | Fusion products of pAkFAS-12, 13 and 14 |
| pAkFAS-16 | 5846 | AkFAS-6800-F | pZWM-R | pAKFAS-WT |
| pAkFAS-17 | 1982 | AkFAS-4919-F | AkFAS-6900-R | pAKFAS-WT |
| pAkFAS-18 | 600 | AkFAS-ACPII2TE-F | AkFAS-ACPII2TE-R | pUC57-AcTesA |
| pAkFAS-19 | 678 | AkFAS-7400-F | AkFAS-8000-R | pAKFAS-WT |
| pAkFAS-20 | 1293 | AkFAS-6800-F | AkFAS-8000-R | Fusion products of pAkFAS-13, 18 and 19 |
| pAkFAS-21 | 4796 | AkFAS-7900-F | pZWM-R | pAKFAS-WT |

Figure 3:
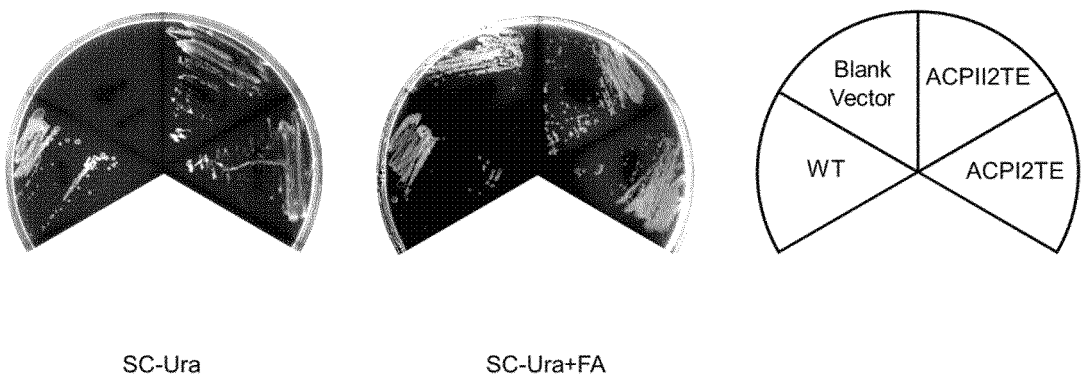
FIG. 3. Complementation of the RtFAS to the fatty acid auxotrophy of *Saccharomyces cerevisiae* PWY12 (MATα ura3 leu2 his3 trp1 can1 Δfas1::HIS3 Δfas2::LEU2).

1. pRtFAS-3, pRtFAS-4, pRtFAS-8, pRtFAS-9, pRtFAS-10, pRtFAS-14, and linearized vector pYX212 (L) were used for assembly of pRtFAS-WT;
2. pRtFAS-3, pRtFAS-4, pRtFAS-8, pRtFAS-9, pRtFAS-23, pRtFAS-20, pRtFAS-14 and linearized vector pYX212 (L) were used for assembly of pRtFAS-ACPI2TE;
3. pRtFAS-3, pRtFAS-4, pRtFAS-8, pRtFAS-15, pRtFAS-19, pRtFAS-10, pRtFAS-14 and linearized vector pYX212 (L) were used for assembly of pRtFAS-ACPII2TE;
4. pScFAS-3, pScFAS-4, pScFAS-8, pScFAS-9, pScFAS-13 and linearized vector pYX212 (L) were used for assembly of pScFAS-WT
5. pScFAS-14, pScFAS-18, pScFAS-19, pScFAS-20 and linearized vector pYX212 (L) were used for assembly of pScFAS-TE-ACP
6. pScFAS-21, pScFAS-25, pScFAS-19, pScFAS-20 and linearized vector pYX212 (L) were used for assembly of pScFAS-ACP-TE
7. pAkFAS-1, pAkFAS-2, pAkFAS-5, pAkFAS-6, pAkFAS-7 and pAkFAS-10 were used for assembly of pAkFAS-WT
8. pAkFAS-5, pAkFAS-6, pAkFAS-15, pAkFAS-16 and pAkFAS-11 were used for assembly of pAkFAS-ACPI2TE
9. pAkFAS-5, pAkFAS-6, pAkFAS-17, pAkFAS-20, pAkFAS-21 and pAkFAS-11 were used for assembly of pAkFAS-ACPII2TE Example 3: Function Verification of the FAS Genes The recombinant plasmids expressing FAS encoding genes or ORFs were transformed into FAS deficient strain PWY12 (MATα ura3 leu2 his3 trp1 cant Δfas1::HIS3 Δfas2::LEU2, Wenz, P., Schwank, S., Hoja, U. & Schüller, H.-J. (2001) A downstream regulatory element located within the coding sequence mediates autoregulated expression of the yeast fatty acid synthase gene FAS2 by the FAS1 gene product, *Nucleic Acids Research*. 29, 4625-4632.) by a lithium acetate/single-stranded carrier DNA/polyethylene glycol method (Daniel Gietz, R. & Woods, R. A. (2002) Transformation of yeast by lithium acetate/single-stranded carrier DNA/polyethylene glycol method, *Methods Enzymol.* 350, 87-96.). 0.5 mM palmitic acid and 0.5 mM stearic acid (5 mM stock solution in TWEEN 80/ethanol=1:1) were supplemented in the media if needed. The YPD medium with fatty acids was used to culture PWY12 for the transformation, the transfomants were selected on SC-URA+FA medium plates (6.7 g/L yeast nitrogen base without amino acids, 0.77 g/L complete supplement mixture without uracil, 20 g/L glucose, containing fatty acids). Single colonies were inoculated into "SC-URA+FA" medium to amplify the cells for 24-36 hours, then the cells was spin down and washed twice with steriled water, and grown in "SC-URA" media for 24 hours to exhaust fatty acid residues. After that, the cells were streaked onto "SC-URA" or "SC-URA+FA" plates to test the restoring of fatty acid autotroph. The complement test result was shown in FIG. 3.

Example 4: Short/Medium Chain Fatty Acids Production of Recombinant FAS

Recombinant transformants of *Saccharomyces cerevisiae* PWY12 expressing FAS genes or ORFs were pre-cultured in 2 ml Delft medium (Jensen, N. B., Strucko, T., Kildegaard, K. R., David, F., Maury, J., Mortensen, U. H., Forster, J., Nielsen, J. & Borodina, I. (2014) EasyClone: method for iterative chromosomal integration of multiple genes *Saccharomyces cerevisiae, FEMS Yeast Res.* 14, 238-248.) with 100 mg/L tryptophan overnight. The cells were inoculated into 20 ml "Delft+Trp" medium in 100 ml Erlenmeyer flask to achieve an initial optical density (OD at 600 nm) of 0.1. After culture for 48 hours, 4 ml culture broth was taken for analysis of extracellular fatty acids, the rest cell pellets were harvested by centrifugation, washed once with Millipore-Q water, and freezing dried for measurement of intracellular total fatty acids.

A modified method was developed for the extraction and esterification of extracellular S/MCFAs. Briefly, 0.5 ml 10% (w/v) NaCl, 0.5 ml glacial acetate (containing 10 ug Heptanoic acid and 10 ug Pentadecanoic acid as internal standards) and 2 ml 1:1 (v/v) chloroform/methanol were added to 4 ml culture broth in extraction tubes (16×100 mm PYREX® culture tubes and GPI 15-415 Threaded Screw Cap, Corning Inc., US). After vortex at 1800 rpm for 30 min, the mixtures were centrifuged at 3000 rpm for at least 10 min, and the lower chloroform phase was transferred into a clean extraction tube by a glass syringe. Fatty acid methyl esters (FAMEs) were generated by mixing 1 ml boron trifluoride/methanol (14%, w//w, Sigma-Aldrich) with 200 ul of chloroform extract, and esterification at room temperature for overnight. This is based on the ready and fast esterification of free fatty acids by boron trifluoride/methanol (Mitchell, J., Smith, D. M. & Bryant, W. M. D. (1940) Analytical Procedures Employing Karl Fischer Reagent.1 III. The Determination of Organic Acids, *J Am Chem Soc.* 62, 4-6.). The FAMEs were extracted by adding 1 ml H2O and 600 ul hexane, vortex at 1500 rpm for 10 min, and centrifugation at 1000 g for 10 min. 200 ul taken from the hexane phase was analysed by GC/MS. The intracellular total fatty acids were extracted and esterification by a previously described method with minor modification (Khoomrung, S., Chumnanpuen, P., Jansa-ard, S., Nookaew, I. & Nielsen, J. (2012) Fast and accurate preparation fatty acid methyl esters by microwave-assisted derivatization in the yeast *Saccharomyces cerevisiae, Appl Microbiol Biotechnol.* 94, 1637-1646.). The heptanoic acid and pentadecanoic acid were used as internal standards, and 1 ml hexane was used for extraction.

Figure 4:
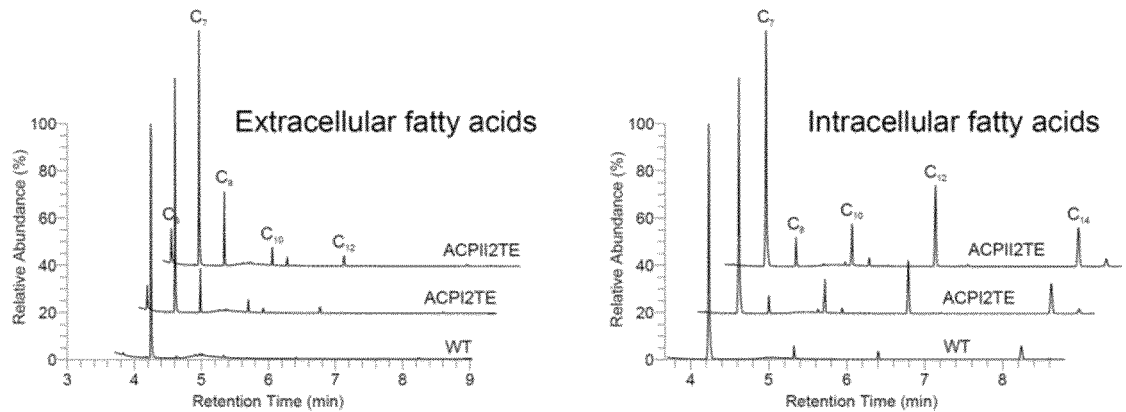
FIG. 4. Medium chain fatty acids (hexanoic acid, C6; octanoic acid, C8; decanoic acid, C10; and dodecanoic acid, C12) produced by RtFAS and it mutants. The heptanoic acid (C7) was used as internal standard.
Figure 5:
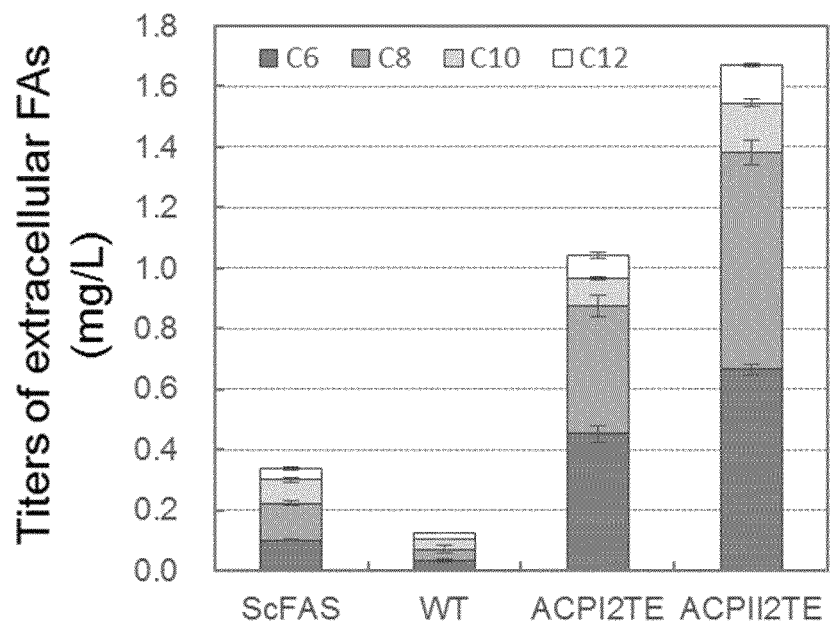
FIG. 5. Titers of extracellular fatty acids produced by *Saccharomyces cerevisiae* PWY12 expressing corresponding FASs including ScFAS from *Saccharomyces cerevisiae*, and FAS from *Rhodosporidium toruloides* (Wild type, WT; FAS/TE hybrid, ACPI2TE and ACPII2TE).
Figures 6, 7:
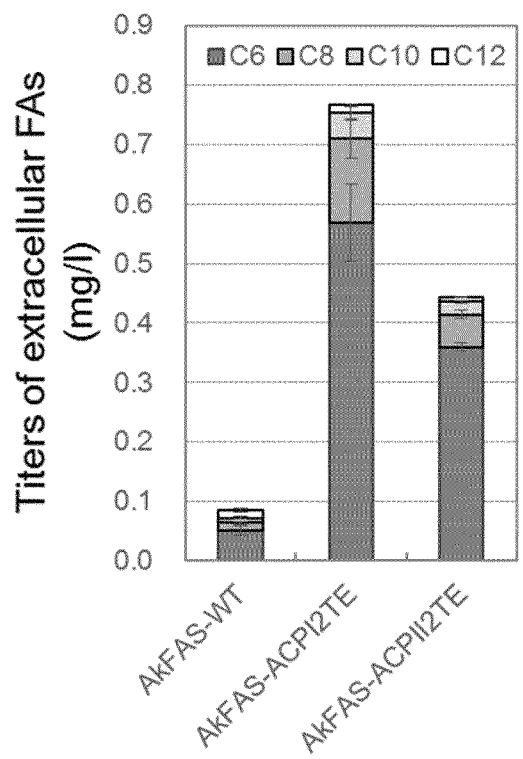
FIG. 6. Intracellular fatty acid composition of *Saccharomyces cerevisiae* PWY12 expressing corresponding FAS including ScFAS from *Saccharomyces cerevisiae*, and FAS from *Rhodosporidium toruloides* (wild type, WT; FAS/TE hybrid, ACPI2TE and ACPII2TE).
FIG. 7. Titers of extracellular fatty acids produced by *Saccharomyces cerevisiae* PWY12 expressing corresponding FAS from *Aplanochytrium kerguelense* (Wild type, AkFAS-WT; FAS/TE hybrid, AkFAS-ACPI2TE and AkFAS-ACPII2TE).
Figure 8:
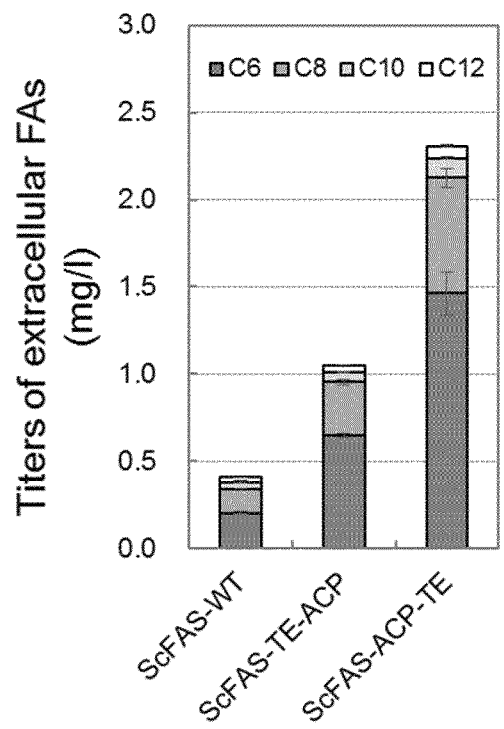
FIG. 8. Titers of extracellular fatty acids produced by *Saccharomyces cerevisiae* PWY12 expressing corresponding FAS from *Saccharomyces cerevisiae* (Wild type, ScFAS-WT; FAS/TE hybrid, ScFAS-TE-ACP and ScFAS-ACP-TE).

The extracted FAMEs were analyzed by a Thermo Scientific ISQ single quadrupole GC-MS system (Thermo Fisher Scientific Inc., USA) using a ZB-WAX column (30 m*0.25 mm*0.15 um, Phenomenex Inc., UK), and Helium as gas carrier (3 ml/min). 1 ul samples were injected (splitless, 240° C.), and oven temperature was set at 30° C. for 2 min; increased to 150° C. at a ramp rate of 40° C./min, hold for 2 min; increased to 250° C. at a ramp rate of 10° C./min, hold for 3 min. The compound identities were assigned by comparison with commercial standards and the NIST Mass Spectral Database. The quantification of FAMEs was based on calibration curves of each individual standards, and area of specific ions (m/z 87 for saturated FAMEs, and m/z 74 for monoenoic FAMEs) was used for quantification. The concentration of FAs was normalized to that of internal standards. The semiquantitative chromatograph was shown in FIG. 4. The titers of extracellular S/MCFAs were shown in FIGS. 5, 7 and 8, and intracellular FA composition was listed in FIG. 6.

Example 5: Integrative Expression of the TE-Contained FAS

Figure 9:
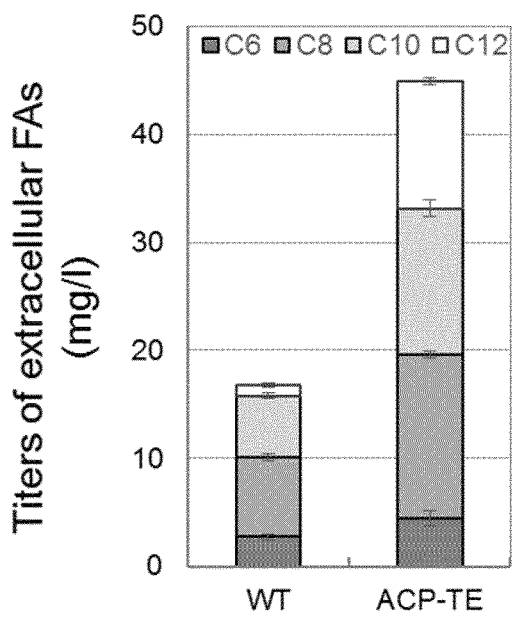
FIG. 9. Titers of extracellular fatty acids produced by *Saccharomyces cerevisiae* YJZ02 integratively expressing corresponding FAS from *Saccharomyces cerevisiae* (Wild type, WT; FAS/TE hybrid, ACP-TE).

Up and downstream regions (about 500 bp) flanking the URA3 gene was amplified from *S. cerevisae* genome and used for integration of the FAS genes in the URA3 locus. The G418 resistance gene cassette KanMX was amplified from pUG6 (Gueldener, U., Heinisch, J., Koehler, G. J., Voss, D. & Hegemann, J. H. (2002) A second set of loxP marker cassettes for Cre-mediated multiple gene knockouts in budding yeast, Nucleic Acids Res. 30, e23.). Expression cassettes for wild type and hybrid *S. cerevisiae* FAS genes were amplified from plasmids pScFAS-WT and pScFAS-ACP-TE, respectively, as described in Example 2. PCR fragments as listed in Table 5 were used to transform the YJZ02 (MATα SUC2 MAL2-8c ura3-52 his3-Δ1 pox1Δ), the isogenic strain derived from *S. cerevisiae* CEN.PK113-11C by deleting the PDX1 gene which encoding the peroxisomal acyl-CoA oxidase, the committing enzyme for fatty acid β-oxidation. The transformants were selected on "YPD+G418" plates (YPD medium containing 200 mg/L G418) and verified by colony PCR using primer pairs ID-dURA3-UP/ScFAS2-R1, ScFAS2-F1/ScFAS1-F1, and ScFAS1-R1/ID-dURA3-DOWN (Looke M, Kristjuhan K, Kristjuhan A: Extraction of genomic DNA from yeasts for PCR-based applications. BioTechniques 2011, 50(5):325-328.). Correct transformants with integrated FAS were pre-cultured in 2 ml "Delft+His+Ura" medium (Delft medium with 100 mg/L histidine and 100 mg/L Uracil) overnight and then the cells were inoculated into 20 ml "Delft+His+Ura" medium in 100 ml Erlenmeyer flask to achieve an initial optical density (OD at 600 nm) of 0.1. After culture for 48 hours, 4 ml culture broth was taken for analysis of extra-cellular fatty acids as described above. The titers of *S. cerevisiae* integratively expressing FAS was showed in FIG. 9.

TABLE 5

PCR fragments used for the integrative expression of the genes or ORFs of FAS

| Name | Primer_1 | Primer_2 | Length (bp) | Templates |
|---|---|---|---|---|
| Inte-ScFAS-1 | dURA3-LHA-F | dURA3-UP-R | 537 bp | Genomic DNA of *S. cerevisiae* |
| Inte-ScFAS-2 | pFAS-TPI1p-F | TPI1p-R | 925 bp | pScFAS1 |
| Inte-ScFAS-3 | dURA3-LHA-F | TPI1p-R | 1429 bp | Fusion products of Inte-ScFAS-1 and 2 |
| Inte-ScFAS-4 | pFAS-TPI1p-F | pFAS-FBA1t-R | 6992 bp | pScFAS-WT |
| Inte-ScFAS-5 | pFAS-TPI1p-F | pFAS-FBA1t-R | 7619 bp | pScFAS-ACP-TE |
| Inte-ScFAS-6 | pFAS-FBA1t-F | TEF1p-F | 7192 bp | pScFAS-WT |
| Inte-ScFAS-7 | TEF1p-R | TEF1p-F | 580 bp | pScFAS-WT |
| Inte-ScFAS-8 | TEF1p-KanMX-F | dURA3-KanMX-R | 1705 bp | pUG6 |
| Inte-ScFAS-9 | URA3-Down-F | URA3-Down-R | 501 bp | Genomic DNA of *S. cerevisiae* |
| Inte-ScFAS-10 | TEF1p-R | URA3-Down-R | 2549 bp | Fusion products of Inte-ScFAS-7, 8 and 9 |

Inte-ScFAS-3, 4, 6 and 10 were used for integration of ScFAS (WT)

Inte-ScFAS-3, 5, 6 and 10 were used for integration of ScFAS (ACP-TE)

Example 6: Rewriting Fungal Fatty Acid Synthases for Tailored Chemical Production

Materials and Methods

Plasmids, Strains and Culture Conditions

All plasmids were constructed by TA cloning kits (Takara Bio, Dalian, China), restriction enzyme digestion/ligation method25, restriction-free method26, Gibson assembly cloning kits (New England Biolabs, MA, US) or DNA assembler. E. coli DH5a was used for plasmid amplification, and E. coli BL21(DE3) was used for recombinant protein expression. If not specify, E. coli was cultured in Luria-Bertani (LB) medium supplemented with appropriate amounts of antibiotics if needed (100 mg/L ampicillin and/or 50 mg/L kanamycin) at 37° C. and 200 rpm. The S. cerevisiae strains BY4741 (MATα his3Δ1 leu2Δ0 met15Δ0 ura3Δ0) or YJZ029 (MATa SUC2 MAL2-8c his3Δ1 ura3-52 Δpox1) derived from CEN PK113-11C (MATa SUC2 MAL2-8c his3Δ1 ura3-52) were used for in vivo plasmid assembly. S. cerevisiae PWY1229 (MATα ura3 leu2 his3 trp1 can1 Δfas1::HIS3 Δfas2::LEU2) was used for complementation test. The strains PWY12 and YJZ02 were used as hosts for S/CMFA production. "YPD" medium (10 g/L yeast extract, 20 g/L peptone and 20 g/L glucose) was used for regular culture of yeast strains. "YPD+G418" containing 200 mg/L G418 (Formedium) was used for selection of transformants with kanMX cassettes. "SC-URA" medium containing 20 g/L glucose, 6.7 g/L yeast nitrogen base without amino acids (YNB, Formedium), and 0.77 g/L complete supplement mixture without uracil (CSM-URA, Formedium) was used for selection of transformants prototrophic to uracil. For the culture of PWY12 strain, fatty acids (100× stock solution containing 50 mM stearic acid and 50 mM palmitic acid dissolved in Tween 80/ethanol (1:1, v/v)) were add to media. 20 g/L agar was added in solid media. Yeast cells were cultured at 30° C., and 200 rpm in liquid media. Cell density (OD600) was measured by GENESYS 20 spectrophotometer (Thermo Scientific).

Cloning the cDNA of RtFAS

The total RNA of R. toruloides was extracted as described before. cDNA was synthesized by PrimeScript High Fidelity RT-PCR Kit (Takara Bio, Dalian, China). The RtFAS1 was amplified from the cDNA by using primers FAS1-L1/FAS1-R1, and three fragments of RtFAS2 were amplified by using the primers FAS2-69F/FAS2-3021R, FAS2-2660F/FAS2-4529R, and FAS2-4304F/FAS2-8881R, respectively. All these cDNA fragments were inserted into pMD19-T vector (Takara Bio, Dalian, China) by TA cloning, and verified by DNA sequencing.

Expression and Purification of the Discrete ACP and PPT Domains from RtFAS

The S1062A mutant of RtACPI (mRtACPI), and S1253A mutant of RtACPII (mRtACPII) were generated via the PCR-based method30. pMD19T-RtFAS2 (2660-4529) was used as template, and primers S1062A-F/S1062A-R and S1253A-F/S1253A-R were used for site-directed mutation of RtACPI and RtACPII, respectively. The primer pairs 41-GST-ACPI-F/41-GST-ACPI-R, 41-GST-ACPII-F/41-GST-ACPII-R and 41-GST-PPT-F141-GST-PPT-R were used to amplify the RtACPI, RtACPII and RtPPT fragments, which were inserted into pET-41(a) vector (Novagen) by the restriction free cloning as described before.

4 ml overnight cultures of E. coli BL21(DE3) with plasmids (expressing GST-wRtACPI, GST-wRtACPII, GST-mRtACPI, GST-mRtACPII, or GST-RtPPT) were inoculated into 400 ml Terrific Broth (TB) media (12 g tryptone, 24 g yeast extract, 4 ml glycerol, 2.31 g KH2PO4 and 12.54 g K2HPO4 per liter) supplemented with 50 μg/ml kanamycin and grown at 37° C. 1 mM IPTG was added into the cultures when the OD600 was about 0.8, and then the cells were grown at 20° C. for 24 hours. The cells were harvested by centrifugation and 4 g wet mass was suspended into 24 ml NBP buffer (50 mM Na2HPO4/NaH2PO4, pH 8.0, 0.5 M NaCl, 1 mM 2-mercaptoethanol, 1 mM PMSF) supplemented with 20 mM imidazole and 1 mg/ml lysozyme. The suspension was kept on ice for 30 min and then disrupted by ultrasonication. Centrifugation (12000 rpm at 4° C. for 20 min) was used to remove the cell debris. The supernatant was mixed with Ni-NTA agarose (Life Technologies), and equilibrated for 15 min on ice. The resin was then sequentially washed by NBP buffer with 20, 40, 60 and 80 mM imidazole and eluted by NBP buffer containing 250 mM imidazole. The eluted proteins were concentrated with Amicon Ultra-15 Centrifugal Filter Units (MWCO 10 kDa, Millipore), and the buffer was changed to phosphopantetheinylation reaction buffer (20 mM Tri-Cl, pH 7.5, 10 mM NaCl, 100 mM KCl, 5 mM MgCl2, 10 mM CaCl2, 1 mM 2-mercaptoethanol, 0.5 mM DTT, 15% glycerol), then the proteins were stored at −20° C.

In Vitro Phosphopantetheinylation of ACP.

200 μL tubes containing 20 μL reaction mixture (20 μg GST-RtACP, 2 μg GST-RtPPT and 0.3 mM CoA in the phosphopantetheinylation reaction buffer) were incubated at 30° C. for 3 hour in a thermocycler (Eppendorf, Germany). The reaction products were stored at −20° C. before analyzed by MALDI-TOF/TOF 5800 mass spectrometer (Applied Biosystems, Framingham, Mass., USA) in a positive linear mode. The instrument was equipped with an Nd:YAG laser at 355 nm with a repetition rate of 400 Hz. The range of laser energy was optimized to obtain good signal-to-noise ratio (S/N). External mass calibration was performed by using standard proteins. For the analysis of proteins, the sample was deposited onto the MALDI target, and then 1 μL matrix solution (sinapinic acid at 20 mg/ml in 50% ACN containing 0.1% TFA) was added for MS analysis. Alternatively, 2.5 μL enterokinase (1 U, Sangon Biotech, Shanghai, China) was added into 10 μL reaction mixture and incubated at 25° C. for 16 hours. The cleaved proteins were analyzed by 16% Tricine-SDS-PAGE (acrylamide:bisacryamide=29:1)31.

Expression and Purification of the RtFAS Complex and its Mutants

RtFAS genes were assembled in S. cerevisiae BY4741 by the method as described, and 2μ episomal vector pYX212 was used as backbone. Complete ORF of RtFAS1 was amplified by primer pair FAS1-5-NdeI/FAS1-3-EcoRI. The fragment was digested with NdeI/EcoRI and inserted into pET22b(+) (Novagen) to generate pET22b-RtFAS1. Complete ORFs of RtFAS2 and its two mutants (S1062A or S1253A) were amplified by primer pair FAS2-5-HindIII/FAS2-3-NotI, digested with HindIII/NotI, and inserted into pET24b(+) (Novagen) to generate pET24b-RtFAS2, pET24b-RtFAS2 (S1062A) and pET24b-RtFAS2 (S1253A), respectively. Plasmids for expression of both RtFAS1 and RtFAS2 were transformed in to E. coli BL21(DE3) simultaneously and selected on LB plates with 100 mg/L ampicillin and 50 mg/L kanamycin. Purification of the RtFAS complexes was described before 17,22, and considerably homogeneous protein complex could be obtained by three step purification (ammonium sulphate precipitation, sucrose density gradient centrifugation and anion exchange chromatography). Fatty acid synthase activity was assayed by monitoring the malonyl-CoA and acetyl-CoA dependent NADPH oxidation. The assay was performed at room temperature (about 25° C.) and in a 200 µL quartz cuvette containing 0.1 M potassium phosphate (pH 7.0), 5 mM DTT, 12.5 µM acetyl-CoA, 50 µM malonyl-CoA, 75 µM NADPH, and about 10 µg purified enzymes. There is no visible decrease in absorption at 340 nm when blank reaction without malonyl-CoA was monitored. And the activity (1 U) was defined as the turnover of 1 µmol NADPH per minute.

Plasmid Construction and Genetic Manipulation.

The RtFAS1 and RtFAS2 were amplified from the pET22b-RtFAS1 and pET24b-RtFAS2, respectively. While the AkFAS was amplified from the genomic DNA of *A. kerguelense*. ScFAS1 and ScFAS2 genes, promoter and terminator fragments were amplified from the genomic DNA of *S. cerevisiae*. 2µ origin from pYX212 was used as replication element, and ScURA3 from pYX212 or KlURA3 from pWJ104232 were used as selection markers. Codon-optimized genes (AcTesA, ShMKS1 and ShMKS2, Supplementary table S7) were synthesized by Genscript. And all these plasmids were transformed into FAS deficient strain PWY12, and their complementation to the fatty acid auxotroph of PWY12 were tested. After transformation, the "SC-URA+FA" plates were used for selection of transformants. Single colonies were inoculated into "SC-URA+FA" liquid medium to amplify the cells for 24-36 hours, then the cells were spin down and washed twice, and grown in "SC-URA" liquid medium for 24 hours to exhaust fatty acid residues. After that, the cells were streaked onto "SC-URA" and "SC-URA+FA" plates, or inoculated into "SC-URA" liquid medium to test the restoring of fatty acid autotroph. The PWY12 harboring empty vector (pYX212) did not grow in "SC-URA" medium. The integration of FAS expression cassettes was also according to the previously described method. About 500 bp homology arms upstream and downstream to the ura3-52 locus, and the KanMX selection marker from pUG633 were used. The ScFAS01, ScFAS27, ScFAS15 and ScFAS28 were integrated into ura3-52 locus of YJZ02 to generate strain ZW201, ZW202, ZW206 and ZW207, respectively. The pZWM1-AcTesA plasmid was constructed by Gibson assembly for episomal expression of 'AcTesA.

Metabolite Extraction and Quantification

Prior to metabolite extraction, the cells were grown in 100 ml shake flasks with 20 ml Delft medium supplemented with constituents as needed (100 mg/L uracil, 100 mg/L histidine and/or 100 mg/L tryptophan) for 48 hours if not specify. The initial optical density (OD at 600 nm) was 0.1. The extracellular S/MCFAs were extracted and esterified by previously described method10 with modifications. Briefly, 0.5 ml 10% (w/v) NaCl, 0.5 ml glacial acetate (containing 10 µg heptanoic acid and 10 µg pentadecanoic acid as internal standards) and 2 ml 1:1 (v/v) chloroform/methanol were added to 4 ml culture broth in extraction tubes (16×100 mm PYREX® culture tubes and GPI 15-415 Threaded Screw Cap, Corning Inc., US). After vortex at 1800 rpm for 30 min, the mixtures were centrifuged at 3000 rpm for 10 min, and the lower chloroform phase was transferred into a clean extraction tube by a glass syringe. Fatty acid methyl esters (FAMEs) were generated by mixing 1 ml boron trifluoride/ methanol (14%, Sigma-Aldrich) with 200 µL of chloroform extract, and esterification at room temperature overnight. This was based on the ready and fast esterification of free fatty acids by boron trifluoride/methanol 35. The FAMEs were then extracted by adding 1 ml H2O and 600 µL hexane, vortex at 1500 rpm for 10 min, and centrifugation at 1000 g for 10 min. 200 µL taken from the hexane phase was analyzed by GC/MS. For the strains highly producing S/MCFAs (ZW201, ZW202, ZW206 and ZW207), 1 ml culture broth diluted in 3 ml Milli-Q H2O was used.

The intracellular total fatty acids (in the form of FAMEs) were extracted after microwave-assisted esterification of yeast biomass according to a previously described method with minor modifications. 1 ml hexane, 2 ml boron trifluoride/methanol (14%, Sigma-Aldrich), 10 µg heptanoic acid and 10 µg pentadecanoic acid were add to 10 mg lyophilized biomass for derivatization of total fatty acids, after microwave-assisted esterification, the FAMEs in the upper hexane phase were taken for GC/MS analysis.

The extracted short/medium chain FAMEs were analyzed by a FOCUS GC/ISQ single quadrupole mass spectrometer system (Thermo Fisher Scientific Inc., USA) using a ZB-50 column (30 m*0.25 mm*0.25 um, Phenomenex Inc., UK). Helium was used as carrier gas (3 ml/mim). 1 µL samples were injected (splitless, 240° C.), and oven temperature was set at 30° C. for 2 min; increased to 150° C. with a ramp rate of 40° C./min, held for 2 min; increased to 250° C. with a ramp rate of 10° C./min, held for 3 min. For long chain FAMEs, however, a ZB-WAX column (30 m×0.25 mm×0.25 um, Phenomenex Inc., UK) was used, and the initial oven temperature was 50° C. The temperature of MS transfer line and ion source were set as 250° C. and 200° C., respectively. The fragment ions derived from electron ionization (70 eV) were detected in a full scan mode (50-450 m/z) and selected ion monitoring mode (74 m/z). Area of the specific ion (m/z 74) was used for quantification of FAMEs.

Results

Figure 11:
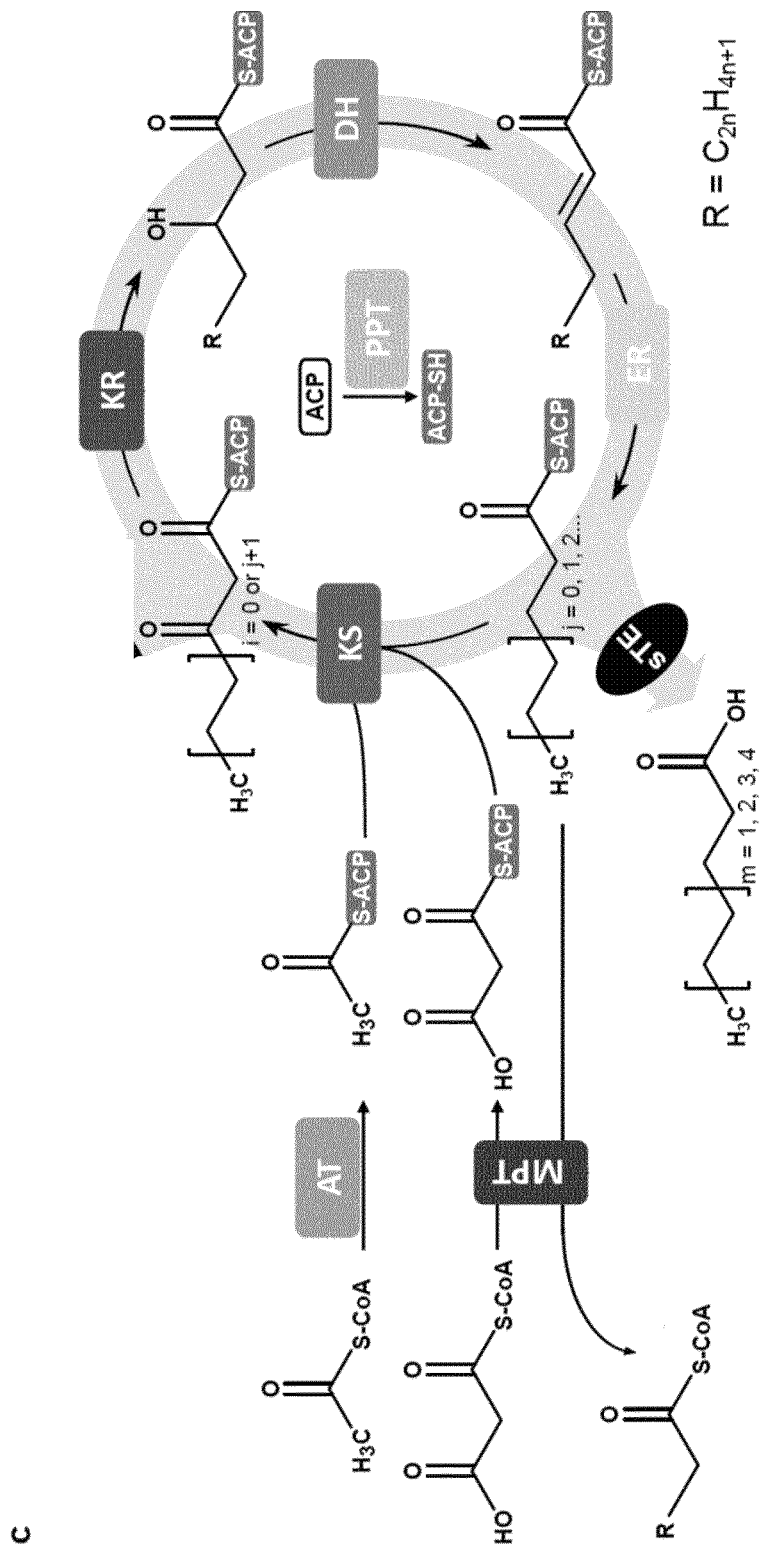
FIG. 11. Design and strategy for engineering the fungal fatty acid synthases (FASs) to synthesize tailored oleochemicals. (a) Domain composition of fungal FAS variants. (b) Cross-section presentation of the fungal FAS structure. Position of each domain is only shown for one of three sets of active sites in the upper compartment. A heterologous enzyme (black circle) can be inserted into the reaction chamber as shown. (c) Reaction cycles catalyzed by engineered fungal FASs. A heterologous short chain thioesterase (sTE) was integrated into the elongation cycles to release short/medium chain fatty acids. AT, acetyl-transferase; ER, enoyl reductase; DH, dehydratase; MPT, malonyl-palmitoyl transferase; ACP, acyl carrier protein; KS, ketoacyl synthase; KR, ketoacyl reductase; PPT, phosphopantetheinyl transferase.

Fungal type I FAS complex is a barrel-shaped hollow particle separated by a central wheel at the equator to form two reaction chambers (FIG. 11b). Fungal FASs are encoded by one or two polypeptides, and typically contain seven catalytic enzyme domains and one ACP domain which acts as a protein cofactor (FIGS. 11b and 11c). ACP is activated by phosphopantetheinyl transferase (PPT) catalyzed attachment of a prosthetic phosphopantetheine group, which provides a thiol group to link the growing fatty acyl chain. The ACP domains are located inside the compartmented chambers and tethered by two flexible linkers which are anchored to the chamber wall and central wheel (FIG. 11b). The ACP carrying acyl cargo dynamically interacts with other catalytic domains to fulfill the complete reaction cycle. As the ACP and its adjacent linkers are mobile in the hollow reaction chambers, we speculated that these flexible regions could readily be modified, and a heterologous enzyme utilizing acyl-ACP as substrate therefore could be integrated into the FAS to create a novel synthetic FAS machinery that can produce diverse fatty acids and fatty acid derived chemicals (FIGS. 11b and 11c). Prior genomic annotation of oleaginous yeast *Rhodosporidium toruloides* revealed a special FAS which is different from FASs from other fungal species according to their protein domain architecture (FIG. 11a). However, FAS from *R. toruloides* (RtFAS) assembles into the typical fungal FAS structure revealed by cryo-EM analysis. More interestingly, the RtFAS contains two putative ACP domains highly similar to each other (Sequence alignment was performed of ACP domains from fungal FASs. The sequences include ScACP from Fas2 of *S. cerevisiae* (Genbank accession number, P19097.2), CnACP from Fas1 of *C. neoformans* (Genbank accession number, XP_571100.1), UmACP from Fas of *U. maydis* (Genbank accession number, XP_759118.1), AkACPI and AkACPII from Fas of *A. kerguelense* (JGI protein ID, 103951), PgACP from Fas2 of *P. graminis* (Genbank accession number, XP_003889657.1), RtACPI and RtACPII from Fas2 of R. toruloides (Genbank accession number, EMS21268.1), CrACP from Fas of C. reversa (JGI protein ID, 10860); data not shown).

We found both ACPs could be in vitro phosphopantetheinylated by the cognate PPT from RtFAS, when discrete ACP and PPT domains (as purified GST fusion proteins) were used. It was also shown that the phosphopantetheinylation of ACPs was dependent on the coenzyme A, the PPT enzyme and the conserved serine residue in the phosphopantetheine attachment site (FIG. 12 and Table 6).

TABLE 6

Determination of the molecular weight of ACPs by MOLDI-TOF mass spectrometry. The molecular weight of ACPs increase 340 Da during the phosphopantetheinylation.

| Protein | Theoretical MW (Da) | Measured MW (Da) | | $\Delta M$ (Da) |
|---|---|---|---|---|
| | | Untreated by PPT | Treated by PPT | |
| GST-mACPI | 49515 | 49508 | 49510 | 2 |
| GST-wACPI | 49531 | 49519 | 49851 | 332 |
| GST-mACPII | 49417 | 49465 | 49419 | 46 |
| GST-wACPII | 49433 | 49476 | 49798 | 322 |

We have established the purification protocols for the recombinant RtFAS complex in E. coli, from which stable and active FAS complex could be obtained by serially (NH4)2SO4 precipitation, sucrose density gradient ultracentrifugation, and DEAE-sepharose anion exchange chromatography. To investigate the roles of duplicated ACPs in fatty acid synthesis, the conserved serine residues in the phosphopantetheine attachment sites of either ACPs were mutated to alanine residues. Enzymatic assays of the purified FAS complexes by monitoring the NADPH oxidation showed that both mutants (S1062A and S1253A) had comparable fatty acid synthesis activity to wild type (FIG. 13). Consistently, complementation of Saccharomyces cerevisiae PWY12 containing ScFAS1 and ScFAS2 deletion with wild type RtFAS (RtFAS01) and mutated versions of RtFAS (S1062A, RtFAS02 and S1253A, RtFAS03, FIGS. 14a and 14b), and almost the same amount of fatty acids produced by the mutants (RtFAS02 and RtFAS03) comparing with the wild type RtFAS01 (FIG. 14b and Table 7) indicated that both ACPs played similar roles in fatty acid synthesis and that one single ACP was sufficient for the activity of RtFAS.

Figure 14:
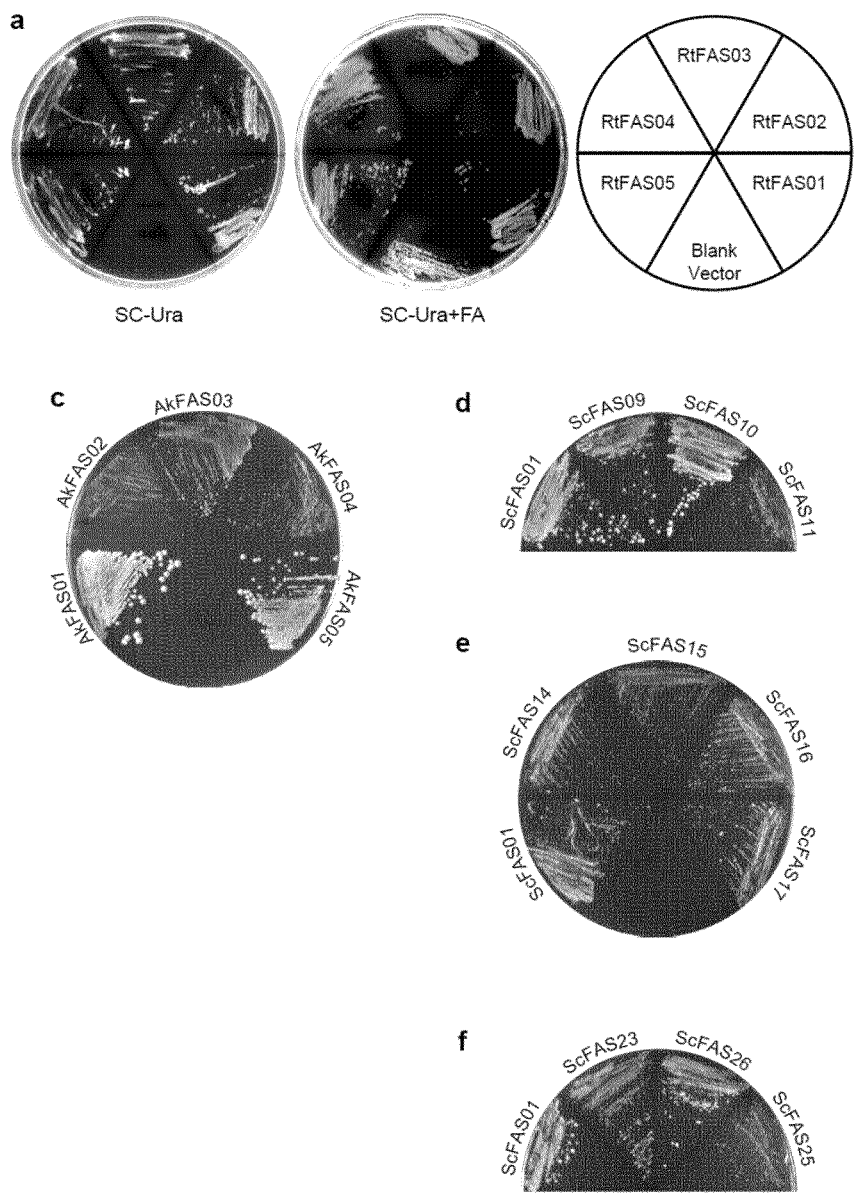
FIG. 14. The complementation of FAS1 and FAS2 deletion in *S. cerevisiae* PWY12 by different FASs and their mutants. (a) Growth of PWY12 with corresponding plasmids on plates containing fatty acids (SC-Ura+FA) or without fatty acids (SC-Ura). The train with blank vector (pYX212) could only grow on plates supplemented fatty acids. (b) Growth curves of the PWY12 strains with plasmids as indicated in Delft media with 100 mg/L tryptophan. The cells were cultured in volume of 200 ul (in honeycomb plate), and the optical density was monitored by Bioscreen C MBR instrument. (c)-(f), Growth of PWY12 with plasmids as indicated on plates without fatty acids (SC-Ura).
Figure 14:
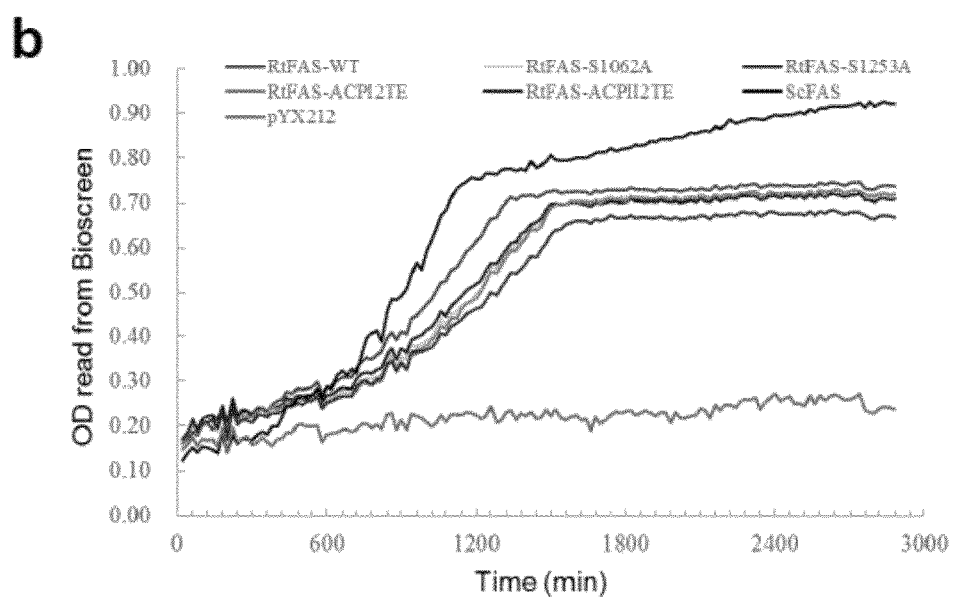

(S2150A) and AkFAS03 (S2340A) harboring one active ACP were expressed in S. cerevisiae PWY12, respectively (FIG. 14a). It showed as well that only one ACP in AkFAS was sufficient for fatty acid synthesis (FIG. 14c).

Figure 15:
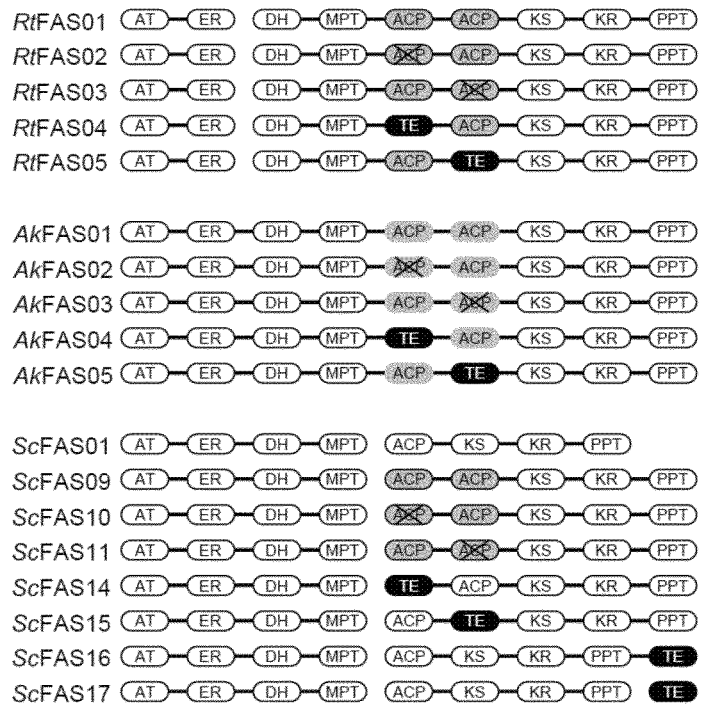
FIG. 15. Synthesis of oleochemicals by engineered fungal FASs. (a) Schematic presentation of the engineered fungal FASs. The conserved serine residues of ACPs were mutated to alanine residues to inactivate the ACP domains. In ScFAS27 and ScFAS28, the G1250S, S1251W mutations were introduced into ketoacyl-ACP synthase (KS) domain of ScFas2 protein. In engineered ScFAS, the flexible linker separating two tandem ACPs in RtFAS was used to isolate the heterologous proteins and the ACP domain. (b-d) Production of extracellular fatty acids by strain *S. cerevisiae* PWY12 expressing fungal FASs as indicated. Hexanoic acid (C6), octanoic acid (C8), decanoic acid (C10), dodecanoic acid (C12) were extracted and quantified. More than 3 independent cultures were used for product quantification. Mean±SD was presented. *, $p<0.01$, and **, $p<0.001$. Student's t test.
Figure 15:
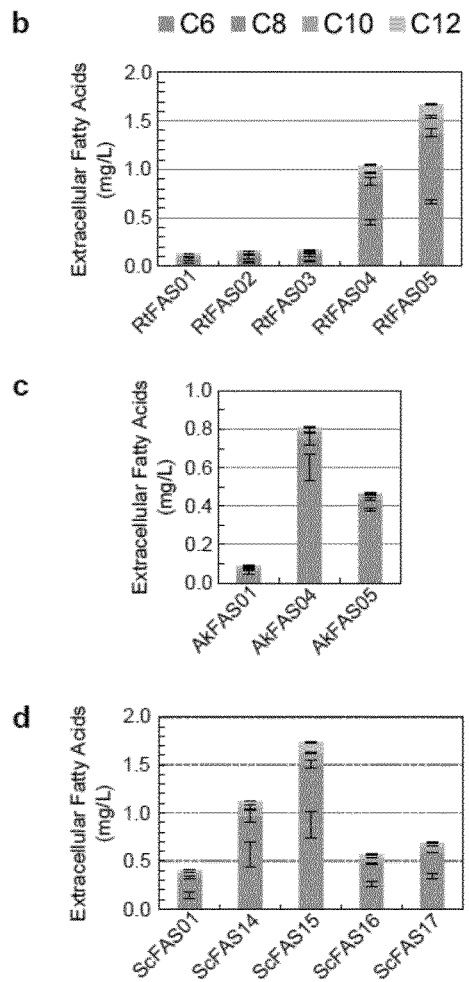

After demonstrating the redundant roles of duplicated ACPs in fungal type I FASs, we considered to replace either ACPs in RtFAS and AkFAS with a short chain acyl-ACP thioesterase (sTE) to hydrolyze acyl-ACP intermediates and produce S/MCFAs, which are precursors of many industrial chemicals, and also associated with improved property of biofuels. A free-standing thioesterase ('AcTesA) from Acinetobacter baylyi which prefers to produce S/MCFAs23 was inserted into the FASs (FIG. 15a). According to the structures of fungal FASs, the embedded sTE would localize in the reaction chambers and readily access the acyl-ACP substrates. From the complementation test, we found that sTE contained FASs (RtFAS04, RtFAS05, AkFAS04 and AkFAS05) could synthesize essential fatty acids to support the growth of S. cerevisiae PWY12 which was auxotrophic to fatty acids (Supplementary FIG. 15a-c). Then we extracted and quantified the extracellular fatty acids produced by S. cerevisiae PWY12 expressing different FAS variants, and found that the hybrid FASs produced 5-10 times more extracellular S/MCFAs compared to the corresponding wild type RtFAS and AkFAS (FIGS. 15b and 15c). Especially the strain expressing RtFAS05 produced 0.67 mg/L hexanoic acid and 0.72 mg/L octanoic acid which were about 20 folds more than those produced by the wild type RtFAS01 (FIG. 15b). Interestingly, the RtFAS04 and RtFAS05 produced about 20% and 40%, respectively, less C18 fatty acids compared to RtFAS01, showing the embedded sTE indeed intervened in the acyl chain elongation (Table 7).

The EM structure of RtFAS superimposes well to the X-ray structure of Thermomyces lanuginosus and Saccharomyces cerevisiae FAS, suggesting these FASs harbor reaction chambers in similar size. When the single ACP of FAS from S. cerevisiae (ScFAS) was replaced with tandem double ACPs from RtFAS, the hybrid ScFAS09 containing two ACPs retained the fatty acid synthesis activity (FIG. 15), which indicated that the reaction chambers of fungal FASs could accommodate more contents. Similarly, ScFAS10 and ScFAS11 containing one active ACP and one inactivated ACP complemented the FAS deletion in S. cerevisiae PWY12. This made us constructing similar hybrid ScFASs

TABLE 7

Intracellular total fatty acids produced by PWY12 expressing RtFAS and it mutants.

| | C6 | C8 | C10 | C12 | C14 | C16 | C16:1 | C18 | C18:1 | Total |
|---|---|---|---|---|---|---|---|---|---|---|
| RtFAS01 | 0.009 ± 0.0008 | 0.003 ± 0.0002 | 0.036 ± 0.005 | 0.051 ± 0.005 | 0.094 ± 0.008 | 5.02 ± 0.27 | 25.19 ± 1.77 | 1.35 ± 0.18 | 37.81 ± 1.15 | 69.6 |
| RtFAS02 | 0.009 ± 0.0006 | 0.005 ± 0.0016 | 0.037 ± 0.003 | 0.043 ± 0.006 | 0.077 ± 0.007 | 4.13 ± 0.35 | 21.59 ± 1.72 | 1.88 ± 0.32 | 39.69 ± 3.74 | 67.5 |
| RtFAS03 | 0.010 ± 0.0017 | 0.007 ± 0.0003 | 0.034 ± 0.006 | 0.050 ± 0.002 | 0.079 ± 0.002 | 4.08 ± 0.08 | 21.34 ± 0.39 | 1.73 ± 0.12 | 40.41 ± 0.67 | 67.7 |
| RtFAS04 | 0.012 ± 0.0002 | 0.092 ± 0.009 | 0.140 ± 0.006 | 0.304 ± 0.006 | 0.192 ± 0.0003 | 4.15 ± 0.03 | 22.83 ± 0.06 | 1.47 ± 0.01 | 29.95 ± 0.47 | 59.1 |
| RtFAS05 | 0.012 ± 0.0007 | 0.145 ± 0.008 | 0.196 ± 0.007 | 0.507 ± 0.017 | 0.271 ± 0.003 | 4.52 ± 0.10 | 26.35 ± 0.04 | 0.84 ± 0.02 | 22.71 ± 0.59 | 55.6 |

Unit. mg/g DCW. Data from three independent culture, and mean ± sd were presented.

We also found a few fungal FASs from diverse phylogenetic clades containing duplicated ACPs. Similarly, the FAS from Aplanochytrium kerguelense (AkFAS01) encoded by one single polypeptide and its two mutants AkFAS02

Figure 16:
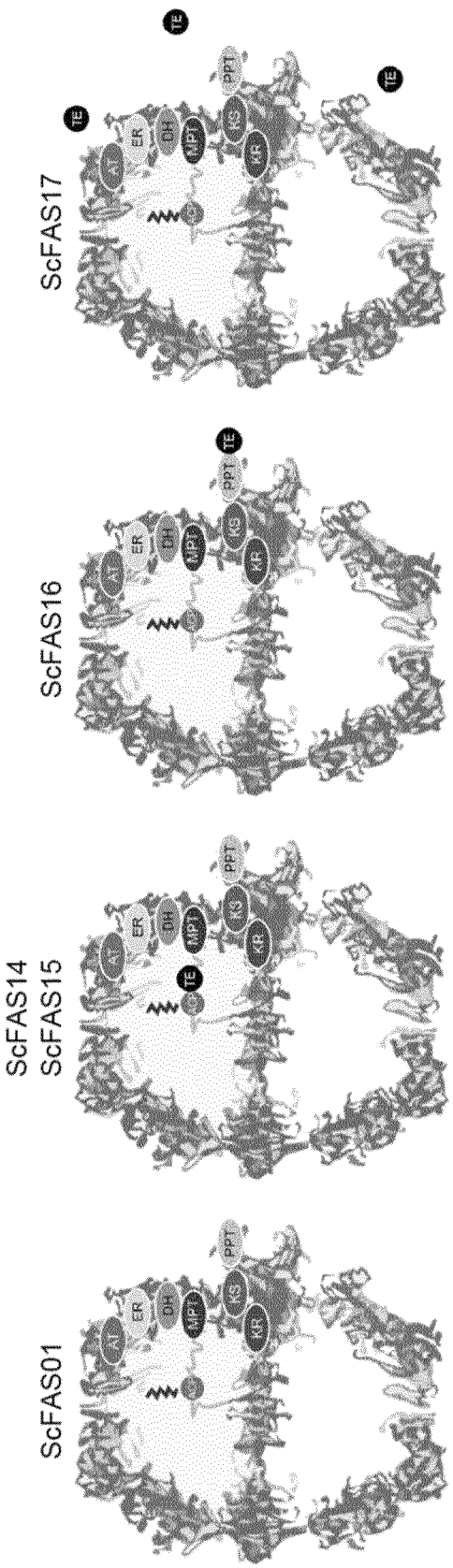
FIG. 16. Schematic presentation of ScFAS with embedded (ScFAS14 and ScFAS15), peripheral (ScFAS16) or free (ScFAS17) sTE.
Figure 17:
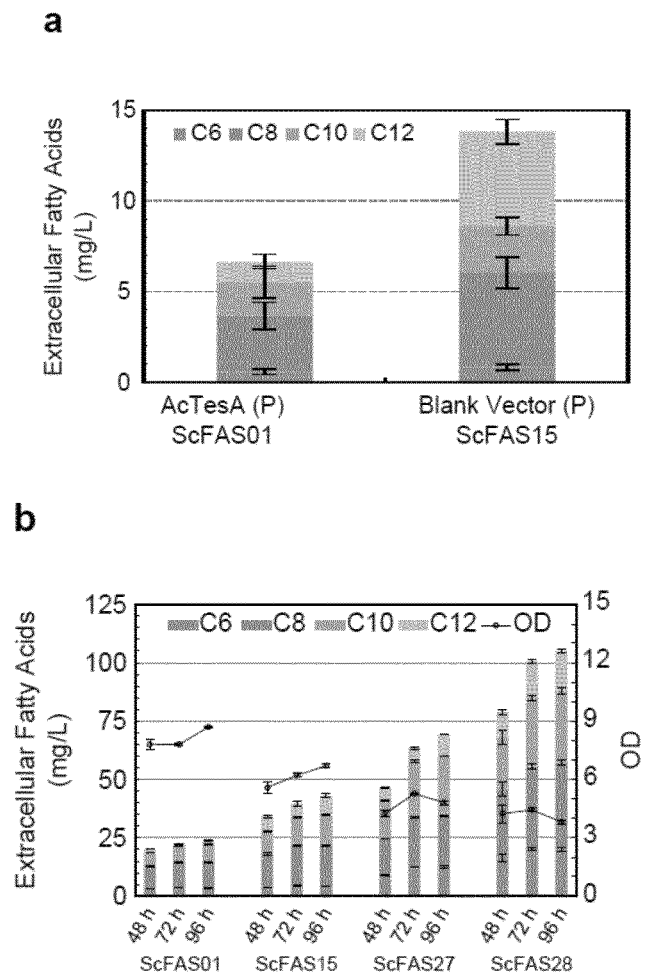
FIG. 17. Production of S/MCFAs in YJZ02 integrated with engineered ScFAS. (a) S/MCFA production in ZW201 strain (YJZ02 with a chromosome integrated ScFAS01) with a plasmid expressing AcTesA and ZW206 strain (YJZ02 with a chromosome integrated ScFAS15) with an empty vector. Cells were cultured in Delft medium supplemented with 100 mg/L Histidine for 48 hour. (b) S/MCFA production and optical density (OD) of strains ZW201, ZW206, ZW202 (YJZ02 with a chromosome integrated ScFAS27) and ZW207 (YJZ02 with a chromosome integrated ScFAS28). Cells were cultured in Delft medium supplemented with 100 mg/L Histidine and 100 mg/L Uracil for 48, 72 and 96 hours. (c) pH adjusted culture of ZW207 in Delft medium supplemented with 100 mg/L Histidine and 100 mg/L Uracil. The arrow showed the addition of sterile KOH solution (2 M) to change the pH to 6.0. (d) S/MCFA production of ZW207 during pH unadjusted and pH adjusted culture as shown in (c). Mean±SD of 3-4 independent cultures were presented.

(ScFAS14 and ScFAS15) by inserting a sTE adjacent to the ACP domain (FIG. 1a). We found that the ScFAS14 and ScFAS15 produced an increased level of S/MCFAs comparing with the wild type ScFAS01. To further address if the embedded sTEs worked in the reaction chambers and hydrolyzed the acyl-ACP instead of acyl-CoA, which was released by malonyl/palmitoyl transferase (MPT) and then diffused back into the hollow through open windows in the wall of FAS particle, the S/MCFA production by FASs with embedded sTEs (ScFAS14 and ScFAS15) was compared with that by FASs with peripheral or free sTEs. The acyl-CoA was used as substrate of sTEs in ScFAS14 and ScFAS15 if similar amounts of S/MCFAs were produced by these FASs, while acyl-ACP would be used as substrate of sTEs in ScFAS14 and ScFAS15 if both of them produced more S/MCFAs than FASs with peripheral or free sTEs. Therefore, the sTE was fused to the C-terminus of PPT in order to attach peripheral sTEs to the FAS particle. ScFAS16 complemented the FAS deletion in S. cerevisiae PWY12, suggesting this mild modification did not perturb the FAS structure much. The free sTE was also co-expressed with the ScFAS (ScFAS17). We found the S/MCFAs produced by ScFAS14 and ScFAS15 were 60-210% more than those produced by ScFAS16 and ScFAS17, in which the sTEs would have limited access to the acyl-ACP substrates tethered in the FAS chambers (FIG. 15d and FIG. 16). Moreover, comparing with high level expression of sTE by high copy plasmid, integrative expression of ScFAS15 (single copy) produced 2 times more S/MCFAs (FIG. 17a). These results clearly showed that the embedded sTE in ScFAS worked better than peripheral or free sTE to ScFAS for S/MCFA production.

The invention claimed is:

1. A recombinant fungal cell comprising, expressing, or capable of expressing a thioesterase (TE) and a fungal fatty acid synthase (FAS) or a FAS1 or a FAS2 subunit thereof, wherein said TE and said fungal FAS, FAS1, or FAS2 are encoded as a single open reading frame (ORF).

2. The recombinant fungal cell according to claim 1, wherein a polynucleic acid sequence encoding said TE is adjacent to a polynucleic acid sequence encoding an acyl carrier protein (ACP).

3. The recombinant fungal cell according to claim 1, comprising a FAS encoding sequence or comprising a FAS1 and FAS2 encoding sequence originating from a FAS gene having at least two ACP encoding nucleotide sequences, wherein one of said ACP encoding nucleotide sequences is replaced by a TE encoding nucleotide sequence.

4. The recombinant fungal cell according to claim 1, wherein said FAS, FAS1 or FAS2 is from *Saccharomyces cerevisiae, Rhodosporidium toruloides* or *Aplanochytrium kerguelense*.

5. The recombinant fungal cell according to claim 1, wherein said TE is an acyl-CoA/ACP TE.

6. The recombinant fungal cell according to claim 1, which is a bacterial cell, a fungal cell, or an algae cell.

7. A recombinant polynucleic acid encoding a fungal fatty acid synthase (FAS) or a FAS1 or FAS2 subunit thereof, and a thioesterase (TE).

8. A recombinant polypeptide encoded by the recombinant polynucleic acid according to claim 7.

9. A recombinant vector comprising the recombinant polynucleic acid according to claim 7.

10. A method for producing fatty acids, comprising the steps of
    (i) providing the recombinant fungal cell according to claim 1; and
    (ii) culturing said recombinant fungal cell under suitable culture conditions.

11. The method of claim 10 further comprising reduction, hydrogenation, decarboxylation or decarbonylation of said fatty acids to produce a hydrocarbon.

12. The method of claim 10, further comprising reducing said fatty acids to produce a fatty alcohol or fatty aldehyde.

13. The method of claim 10, wherein said fatty acids are short chain fatty acids (SCFA) or medium chain fatty acids (MCFA).

14. The recombinant fungal cell according to claim 1, wherein said TE is a short or medium chain acyl-CoA/ACP TE.

15. The method of claim 11, wherein said hydrocarbon is as a medium chain hydrocarbon or a short chain hydrocarbon.

16. The method of claim 12, wherein said fatty alcohol or fatty aldehyde is a medium chain fatty alcohol or aldehyde or a short chain fatty alcohol or aldehyde.

17. The method of claim 10, wherein said fatty acids are C6-C12 fatty acids.

* * * * *

SEQUENCE LISTING

<160> NUMBER OF SEQ ID NOS: 1

<210> SEQ ID NO 1
<211> LENGTH: 3801
<212> TYPE: DNA
<213> ORGANISM: Rhodosporidium toruloides

<400> SEQUENCE: 1

```
atgaacggcc gagcgacgcg gagcgtgact gggacgtcga cgccggtcca cacggcgacg      60
acccgacccc tcgtcctctt gcacccctcg acccaaaccc gcatctcgct gcacgtcccc     120
tccacgtcgc aggaatggat cgccgccgaa gtcgcgcgcg acaccttcca ggactggctt     180
cacgctgccg agaagagcgg aaacctcgtc ggattcgagg cggccgagct tgacgacgag     240
caggctggcg agggcgacga cgagaaggag ctcgtcctca ccgcctactt cttgaagcac     300
gttgccggcc ttctcccctt cccgtcgaca gctacctccc ccgccaccgc cgccgtcctc     360
ctcgccgcct tcaaccactt tgcgtccgtc tacctcagcg gaaccgatgt tcacaccctc     420
actgcctcgc tcgctgctcc cgtccgcgct ctcgtcatct cgtccttctt cctcgccaag     480
accaagctcg aggtcgaggg actcggcaag gtcttgccca agcagtccga gtcggcgctc     540
ctgcagaagg ctgcgaccgg ccaggcagag gtcttcgctc tcttcggtgg tcagggaatg     600
aacgaggtct actttgacga gctccagacc ctccacgacc tttacacccc gctgcttacg     660
cccttcctcg cccgcgcctc cgaacacctc gtctctctcg ctgccgccga gcagcacacc     720
ctcctttacg accactcgct cgacgccctt gcctggctgc aagatccctc taccegcccc     780 gaagtcccct acctcgcgac ttgcgccgtc tcgctccctc tcatcggtct cactcagctc     840
tgccagtacg tcgtgtacgg caagggctcg tcgctcggtc ccgccgagct cggcgccaag     900
ttcaagggcg cgaccggcca ctcgcagggt gtcgtctcgg ctcttgtcat cgcgcacgag     960 tacctcccg cgtccaagga cggcagcgac gcgtgggagc ctttctacga gcaggccctt    1020
cgcggtttga ccgtcctctt ccagatcggt ctccagggca cgctcgcctt cccctccatc    1080
gccatttcgc ccgctctcga gtcgagctcg gtcgagaatg cgcagggtgt cccgactgcc    1140
atgcttgccg tcaccggcct cgacctcaag tcgctcgaga agaagatcgc cgaggtcaat    1200
gggcacgtca agtctgaggg ccgcgacgag accgtctcga tcagtctcta caacggtgcg    1260
agggcgttcg tcgtcactgg tgcgccgaag gacctcgtcg gtctcgccga cggccttcgc    1320
aagaaccgcg cgccggccgg caaggaccag tcgaagatcc cgcactcgaa gcgtctcccc    1380
gtcttctcga tgcgcttcct ccccatcaac gttccctacc actcgcatct cctccaaggc    1440
gcgaccgaga aggcgctcgc gacgttctcg gctgaggagg ccgcccactg ggcgccttca    1500
tcgttcacct gcgccgtcta caacaccgag gacggctccg acatgcgcca gctctcggct    1560
```

```
tcgtcggttc tcgagtcggt cttccagcag atcttcacct cgcccattca ctgggtctcg    1620
cacgccacca acttcccctc gtccgcgacg cacgccatcg atttcggcac gggcggcgcg    1680
agcggcatcg gttcgctctg cgcgcgcaac tgggagggcc gcggtatccg cacgattatg    1740
ctcggcaacc gcggcgaggg cgttggtgcc ggcaaggagg cttggggcaa gaaggtcccg    1800
accgaggaga agtggaacga gcgcttccac cctcgcctcg tccgcaccag cgacggcaag    1860
atccacctcg acacgccctt ctcgcgcctc ctctcgaagc cgcccctcat ggtcggtggt    1920
atgaccccga cgaccgtcaa ggccggcttc gtctcggccg ttctccgcgc gggctaccac    1980
atcgagctcc tggcggcgg tcactacaac gagaaggctg tccgtgccaa ggtcgccgag    2040
atccagaagc tcgtgaacaa gcccggcatg gcatcaccc tcaactcgct ctacatcaac    2100
cagcgccagt ggacgttcca gttcccgctc tgggccaaga tgaagcagga gggcgagccc    2160
gtcgagggtc tctgtgttgc tgccggtatt ccctcaaccg agaaggccaa ggagatcatc    2220
gacacgctcc gcgaggccgg catcaagcac gtctcgttca gcccggttc ggtcgacggc    2280
atccgccagg tcgtcaacat cgcctccgcc aaccccgact tccccatcat cctccagtgg    2340
actggtggtc gcgccggcgg tcaccactcg tgcgaggact ccacgccccc gatcctcgcg    2400
acgtacgctt cgatccgtca gcaccccaac atcaagctcg tcgccggctc tggcttcggc    2460
tcggctgagg gatgctaccc ttacctttcg ggcgagtggt cggagaagca gtacggcgtc    2520
gcgcgcatgc cgttcgacgg cttcatgttt gcttcgtggg tcatggtcgc caaggaggcg    2580
cacacgagcg agtcggtcaa gcagctcatc gtcgacgcgc ctggtgtcga ggatggccag    2640
tgggagcaga cgtacgacaa gccgaccggc ggcatcctca ccgtcaactc ggagcttggc    2700
gagccgatcc acaaggtcgc gactcgtggt gtcaagctgt gggccgagtt cgacaagaag    2760
gtcttctcgc tgtcgaagga gaagcagctc gcatggctcg ccgacaacaa gaagtacgtt    2820
atcgaccgcc tcaacgccga tttccagaag ccctggttcc ccgccaaggc cgacggctct    2880
ccttgcgacc ttgccgacat gacctacgcc gaggtcaacg cccgcctcgt ccgcctcatg    2940
tacgtcgcgc acgagaagcg ctggatcgac ccgtcgctcc gcaacctcgt cggcgactgg    3000
atccgccgtg ttgaggagcg tctctcgaac gtcaacgact cgggcatcaa gatctcggca    3060
ctccagtcgt actcggagct gaacgagcct gaggcgttcc tcaagcagtt cctcgcccag    3120
tacccgcagg ccgaggacca gatcctcgcc tccgccgacg tttcctactt cctcgccatc    3180
tctcaacgcc ccggacagaa gcccgtcccc ttcatccccg tcctcgacgc caacttcagc    3240
atctggttca agaaggactc gctgtggcag gccgaggaca tcgaggccgt ctttgaccag    3300
gacccgcagc gtgtctgcat cctccaggga ccggtcgccg ccaagcactg cacctcgacg    3360
cagacgccca tcgccgagat gctcggcaac atcgagcacc agctcgtcaa gaacgtcctg    3420
gacgactact acggcggcga cgagtcccag atcccgacta tcgactacct cgcgccccct    3480
cccaagccgg tcgacgccgg cgctatcctc gccgagaaca catcgcgca ctcggtcgag    3540
gagctcgccg acggcggcaa gaagcatgtc tactcgatca acggtgtcct cccgccgacg    3600
ggcgactggc atgccgcact cgccggcccc aagctcgact ggctccaggc gttcctctcc    3660
aacgtctcga ttcaggcggg cgagcagtcg attcctaacc ccgtcaagaa ggtgctggcg    3720
ccgaggcacg ggcagcgggt cgagctcacc ctgaacaagg acggccagcc cctcaagctc    3780
gacgtcttcg gcgggctctg a                                              3801
```